US010106600B2

(12) United States Patent
Brinkmann et al.

(10) Patent No.: US 10,106,600 B2
(45) Date of Patent: Oct. 23, 2018

(54) BISPECIFIC ANTIBODIES

(75) Inventors: Ulrich Brinkmann, Weilheim (DE);
Rebecca Croasdale, Antdorf (DE);
Harald Duerr, Starnberg (DE);
Christian Klein, Bonstetten (CH);
Erhard Kopetzki, Penzberg (DE);
Wilma Lau, Munich (DE); Joerg Thomas Regula, Munich (DE);
Juergen Michael Schanzer, Munich (DE); Pablo Umana, Waedenswil (CH);
Katharina Wartha, Munich (DE)

(73) Assignee: Roche Glycart AG (CH)

( * ) Notice: Subject to any disclaimer, the term of this patent is extended or adjusted under 35 U.S.C. 154(b) by 233 days.

(21) Appl. No.: 13/070,582

(22) Filed: Mar. 24, 2011

(65) Prior Publication Data
US 2011/0293613 A1 Dec. 1, 2011

(30) Foreign Application Priority Data

Mar. 26, 2010 (EP) ..................................... 10003270

(51) Int. Cl.
*A61K 39/00* (2006.01)
*C07K 16/22* (2006.01)
*C07K 16/28* (2006.01)
*C07K 16/46* (2006.01)

(52) U.S. Cl.
CPC .......... *C07K 16/22* (2013.01); *C07K 16/2863* (2013.01); *C07K 16/468* (2013.01); *A61K 2039/505* (2013.01); *C07K 2317/21* (2013.01); *C07K 2317/24* (2013.01); *C07K 2317/31* (2013.01); *C07K 2317/41* (2013.01); *C07K 2317/526* (2013.01); *C07K 2317/56* (2013.01); *C07K 2317/622* (2013.01); *C07K 2317/624* (2013.01); *C07K 2317/64* (2013.01); *C07K 2317/72* (2013.01); *C07K 2317/73* (2013.01); *C07K 2317/732* (2013.01); *C07K 2317/76* (2013.01); *C07K 2317/92* (2013.01)

(58) Field of Classification Search
CPC ............................................... A61K 2039/505
USPC ............................. 530/387.1, 387.3, 388.22
See application file for complete search history.

(56) References Cited

U.S. PATENT DOCUMENTS

| 3,773,919 | A | 11/1973 | Boswell et al. |
|---|---|---|---|
| 3,896,111 | A | 7/1975 | Kupchan et al. |
| 4,120,649 | A | 10/1978 | Schechter |
| 4,137,230 | A | 1/1979 | Hashimoto et al. |
| 4,150,149 | A | 4/1979 | Wolfsen et al. |
| 4,151,042 | A | 4/1979 | Higahide et al. |
| 4,248,870 | A | 2/1981 | Miyashita et al. |
| 4,256,746 | A | 3/1981 | Miyashita et al. |
| 4,260,608 | A | 4/1981 | Miyashita et al. |
| 4,265,814 | A | 5/1981 | Hashimoto et al. |
| 4,294,757 | A | 10/1981 | Asai |
| 4,307,016 | A | 12/1981 | Asai et al. |
| 4,308,268 | A | 12/1981 | Miyashita et al. |
| 4,308,269 | A | 12/1981 | Miyashita et al. |
| 4,309,428 | A | 1/1982 | Miyashita et al. |
| 4,313,946 | A | 2/1982 | Powell et al. |
| 4,315,929 | A | 2/1982 | Freedman et al. |
| 4,317,821 | A | 3/1982 | Miyashita et al. |
| 4,322,348 | A | 3/1982 | Asai et al. |
| 4,331,598 | A | 5/1982 | Hasegawa et al. |
| RE30,985 | E | 6/1982 | Cartaya |
| 4,361,544 | A | 11/1982 | Goldberg |
| 4,361,650 | A | 11/1982 | Asai et al. |
| 4,362,663 | A | 12/1982 | Kida et al. |
| 4,364,866 | A | 12/1982 | Asai et al. |
| 4,371,533 | A | 2/1983 | Akimoto et al. |
| 4,419,446 | A | 12/1983 | Howely et al. |
| 4,424,219 | A | 1/1984 | Hashimoto et al. |
| 4,444,744 | A | 4/1984 | Goldenberg |
| 4,450,254 | A | 5/1984 | Isley et al. |
| 4,560,655 | A | 12/1985 | Baker |
| 4,601,978 | A | 7/1986 | Karin |
| 4,657,866 | A | 4/1987 | Kumar |
| 4,665,077 | A | 5/1987 | Stringfellow et al. |
| 4,737,456 | A | 4/1988 | Weng et al. |
| 4,767,704 | A | 8/1988 | Cleveland |
| 4,816,567 | A | 3/1989 | Cabilly et al. |
| 4,927,762 | A | 5/1990 | Darfler |
| 4,948,882 | A | 8/1990 | Ruth |
| 4,965,199 | A | 10/1990 | Capon |
| 4,975,278 | A | 12/1990 | Senter et al. |
| 5,053,394 | A | 10/1991 | Ellestad et al. |
| 5,114,721 | A | 5/1992 | Cohen et al. |
| 5,122,469 | A | 6/1992 | Mather et al. |
| 5,143,844 | A | 9/1992 | Abrahmsen et al. |
| 5,202,238 | A | 4/1993 | Fell, Jr. et al. |
| 5,204,244 | A | 4/1993 | Fell et al. |
| 5,208,020 | A | 5/1993 | Chari et al. |
| 5,264,365 | A | 11/1993 | Georgiou et al. |
| 5,362,852 | A | 11/1994 | Geoghegan |
| 5,416,064 | A | 5/1995 | Chari et al. |
| 5,451,463 | A | 9/1995 | Nelson et al. |
| 5,500,362 | A | 3/1996 | Robinson et al. |
| 5,508,192 | A | 4/1996 | Georgiou et al. |
| 5,519,142 | A | 5/1996 | Hoess et al. |
| 5,541,313 | A | 6/1996 | Ruth |

(Continued)

FOREIGN PATENT DOCUMENTS

| CN | 1173878 A | 2/1998 |
|---|---|---|
| CN | 1176659 A | 3/1998 |

(Continued)

OTHER PUBLICATIONS

Barbin et al. (J. Immunother. Mar.-Apr. 2006; 29 (2): 122-33).*

(Continued)

*Primary Examiner* — Stephen L Rawlings
(74) *Attorney, Agent, or Firm* — Morrison & Foerster LLP

(57) ABSTRACT

The present invention relates to bispecific antibodies, methods for their production, pharmaceutical compositions containing said antibodies, and uses thereof.

11 Claims, 13 Drawing Sheets

Specification includes a Sequence Listing.

(56) References Cited

U.S. PATENT DOCUMENTS

| | | |
|---|---|---|
| 5,532,142 A | 7/1996 | Johnston et al. |
| 5,571,894 A | 11/1996 | Wels et al. |
| 5,574,141 A | 11/1996 | Seliger et al. |
| 5,585,481 A | 12/1996 | Arnold, Jr. et al. |
| 5,587,458 A | 12/1996 | King et al. |
| 5,591,828 A | 1/1997 | Bosslet et al. |
| 5,624,821 A | 4/1997 | Winter et al. |
| 5,635,483 A | 6/1997 | Pettit et al. |
| 5,639,635 A | 6/1997 | Joly et al. |
| 5,641,870 A | 6/1997 | Rinderknecht et al. |
| 5,648,237 A | 7/1997 | Carter et al. |
| 5,648,260 A | 7/1997 | Winter et al. |
| 5,663,149 A | 9/1997 | Pettit et al. |
| 5,712,374 A | 1/1998 | Kuntsmann et al. |
| 5,714,586 A | 2/1998 | Kuntsmann et al. |
| 5,731,168 A | 3/1998 | Carter et al. |
| 5,739,113 A | 4/1998 | Lee |
| 5,739,116 A | 4/1998 | Hamann et al. |
| 5,747,654 A | 5/1998 | Pastan et al. |
| 5,767,285 A | 6/1998 | Hamann et al. |
| 5,770,701 A | 6/1998 | McGahren et al. |
| 5,770,710 A | 6/1998 | McGahren et al. |
| 5,773,001 A | 6/1998 | Hamann et al. |
| 5,780,588 A | 7/1998 | Pettit et al. |
| 5,789,199 A | 8/1998 | Joly et al. |
| 5,798,229 A | 8/1998 | Strittmatter et al. |
| 5,817,786 A | 10/1998 | Ruth |
| 5,821,333 A | 10/1998 | Carter et al. |
| 5,821,337 A | 10/1998 | Carter et al. |
| 5,824,483 A | 10/1998 | Houston |
| 5,840,523 A | 11/1998 | Simmons et al. |
| 5,849,879 A | 12/1998 | Nguyen et al. |
| 5,869,046 A | 2/1999 | Presta et al. |
| 5,877,296 A | 3/1999 | Hamann et al. |
| 5,885,793 A | 3/1999 | Griffiths et al. |
| 5,932,448 A | 8/1999 | Tso et al. |
| 5,959,083 A | 9/1999 | Bosslet et al. |
| 5,959,177 A | 9/1999 | Hein et al. |
| 6,027,888 A | 2/2000 | Georgiou et al. |
| 6,040,498 A | 3/2000 | Stomp et al. |
| 6,083,715 A | 7/2000 | Georgiou et al. |
| 6,136,564 A | 10/2000 | Kopetzki |
| 6,153,190 A | 11/2000 | Young et al. |
| 6,166,185 A | 12/2000 | Davis et al. |
| 6,171,586 B1 | 1/2001 | Lam et al. |
| 6,194,551 B1 | 2/2001 | Idusogie et al. |
| 6,239,259 B1 | 5/2001 | Davis et al. |
| 6,248,516 B1 | 6/2001 | Winter et al. |
| 6,267,958 B1 | 7/2001 | Andya et al. |
| 6,350,860 B1 | 2/2002 | Buyse et al. |
| 6,417,429 B1 | 7/2002 | Hein et al. |
| 6,420,548 B1 | 7/2002 | Vezina et al. |
| 6,511,663 B1 | 1/2003 | King et al. |
| 6,531,581 B1 | 3/2003 | Nardone et al. |
| 6,534,628 B1 | 3/2003 | Nilsson et al. |
| 6,558,672 B1 | 5/2003 | Pastan et al. |
| 6,586,207 B2 | 7/2003 | Tirrell et al. |
| 6,602,684 B1 | 8/2003 | Umana et al. |
| 6,630,579 B2 | 10/2003 | Chari et al. |
| 6,660,843 B1 | 12/2003 | Feige et al. |
| 6,737,056 B1 | 5/2004 | Presta |
| 6,833,441 B2 | 12/2004 | Wang et al. |
| 6,835,809 B1 | 12/2004 | Liu et al. |
| 6,897,044 B1 | 5/2005 | Braslawsky et al. |
| 6,919,426 B2 | 7/2005 | Boone et al. |
| 6,946,292 B2 | 9/2005 | Kanda et al. |
| 6,982,321 B2 | 1/2006 | Winter |
| 7,125,978 B1 | 10/2006 | Vezina et al. |
| 7,129,330 B1 | 10/2006 | Little et al. |
| 7,355,008 B2 | 4/2008 | Stavenhagen et al. |
| 7,381,408 B2 | 6/2008 | Mezo et al. |
| 7,498,298 B2 | 3/2009 | Doronina et al. |
| 7,507,796 B2 | 3/2009 | Little et al. |
| 7,642,228 B2 | 1/2010 | Carter et al. |
| 7,651,688 B2 | 1/2010 | Hanai et al. |
| 7,666,622 B2 | 2/2010 | Sharma et al. |
| 7,695,936 B2 | 4/2010 | Carter et al. |
| 7,919,257 B2 | 4/2011 | Hoogenboom et al. |
| 7,942,042 B2 | 5/2011 | Kawakita et al. |
| 8,216,805 B2 | 7/2012 | Carter et al. |
| 8,227,577 B2 | 7/2012 | Klein et al. |
| 8,242,247 B2* | 8/2012 | Klein et al. ............... 530/387.1 |
| 8,268,314 B2* | 9/2012 | Baehner ................ C07K 16/22 424/136.1 |
| 8,304,713 B2 | 11/2012 | Pradel |
| 8,309,300 B2 | 11/2012 | Jununtula et al. |
| 8,796,424 B2 | 8/2014 | Croasdale et al. |
| 8,871,912 B2* | 10/2014 | Davis ..................... C07K 16/00 530/387.3 |
| 9,382,323 B2* | 7/2016 | Brinkmann ............ C07K 16/00 |
| 9,688,758 B2 | 6/2017 | Wranik et al. |
| 9,708,396 B2* | 7/2017 | Baehner ................ C07K 16/22 |
| 2002/0051986 A1 | 5/2002 | Baez et al. |
| 2002/0155537 A1 | 10/2002 | Carter et al. |
| 2003/0027751 A1 | 2/2003 | Kovesdi et al. |
| 2003/0124129 A1 | 7/2003 | Oliner |
| 2003/0152987 A1 | 8/2003 | Cohen et al. |
| 2003/0157091 A1 | 8/2003 | Hoogenboom |
| 2003/0170230 A1 | 9/2003 | Caterer et al. |
| 2003/0176352 A1 | 9/2003 | Min et al. |
| 2003/0195156 A1 | 10/2003 | Min et al. |
| 2003/0219817 A1 | 11/2003 | Zhu et al. |
| 2003/0229023 A1 | 12/2003 | Oliner et al. |
| 2003/0236193 A1 | 12/2003 | Oliner et al. |
| 2004/0018557 A1 | 1/2004 | Qu et al. |
| 2004/0033561 A1 | 2/2004 | O'Keefe et al. |
| 2004/0038339 A1 | 2/2004 | Kufer et al. |
| 2004/0214988 A1 | 10/2004 | Tirrell et al. |
| 2004/0220388 A1 | 11/2004 | Metens et al. |
| 2004/0224372 A1 | 11/2004 | Li et al. |
| 2005/0054048 A1 | 3/2005 | Grasso et al. |
| 2005/0064509 A1 | 4/2005 | Bradbury et al. |
| 2005/0079170 A1 | 4/2005 | Le Gall et al. |
| 2005/0100543 A1 | 5/2005 | Hansen et al. |
| 2005/0152894 A1 | 7/2005 | Krummen et al. |
| 2005/0163782 A1 | 7/2005 | Glaser et al. |
| 2005/0169933 A1 | 8/2005 | Steeves et al. |
| 2005/0186208 A1 | 8/2005 | Fyfe et al. |
| 2005/0214833 A1 | 9/2005 | Carter et al. |
| 2005/0238649 A1 | 10/2005 | Doronina et al. |
| 2005/0249722 A1 | 11/2005 | Beliard et al. |
| 2005/0260186 A1 | 11/2005 | Bookbinder et al. |
| 2006/0008845 A1 | 1/2006 | Kondejewski et al. |
| 2006/0063921 A1 | 3/2006 | Moulder et al. |
| 2006/0104968 A1 | 5/2006 | Bookbinder et al. |
| 2006/0122370 A1 | 6/2006 | Oliner et al. |
| 2006/0134709 A1 | 6/2006 | Stavenhagen et al. |
| 2006/0160184 A1 | 7/2006 | Mattheus Hoogenboom et al. |
| 2006/0280747 A1 | 12/2006 | Fuh et al. |
| 2007/0014794 A1 | 1/2007 | Carter et al. |
| 2007/0071675 A1 | 3/2007 | Wu et al. |
| 2007/0071742 A1 | 3/2007 | Fang et al. |
| 2007/0141065 A1 | 6/2007 | Fuh et al. |
| 2007/0178552 A1 | 8/2007 | Arathoon et al. |
| 2007/0196274 A1 | 8/2007 | Sun |
| 2007/0269369 A1 | 11/2007 | Gegg et al. |
| 2007/0274985 A1* | 11/2007 | Dubel .................... C07K 16/00 424/133.1 |
| 2007/0274998 A1 | 11/2007 | Uktu |
| 2007/0287170 A1* | 12/2007 | Davis ..................... C07K 16/00 435/69.1 |
| 2008/0044834 A1 | 2/2008 | Heyduk |
| 2008/0063641 A1 | 3/2008 | Huang et al. |
| 2008/0187954 A1 | 8/2008 | Kallmeier et al. |
| 2008/0280778 A1 | 11/2008 | Urdea |
| 2009/0023811 A1 | 1/2009 | Biadatti et al. |
| 2009/0117105 A1 | 5/2009 | Hu et al. |
| 2009/0155275 A1 | 6/2009 | Wu et al. |
| 2009/0162359 A1 | 6/2009 | Klein et al. |
| 2009/0162360 A1 | 6/2009 | Klein et al. |
| 2009/0175851 A1 | 7/2009 | Klein et al. |
| 2009/0194692 A1 | 9/2009 | Kobaru |
| 2009/0232811 A1 | 9/2009 | Klein et al. |
| 2010/0021943 A1 | 1/2010 | An et al. |

(56) References Cited

U.S. PATENT DOCUMENTS

| | | | |
|---|---|---|---|
| 2010/0062436 A1 | 3/2010 | Jarosch et al. | |
| 2010/0081796 A1* | 4/2010 | Brinkmann | C07K 16/2863 530/387.3 |
| 2010/0111967 A1* | 5/2010 | Baehner | C07K 16/22 424/158.1 |
| 2010/0256340 A1 | 7/2010 | Brinkmann et al. | |
| 2010/0254989 A1 | 10/2010 | Bossenmaier et al. | |
| 2010/0256338 A1 | 10/2010 | Brinkmann et al. | |
| 2010/0256339 A1* | 10/2010 | Bossenmaier et al. | 530/387.3 |
| 2010/0266617 A1 | 10/2010 | Carven et al. | |
| 2010/0316645 A1 | 12/2010 | Imhof-Jung et al. | |
| 2010/0322934 A1 | 12/2010 | Imhof-Jung et al. | |
| 2010/0322935 A1 | 12/2010 | Croasdale et al. | |
| 2011/0054151 A1 | 3/2011 | Lazar et al. | |
| 2011/0243966 A1 | 10/2011 | Farrington et al. | |
| 2012/0029481 A1 | 2/2012 | Pech et al. | |
| 2012/0149879 A1* | 6/2012 | Brinkmann et al. | 530/387.3 |
| 2012/0164726 A1 | 6/2012 | Klein et al. | |
| 2012/0184718 A1 | 7/2012 | Bruenker et al. | |
| 2012/0225071 A1 | 9/2012 | Klein et al. | |
| 2012/0237506 A1 | 9/2012 | Bossenmaier et al. | |
| 2012/0237507 A1 | 9/2012 | Bossenmaier et al. | |
| 2012/0302737 A1 | 11/2012 | Christensen et al. | |
| 2012/0321627 A1* | 12/2012 | Baehner | C07K 16/22 424/136.1 |
| 2013/0022601 A1 | 1/2013 | Brinkmann et al. | |
| 2013/0058937 A1 | 3/2013 | Auer et al. | |
| 2013/0060011 A1 | 3/2013 | Bruenker et al. | |
| 2013/0078249 A1 | 3/2013 | Ast et al. | |
| 2013/0156772 A1 | 6/2013 | Bossenmaier et al. | |
| 2013/0266568 A1 | 10/2013 | Brinkmann et al. | |
| 2013/0267686 A1 | 10/2013 | Brinkmann et al. | |
| 2013/0273054 A1 | 10/2013 | Bossenmaier et al. | |
| 2013/0288267 A1 | 10/2013 | Gerg et al. | |
| 2013/0344094 A1 | 12/2013 | Gerg et al. | |
| 2014/0249296 A1 | 9/2014 | Ploegh | |
| 2014/0294810 A1 | 10/2014 | Lowman et al. | |
| 2015/0004166 A1* | 1/2015 | Baehner | C07K 16/22 424/136.1 |
| 2015/0030598 A1 | 1/2015 | Croasdale et al. | |
| 2015/0133638 A1 | 5/2015 | Wranik et al. | |
| 2015/0232541 A1 | 8/2015 | Fenn et al. | |
| 2015/0232560 A1 | 8/2015 | Heindl et al. | |
| 2015/0232561 A1 | 8/2015 | Fenn et al. | |
| 2015/0291704 A1 | 10/2015 | Beck | |
| 2016/0002356 A1 | 1/2016 | Christensent et al. | |

FOREIGN PATENT DOCUMENTS

| | | |
|---|---|---|
| CN | 1232039 A | 10/1999 |
| CN | 1603345 A | 4/2005 |
| CN | 101037671 A | 9/2007 |
| CN | 101052653 A | 10/2007 |
| CN | 101065151 A | 10/2007 |
| CN | 101205255 A | 6/2008 |
| CN | 101218251 A | 7/2008 |
| CN | 101355966 A | 1/2009 |
| EP | 0 292 128 A1 | 11/1988 |
| EP | 0 307 434 B1 | 3/1989 |
| EP | 0 307 434 B2 | 3/1989 |
| EP | 0 313 219 A2 | 4/1989 |
| EP | 0 339 217 B1 | 11/1989 |
| EP | 0 340 109 A2 | 11/1989 |
| EP | 0 404 097 B1 | 12/1990 |
| EP | 0 423 839 A2 | 4/1991 |
| EP | 0 425 235 B1 | 5/1991 |
| EP | 0 523 978 A1 | 1/1993 |
| EP | 0 618 192 A1 | 10/1994 |
| EP | 0 637 593 A1 | 2/1995 |
| EP | 0 786 468 A2 | 7/1997 |
| EP | 1 074 563 A1 | 2/2001 |
| EP | 1 186 613 A1 | 3/2002 |
| EP | 1 391 213 A1 | 2/2004 |
| EP | 1 431 298 A1 | 6/2004 |
| EP | 1 538 221 A1 | 6/2005 |
| EP | 1 870 459 A1 | 12/2007 |
| EP | 2 050 764 A1 | 4/2009 |
| EP | 2 443 154 B1 | 4/2012 |
| JP | 7-501698 A | 2/1995 |
| JP | 2008-518605 A | 6/2008 |
| JP | 2008-531049 A | 8/2008 |
| RU | 2005/124281 A | 1/2006 |
| RU | 2295537 C2 | 3/2007 |
| WO | WO-87/00195 A1 | 1/1987 |
| WO | WO-1989/02439 A1 | 3/1989 |
| WO | WO-1989/02931 A1 | 4/1989 |
| WO | WO-1989/12642 A1 | 12/1989 |
| WO | WO-90/03430 A1 | 4/1990 |
| WO | WO-90/08187 A1 | 7/1990 |
| WO | WO-1990/08156 A1 | 7/1990 |
| WO | WO-90/11294 A1 | 10/1990 |
| WO | WO-91/01133 A1 | 2/1991 |
| WO | 91/06305 | 5/1991 |
| WO | WO-1992/01047 A1 | 1/1992 |
| WO | 92/04053 | 3/1992 |
| WO | WO-1992/11388 | 7/1992 |
| WO | WO-1993/01161 A1 | 1/1993 |
| WO | WO-1993/05060 A1 | 3/1993 |
| WO | WO-93/06217 A1 | 4/1993 |
| WO | WO-93/11161 A1 | 6/1993 |
| WO | WO-93/11162 A1 | 6/1993 |
| WO | WO-1993/16185 A2 | 8/1993 |
| WO | WO-1993/16185 A3 | 8/1993 |
| WO | WO-93/21232 A1 | 10/1993 |
| WO | WO-1994/04550 A1 | 3/1994 |
| WO | WO-94/09131 A1 | 4/1994 |
| WO | WO-94/10202 A1 | 5/1994 |
| WO | WO-94/11026 A2 | 5/1994 |
| WO | WO-1994/10308 A1 | 5/1994 |
| WO | WO-94/29350 A2 | 12/1994 |
| WO | WO-94/29350 A3 | 12/1994 |
| WO | WO-1995/05399 A1 | 2/1995 |
| WO | 95/09917 | 4/1995 |
| WO | WO-1995/17886 A1 | 7/1995 |
| WO | WO-96/27011 A1 | 9/1996 |
| WO | WO-96/27612 A1 | 9/1996 |
| WO | 97/01580 | 1/1997 |
| WO | WO-1997/05156 A1 | 2/1997 |
| WO | WO-97/014719 A1 | 4/1997 |
| WO | WO-97/028267 A1 | 8/1997 |
| WO | WO-97/028267 C1 | 8/1997 |
| WO | WO-1997/43451 A1 | 11/1997 |
| WO | WO-98/45331 A2 | 10/1998 |
| WO | WO-98/45331 A3 | 10/1998 |
| WO | WO-98/45332 A2 | 10/1998 |
| WO | WO-98/45332 A3 | 10/1998 |
| WO | WO-1998/48032 A2 | 10/1998 |
| WO | WO-1998/48032 A3 | 10/1998 |
| WO | WO-98/050431 A2 | 11/1998 |
| WO | WO-1999/06587 A2 | 2/1999 |
| WO | WO-1999/06587 A3 | 2/1999 |
| WO | WO-99/37791 A1 | 7/1999 |
| WO | WO-99/54342 A1 | 10/1999 |
| WO | WO-1999/51642 A1 | 10/1999 |
| WO | WO-99/66951 A2 | 12/1999 |
| WO | WO-99/66951 A3 | 12/1999 |
| WO | WO-99/66951 C1 | 12/1999 |
| WO | WO-00/24770 A2 | 5/2000 |
| WO | WO-00/24770 A3 | 5/2000 |
| WO | WO-00/29004 A1 | 5/2000 |
| WO | WO-00/35956 A | 6/2000 |
| WO | WO-00/61739 A1 | 10/2000 |
| WO | WO 2001/042505 A2 | 6/2001 |
| WO | WO 2001/042505 A3 | 6/2001 |
| WO | 2001/077342 | 10/2001 |
| WO | WO-01/90192 A2 | 11/2001 |
| WO | WO-2001/085795 A1 | 11/2001 |
| WO | WO-02/02781 A1 | 1/2002 |
| WO | WO-02/051870 A2 | 7/2002 |
| WO | WO-2002/072141 A2 | 9/2002 |
| WO | WO-2002/072141 A3 | 9/2002 |
| WO | WO-02/088172 A2 | 11/2002 |
| WO | WO-02/092620 A2 | 11/2002 |

(56) References Cited

FOREIGN PATENT DOCUMENTS

| | | |
|---|---|---|
| WO | WO-02/092620 A3 | 11/2002 |
| WO | WO-2002/096948 A2 | 12/2002 |
| WO | WO-03/012069 A2 | 2/2003 |
| WO | WO-2003/019145 A2 | 3/2003 |
| WO | WO-2003/019145 A3 | 3/2003 |
| WO | WO-03/030833 A2 | 4/2003 |
| WO | WO-03/030833 A3 | 4/2003 |
| WO | WO-03/031589 A2 | 4/2003 |
| WO | WO-03/031589 A3 | 4/2003 |
| WO | WO-03/035694 A2 | 5/2003 |
| WO | WO-03/035835 A2 | 5/2003 |
| WO | WO-03/035835 A3 | 5/2003 |
| WO | WO-03/055993 A1 | 7/2003 |
| WO | WO-03/057134 A2 | 7/2003 |
| WO | WO-03/057134 A3 | 7/2003 |
| WO | WO-03/066660 A2 | 8/2003 |
| WO | WO-2003/073238 A2 | 9/2003 |
| WO | WO-2003/073238 A3 | 9/2003 |
| WO | WO-03/097105 A1 | 11/2003 |
| WO | WO-03/106501 A1 | 12/2003 |
| WO | WO 2003/104249 A1 | 12/2003 |
| WO | WO-2004/032961 A1 | 4/2004 |
| WO | WO-2004/058298 A1 | 7/2004 |
| WO | WO 2004/062602 A2 | 7/2004 |
| WO | WO 2004/062602 A3 | 7/2004 |
| WO | 2004/065417 A2 | 8/2004 |
| WO | WO-2004/065540 A2 | 8/2004 |
| WO | WO-2004/065540 A3 | 8/2004 |
| WO | WO-2004/072117 A2 | 8/2004 |
| WO | WO-2004/072117 A3 | 8/2004 |
| WO | WO 2004/081051 A1 | 9/2004 |
| WO | WO-2004/092215 A2 | 10/2004 |
| WO | WO-2004/092215 A3 | 10/2004 |
| WO | 2005/005635 A2 | 1/2005 |
| WO | WO-2005/000900 A1 | 1/2005 |
| WO | WO-2005/001025 A2 | 1/2005 |
| WO | WO-2005/001025 A3 | 1/2005 |
| WO | WO-2005/004809 A2 | 1/2005 |
| WO | WO-2005/004809 A3 | 1/2005 |
| WO | WO-2005/011735 A1 | 2/2005 |
| WO | WO-2005/018572 A2 | 3/2005 |
| WO | WO-2005/018572 A3 | 3/2005 |
| WO | WO-2005/027966 A2 | 3/2005 |
| WO | WO-2005/027966 A3 | 3/2005 |
| WO | WO-2005/035572 A2 | 4/2005 |
| WO | WO-2005/035572 A3 | 4/2005 |
| WO | WO-2005/035727 A2 | 4/2005 |
| WO | WO-2005/035727 A3 | 4/2005 |
| WO | WO-2005/044853 A2 | 5/2005 |
| WO | WO-2005/044853 A3 | 5/2005 |
| WO | WO-2005/044859 A2 | 5/2005 |
| WO | WO-2005/044859 A3 | 5/2005 |
| WO | WO-2005/051976 A2 | 6/2005 |
| WO | WO-2005/063816 A2 | 7/2005 |
| WO | WO-2005/063816 A3 | 7/2005 |
| WO | WO-2005/074524 A2 | 8/2005 |
| WO | WO-2005/075514 A2 | 8/2005 |
| WO | 2006/020258 | 2/2006 |
| WO | WO-2006/020258 A2 | 2/2006 |
| WO | WO-2006/020258 A3 | 2/2006 |
| WO | WO-2006/028956 A2 | 3/2006 |
| WO | WO-2006/028956 A3 | 3/2006 |
| WO | WO-2006/031370 A2 | 3/2006 |
| WO | WO-2006/031370 A3 | 3/2006 |
| WO | WO-2006/034488 A2 | 3/2006 |
| WO | WO-2006/034488 A3 | 3/2006 |
| WO | WO-2006/044908 A2 | 4/2006 |
| WO | WO-2006/044908 A3 | 4/2006 |
| WO | WO-2006/045049 A1 | 4/2006 |
| WO | WO-2006/068953 A2 | 6/2006 |
| WO | WO-2006/068953 A3 | 6/2006 |
| WO | 2006/082515 A2 | 8/2006 |
| WO | WO-2006/089364 A1 | 8/2006 |
| WO | WO-2006/093794 A1 | 8/2006 |
| WO | WO-2006/103100 A2 | 10/2006 |
| WO | WO-2006/103100 A3 | 10/2006 |
| WO | WO-2006/113665 A2 | 10/2006 |
| WO | WO-2006/114700 A2 | 11/2006 |
| WO | WO-2006/114700 A3 | 11/2006 |
| WO | WO-2006/116260 A2 | 11/2006 |
| WO | WO-2006/116260 A3 | 11/2006 |
| WO | WO 2006/137932 A2 | 12/2006 |
| WO | WO 2006/137932 A3 | 12/2006 |
| WO | 2007/024715 | 3/2007 |
| WO | WO-2007/024715 A2 | 3/2007 |
| WO | WO-2007/031875 A2 | 3/2007 |
| WO | WO-2007/031875 A3 | 3/2007 |
| WO | WO 2007/038658 A2 | 4/2007 |
| WO | WO 2007/038658 A3 | 4/2007 |
| WO | WO-2007/044887 A2 | 4/2007 |
| WO | WO-2007/044887 A3 | 4/2007 |
| WO | WO-2007/048037 A2 | 4/2007 |
| WO | WO-2007/048037 A3 | 4/2007 |
| WO | WO 2007/059816 A1 | 5/2007 |
| WO | WO-2007/068895 A1 | 6/2007 |
| WO | WO 2007/069092 A2 | 6/2007 |
| WO | WO 2007/069092 A3 | 6/2007 |
| WO | WO-2007/084181 A2 | 7/2007 |
| WO | WO-2007/084181 A3 | 7/2007 |
| WO | WO-2007/035837 A1 | 8/2007 |
| WO | WO-2007/089445 A2 | 8/2007 |
| WO | WO-2007/089445 A3 | 8/2007 |
| WO | WO-2007/095338 A2 | 8/2007 |
| WO | 2007/109254 | 9/2007 |
| WO | WO-2007/108013 A2 | 9/2007 |
| WO | 2007/110205 | 10/2007 |
| WO | WO-2007/147901 A1 | 12/2007 |
| WO | WO-2008/005828 A2 | 1/2008 |
| WO | WO-2008/005828 A3 | 1/2008 |
| WO | 2008/017963 | 2/2008 |
| WO | WO-2008/077077 A2 | 6/2008 |
| WO | WO-2008/077077 A3 | 6/2008 |
| WO | 2008/077546 | 7/2008 |
| WO | WO-2008/077546 A1 | 7/2008 |
| WO | WO-2008/100624 A2 | 8/2008 |
| WO | WO-2008/100624 A3 | 8/2008 |
| WO | WO-2008/132568 A2 | 11/2008 |
| WO | WO-2008/132568 A3 | 11/2008 |
| WO | WO-2009/007124 A1 | 1/2009 |
| WO | WO-2009/018386 A1 | 2/2009 |
| WO | WO-2009/021745 A1 | 2/2009 |
| WO | WO-2009/021754 A2 | 2/2009 |
| WO | WO-2009/021754 A3 | 2/2009 |
| WO | WO-2009/023843 A1 | 2/2009 |
| WO | WO-2009/032782 A2 | 3/2009 |
| WO | WO-2009/032782 A3 | 3/2009 |
| WO | WO 2009/037659 A2 | 3/2009 |
| WO | WO 2009/037659 A3 | 3/2009 |
| WO | WO 2009/059278 A1 | 5/2009 |
| WO | 2009/080253 A1 | 7/2009 |
| WO | WO-2009/080251 A1 | 7/2009 |
| WO | WO-2009/080252 A1 | 7/2009 |
| WO | WO-2009/080254 A1 | 7/2009 |
| WO | WO-2009/089004 A1 | 7/2009 |
| WO | WO 2009/105671 A2 | 8/2009 |
| WO | WO 2009/105671 A3 | 8/2009 |
| WO | WO-2009/126944 A1 | 10/2009 |
| WO | 2010/034441 | 4/2010 |
| WO | 2010/040508 A1 | 4/2010 |
| WO | WO-2010/040508 A1 | 4/2010 |
| WO | WO-2010/040508 A8 | 4/2010 |
| WO | WO-2010/040508 A9 | 4/2010 |
| WO | WO-2010/045193 A1 | 4/2010 |
| WO | WO-2010/065882 A1 | 6/2010 |
| WO | WO-2010/087994 A2 | 8/2010 |
| WO | 2010/112193 | 10/2010 |
| WO | WO-2010/112193 A1 | 10/2010 |
| WO | WO-2010/112194 A1 | 10/2010 |
| WO | WO-2010/115552 A1 | 10/2010 |
| WO | WO-2010/115589 A1 | 10/2010 |
| WO | WO-2010/115589 A8 | 10/2010 |
| WO | WO-2010/115598 A1 | 10/2010 |
| WO | WO 2010/118169 A2 | 10/2010 |
| WO | WO 2010/118169 A3 | 10/2010 |

(56) References Cited

FOREIGN PATENT DOCUMENTS

| | | |
|---|---|---|
| WO | WO-2010/129304 A2 | 11/2010 |
| WO | WO-2010/129304 A3 | 11/2010 |
| WO | WO-2010/136172 A1 | 12/2010 |
| WO | WO-2010/145792 A1 | 12/2010 |
| WO | WO-2010/145793 A1 | 12/2010 |
| WO | WO-2011/003557 A1 | 1/2011 |
| WO | WO-2011/028952 A1 | 3/2011 |
| WO | WO-2011/034605 A2 | 3/2011 |
| WO | WO-2011/034605 A3 | 3/2011 |
| WO | WO-2011/090754 A1 | 7/2011 |
| WO | WO-2011/090762 A1 | 7/2011 |
| WO | WO-2011/133886 A2 | 10/2011 |
| WO | WO-2011/143545 A1 | 11/2011 |
| WO | WO-2012/006633 A1 | 1/2012 |
| WO | WO-2012/025525 A1 | 3/2012 |
| WO | WO-2012/025530 A1 | 3/2012 |
| WO | WO-2012/058768 A1 | 5/2012 |
| WO | WO-2012/085069 A2 | 6/2012 |
| WO | WO-2012/085069 A3 | 6/2012 |
| WO | WO-2012/085111 A1 | 6/2012 |
| WO | WO-2012/085113 A1 | 6/2012 |
| WO | WO-2012/116927 A1 | 9/2012 |
| WO | WO-2013/003555 A1 | 1/2013 |
| WO | WO-2013/006544 A1 | 1/2013 |
| WO | WO-2013/006544 A8 | 1/2013 |
| WO | WO-2013/026833 A1 | 2/2013 |
| WO | 2010/069532 A1 | 6/2013 |
| WO | WO-2013/092716 A1 | 6/2013 |
| WO | WO-2013/096291 A2 | 6/2013 |
| WO | WO-2013/096291 A3 | 6/2013 |
| WO | WO-2013/119966 | 8/2013 |
| WO | WO-2013/157953 A1 | 10/2013 |
| WO | WO-2013/157954 A1 | 10/2013 |
| WO | WO-2013/174873 A1 | 11/2013 |
| WO | WO-2014/001326 A1 | 1/2014 |
| WO | WO-2014/012085 A2 | 1/2014 |
| WO | WO-2014/049003 A1 | 4/2014 |
| WO | WO-2014/144357 A1 | 9/2014 |
| WO | WO-2016/087416 A1 | 6/2016 |

OTHER PUBLICATIONS

Walker et al. (J. Mol. Biol. Jun. 5, 2009; 389 (2): 365-75).*
Hust et al. (BMC Biotechnology 2007, 7: 14; pp. 1-15).*
Lu et al. (J. Immunol. Methods. Sep. 15, 2002; 267 (2): 213-26).*
Koerber et al. (J. Mol. Biol. Jan. 30, 2015; 427 (2): 576-86).*
Mabry et al. (Protein Eng. Des. Sel. Mar. 2010; 23 (3): 115-27).*
Michaelson et al. (MAbs. Mar.-Apr. 2009; 1 (2): 128-41).*
Kontermann (Curr. Opin. Mol. Ther. Apr. 2010; 12 (2): 176-83).*
Schanzer et al. (J. Biol. Chem. Jul. 4, 2014; 289 (27): 18693-706).*
Coloma and Morrison, "Design and production of novel tetravalent bispecific antibodies" Nat Biotechnol 15(2):159-163 (Feb. 1997).
Fischer and Leger, "Bispecific antibodies: Molecules that enable novel therapeutic strategies" Pathobiology 74:3-14 ( 2007).
Holliger et al., "Engineered antibody fragments and the rise of single domains" Nat Biotechnol 23(9):1126-36 (Sep. 2005).
Hust et al., "Single chain Fab (scFab) fragment" BMC Biotechnology 7:1-15 ( 2007).
International Preliminary Report on Patentability for PCT/EP2011/054505 (dated Oct. 2, 2012).
Lee et al., "Generation and characterization of a novel single-gene-encoded single-chain immunoglobulin molecule with antigen binding activity and effector functions" Mol Immunol. 36(1):61-71 (1999).
Lu et al., "A fully human recombinant IgG-like bispecific antibody to both the epidermal growth factor receptor and the insulin-like growth factor receptor for enhanced antitumor activity" J. Biol. Chem. 280(20):19665-72 ( 2005).
Lu et al., "Fab-scFv fusion protein: an efficient approach to production of bispecific antibody fragments" J Immunol Methods 267(2):213-26 (2002).

Lu et al., "Simultaneous blockade of both the epidermal growth factor receptor and the insulin-like growth factor receptor signaling pathways in cancer cells with a fully human recombinant bispecific antibody" J. Biol. Chem. 279(4):2856-65 ( 2004).
Lu et al., "The effect of variable domain orientation and arrangement on the antigen-binding activity of a recombinant human bispecific diabody" Biochem Biophys Res Commun. 18(2):507-13 ( 2004).
Morrison, "Two Heads are Better than One" Nat Biotechnol 25(11):1233-34 (Nov. 2007).
Müller D. and R.E. Kontermann, Handbook of Therapeutic Antibodies, Bispecific Antibodies "2 Bispecific Antibodies" (ISBN 978-3-527-31453-9), Wiley-VCH Verlag, Weinheim,:345-378 ( 2007).
Ridgway et al., "'Knobs-into-holes' Engineering of Antibody CH3 Domains for Heavy Chain Heterodimerization" Protein Eng 9(7):617-621 ( 1996).
Schirrmann et al., "Oligomeric forms of single chain immunoglobulin (scIgG)" Landes Bioscience 2(1):73-6 ( 2010).
Schoonjans et al., "Efficient heterodimerization of recombinant bi- and trispecific antibodies" Bioseparation 9(3):179-83 ( 2000).
Shen et al., "Single variable domain antibody as a versatile building block for the construction of IgG-like bispecific antibodies" J Immunol Methods 318:65-74 ( 2007).
Written Opinion for PCT/EP2011/054505 (dated Jun. 28, 2011).
Wu et al., "Simultaneous Targeting of Multiple Disease Mediators by a Dual-Variable-Domain Immunoglobulin" Nature Biotech. 25:1290-1297 ( 2007).
Xie et al., "A new format of bispecific antibody: highly efficient heterodimerization, expression and tumor cell lysis" Journal of Immunological Methods 296:95-101 ( 2005).
Aggarwal et al. "Fibroblast Activation Protein Peptide Substrates Identified from Human Collagen I Derived Gelatin Cleavage Sites," *Biochemistry* 47(3):1076-1086, (Jan. 22, 2008).
Anonymous. "Production in yeasts of stable antibody fragments," *Expert Opinion on Therapeutic Patents* 7(2):179-183, (1997).
Arié et al. "Chaperone Function of FkpA, a Heat Shock Prolyl Isomerase, in the Periplasm of *Escherichia coli,*" *Mol. Microbiol.* 39(1):199-210, (2001).
Arndt et al. "Helix-stabilized Fv (hsFv) antibody fragments: substituting the constant domains of a Fab fragment for a heterodimeric coiled-coil domain," *J. Mol. Biology* 312(1):221-228, (Sep. 7, 2001).
Arndt et al. "Factors influencing the dimer to monomer transition of an antibody single-chain Fv fragment," *Biochemistry*, 37(37):12918-26, (1998).
Atwell et al. "Stable heterodimers from remodeling the domain interface of a homodimer using a phage display library," *J. Mol. Biol.* 270 (1):26-35 (1997).
Ausubel et al. Short Protocols in Molecular Biology, Greene Publishing and Wiley Interscience, New York, New York, (Table of Contents), (1987).
Avgeris et al. "Kallikrein-related peptidase genes as promising biomarkers for prognosis and monitoring of human malignancies," *Biol. Chem.* 391(5):505-511, (May 2010).
Bachman. "Derivations and Genotypes of Some Mutant Derivatives of *Escherichia coli* K-12," Chapter 72 in *Escherichia Coli and Samonella Typimurium Cellular and Molecular Biology*, vol. 2, American Society for Microbiology, Washington D.C., pp. 1190-1219, (1987).
Baldwin et al. "Monoclonal Antibodies in Cancer Treatment," *Lancet* 60:603-606, (1986).
Barnes et al. "Methods for Growth of Cultured Cells in Serum-free Medium," *Anal. Biochem.* 102:255-270, (Mar. 1, 1980).
Barnes et al. "Advances in animal cell recombinant protein production: GS-NS0 expression system," *Cytotechnology* 32 (2):109-23 (Feb. 2000).
Barnes et al. "Characterization of the stability of recombinant protein production in the GS-NS0 expression system," *Biotechnol Bioeng.* 73(4):261-70 (May 2001).
Bass et al. "Hormone Phage: An Enrichment Method for Variant Proteins With Altered Binding Properties," *Proteins* 8:309-314, (1990).

(56) References Cited

OTHER PUBLICATIONS

Bera et al. "A bivalent disulfide-stabilized Fv with improved antigen binding to erbB2," *J. Mol. Biol.* 281(3):475-483, (Aug. 21, 1998).
Bird et al. "Single-Chain Antigen-Binding Proteins," *Science* 242(4877):423-6, (Oct. 21, 1988).
Bird et al. "Single-Chain Antigen-Binding Proteins," *Science* 244(4903):409, *Erratum*, (Apr. 28, 1989).
Boado et al. "IgG-single chain Fv fusion protein therapeutic for Alzheimer's disease: Expression in CHO cells and pharmacokinetics and brain delivery in the rhesus monkey," *Biotechnology and Bioengineering* 105(3):627-635, (Feb. 15, 2010).
Boerner et al. "Production of Antigen—Specific Human Monoclonal Antibodies From in Vitro-Primed Human Splenocytes," *J. Immunol.* 147(1):86-95, (Jul. 1991).
Booy et al. "Monoclonal and Bispecific Antibodies as Novel Therapeutics," *Arch. Immunol. Ther. Exp.* 54:85-101, (Mar.-Apr. 2006, e-pub. Mar. 24, 2006).
Borgström et al. "Complete Inhibition of Angiogenesis and Growth of Microtumors by Anti-Vascular Endothelial Growth Factor Neutralizing Antibody: Novel Concepts of Angiostatic Therapy from Intravital Videomicroscopy," *Cancer Research* 56:4032-4039, (1996).
Bothmann et al. "The Periplasmic *Escherichia coli* Peptidylprolyl cis,trans-Isomerase FkpA. I. Increased Functional Expression of Antibody Fragments With and Without cis-Prolines," *J. Biol. Chem.* 275(22):17100-17105, (Jun. 2, 2000).
Briggs et al. "Cystatin E/M suppresses legumain activity and invasion of human melanoma," *BMC Cancer* 10(17):1-13, (Jan. 2010).
Brinkmann. "Disulfide-stabilized Fv fragments," Chapter 14 in 2 in Antibody Engineering, Kontermann et al. eds., vol. 2, Springer-Verlag, Berlin Heidelberg, Germany, pp. 181-189, (Apr. 30, 2010).
Brinkmann et al. "A recombinant immunotoxin containing a disulfide-stabilized Fv fragment," *PNAS* 90(16):7538-7542, (1993).
Brorson et al. "Mutational Analysis of Avidity and Fine Specificity of Anti-Levan Antibodies," *J. Immunol.* 163:6694-6701 (1994).
Brüggemann et al., "Comparison of the effector functions of human immunoglobulins using a matched set of chimeric antibodies," *J Exp Med.* 166(5):1351-61, (Nov. 1987).
Brüggemann et al. "Designer Mice: The Production of Human Antibody Repertoires in Transgenic Animals," *Year in Immuno.* 7:33-40, (1993).
Brummell et al. "Probing the combining site of an anti-carbohydrate antibody by saturation-mutagenesis: role of the heavy-chain CDR3 residues," *Biochemistry* 32(4):1180-1187 (1993).
Brunhouse et al. "Isotypes of IgG: comparison of the primary structures of three pairs of isotypes which differ in their ability to activate complement," *Mol Immunol.* 16(11): 907-917, (Nov. 1979).
Budtschanow et al. "System of Humoral Immunity Antibodies (Theme 2)," Guidance Manual for General Immunology, Twer (2008) p. 3, English Translation, 3 pages, (5 pages of both English Equivalent and Russian Reference).
Burgess et al. "Possible dissociation of the heparin-binding and mitogenic activities of heparin-binding (acidic fibroblast growth factor-1 from its receptor-binding activities by site-directed mutagenesis of a single lysine residue," *Journal of Cell Biology* 111:2129-2138, (Nov. 1990).
Burks et al. "In vitro scanning saturation mutagenesis of an antibody binding pocket," *PNAS* 94(2):412-417, (1997).
Burton et al. "The C1q Receptor Site on Immunoglobulin G," *Nature* 288(5789):338-344, (Nov. 27, 1980).
Burton. "Immunoglobulin G: Functional Sites," *Molec. Immunol.* 22(3):161-206, (1985).
Cao et al. "Bispecific Antibody Conjugates in Therapeutics," *Advanced Drug Delivery Reviews* 55:171-197, (2003).
Capel et al. "Heterogenity of Human IgG Fc Receptors," *Immunomethods* 4:25-34, (1994).
Carlsson et al. "Protein Thiolation and Reversible Protein-Protein Conjugation. N-Succinimidyl 3-(2-pyridyldithio)propionate, a New Heterobifunctional Reagent," *Biochem. J.* 173:723-737, (Sep. 1, 1978).

Caron et al. "Engineered humanized dimeric forms of IgG are more effective antibodies," *J. Exp. Med.* 176(4):1191-1195, (Oct. 1, 1992).
Carro et al. "Serum insulin-like growth factor I regulates brain amyloid-β levels," *Nature Medicine* 8(12):1390-1397, (2002, e-pub. Nov. 4, 2002).
Carter et al. "Humanization of an Anti-P185$^{HER2}$ Antibody for Human Cancer Therapy," *Proc Natl Acad Sci USA.* 89(10): 4285-4289 (May 1992).
Carter. "Bispecific human IgG by design," *Immunol. Methods* 248:7-15, (2001).
Chan et al. "Variable Region Domain Exchange in Human IgGs Promotes Antibody Complex Formulation with Accompanying Structural Changes and Altered Effector Functions," *Molecular Immunology* 41(5):527-538, (2004).
Chang et al. "A General Method for Facilitating Heterodimeric Pairing Between Two Proteins: Application to Expression of a and p T-cell Receptor Extracellular Segments," *Proc. Nat'l Acad. Sci.* 91:11408-12, (Nov. 1994).
Chari et al. "Immunoconjugates Containing Novel Maytansinoids: Promising Anticancer Drugs," *Cancer Research* 52:127-131, (Jan. 1, 1992).
Chen et al. "Selection and Analysis of an Optimized Anti-VEGF Antibody: Crystal Structure of an Affinity-matured Fab in Complex With Antigen," *J. Mol. Biol.* 293(4):865-881, (Nov. 5, 1999).
Chen et al. "Chaperone Activity of DsbC," *J. Biol. Chem* 274(28):19601-19605, (Jul. 9, 1999).
Chernaia, "[Cathepsin L from human brain tumor. Purification and contents]." Ukr Biokhim Zh. 70(5):97-103, (Sep.-Oct. 1998). (English Translation of Abstract.) (Article in Russian).
Chitnis et al. "The type 1 insulin-like growth factor receptor pathway," *Clin. Cancer Res.* 14(20):6364-6370, (Oct. 16, 2008).
Chothia et al. "Canonical Structures for the Hypervariable Regions of Immunoglobulins," *J. Mol. Biol.* 196:901-917, (1987).
Chow et al. "Studies on the Subsite Specificity of Rat Nardilysin (N-Arginine Dibasic Convertase)," *J. Biol. Chem.* 275(26):19545-19551, (Jun. 30, 2000).
Chung et al., "Development of a novel albumin-binding prodrug that is cleaved by urokinase-type-plasminogen activator (uPA)," *Bioorg Med Chem Lett.* 16(19):5157-5163 (Oct. 1, 2006).
Clynes et al. "Fc Receptors are Required in Passive and Active Immunity to Melanoma," *Proc. Natl. Acad. Sci. USA* 95:652-656, (Jan. 1998).
Cohen et al. "Nonchromosomal antibiotic resistance in bacteria: Genetic transformation of *Escherichia coli* by R-factor DNA," *Proc. Natl. Acad. Sci. USA* 69(8):2110-2114, (Aug. 1972).
Cole et al. "The EBV-hybridoma technique and its application to human lung cancer," *Monoclonal Antibodies and Cancer Therapy*, New York: Alan R. Liss, Inc. pp. 77-96, (1985).
Coleman. "Effects of amino acid sequence changes on antibody-antigen interactions," *Research in Immunol.* 145(1):33-36, (1994).
Cordingley et al. "Substrate requirements of human rhinovirus 3C protease for peptide cleavage in vitro," *J. Biol. Chem.* 265(16):9062-9065, (1990).
Cortesio et al. "Calpain 2 and PTP1B function in a novel pathway with Src to regulate invadopodia dynamics and breast cancer cell invasion," *J. Cell Biol.* 180(5):957-971, (Mar. 10, 2008).
Coxon et al. "Combined treatment of angiopoietin and VEGF pathway antagonists enhances antitumor activity in preclinical models of colon carcinoma," *99th AACR Annual Meeting*, Abstract #1113, (Apr. 2008).
Crawford et al. "Matrix metalloproteinase-7 is expressed by pancreatic cancer precursors and regulates acinar-to-ductal metaplasia in exocrine pancreas," *J. Clin. Invest.* 109(11):1437-1444, (Jun. 2002).
Cudic et al. "Extracellular proteases as targets for drug development," *Curr. Protein Pept Sci* 10(4):297-307, (Aug. 2009).
Cullen et al. "Granzymes in cancer and immunity," *Cell Death Differ* 17(4):616-623, (Apr. 2010).
Daëron. "Fc Receptor Biology," *Annu. Rev. Immunol.* 15:203-234, (1997).

(56) References Cited

OTHER PUBLICATIONS

Dall'Acqua et al. "Contribution of Domain Interface Residues to the Stability of Antibody CH3 Domain Homodimers", *Biochemistry*, 37:9266-9273, (1998).
Davies et al. "'Camelising' Human Antibody Fragments: NMR Studies on VH Domains," *Febs Letter* 339:285-290, (1994).
Davies et al. "Expression of GnTIII in a recombinant anti-CD20 CHO production cell line: Expression of antibodies with altered glycoforms leads to an increase in ADCC through higher affinity for FcγRIII," *Biotechnol. Bioeng.* 74:288-294, (2001).
Davis et al. "SEEDbodies: Fusion Proteins Based on Strand-Exchange Engineered Domain (SEED) $C_H3$ Heterodimers in an Fc Analogue Platform for Asymmetric Binders or Immunofusions and Bispecific Antibodies," *Protein Engineering Design & Selection* 23(4):195-202, (2010, e-pub. Feb. 4, 2010).
De Haas et al. "Fcγ Receptors of Phagocytes," *J. Lab. Clin. Med.* 126:330-341, (Oct. 1995).
Deyev. "Multivalency: the hallmark of antibodies used for optimization of tumor targeting by design," *Bioessays* 30(9):904-918, (2008).
Deyev et al. "Modern Technologies for Creating synthetic Antibodies for clinical Application," Acta Naturae 1:32-50, (2009).
Dimmock et al. "Valency of antibody binding to virions and its determination by surface plasmon resonance", *Rev. Med. Virol.*, 14:123-135, (2004).
Donaldson et al. "Design and development of masked therapeutic antibodies to limit off-target effects: Application to anti-EGFR antibodies," *Cancer Biology & Therapy* 8(22):2145-2150, (Nov. 15, 2009).
Dooley et al. "Antibody Repertoire Development in Cartilaginous Fish," *Dev. Comp. Immunol.* 30(1-2):43-56, (2006).
Doronina et al. "Development of Potent Monoclonal Antibody Auristatin Conjugates for Cancer Therapy," *Nat. Biotechnol.* 21(7):778-784, (Jul. 2, 2003, e-pub. Jun. 1, 2003).
Dufner et al. "Harnessing phage and ribosome display for antibody optimization," *Trends Biotechol.* 24(11):523-29 (2006).
Durocher et al. "High-level and high-throughput recombinant protein production by transient transfection of suspension-growing human 293-EBNA1 cells," *Nucleic Acids Research* 30(2 e9): nine pages, (2002).
Eaton et al. "Construction and Characterization of an Active Factor VIII Variant Lacking the Central One-Third of the Molecule," *Biochemistry* 25(26):8343-8347, (Dec. 30, 1986).
Edelman et al. "The covalent structure of an entire γG immunoglobulin molecule," *Proc. Natl. Acad. Sci. USA* 63:78-85, (1969).
Els Conrath et al. "Camel Single-domain Antibodies as Modular Building Units in Bispecific and Bivalent Antibody Constructs," *Journal of Biological Chemistry* 276(10):7346-7350, (Mar. 9, 2001).
Flatman et al. "Process analytics for purification of monoclonal antibodies," *J. Chromatogr B* 848:79-87, (2007).
Fraker et al. "Protein and Cell Membrane Iodinations With a Sparingly Soluble Chloroamide, 1,3,4,6-Tetrachloro-3a,6a-Diphenylglycoluril," *Biochem. Biophys. Res. Commun.* 80(4):849-857, (Feb. 28, 1978).
Gadgil et al. "Identification of cysteinylation of a free cysteine in the Fab region of a recombinant monoclonal IgG1 antibody using lys-C limited proteolysis coupled with LC/MS analysis," *Analytical biochem.* 2006: 355:165-174, (2006).
Galamb et al., "Inflammation, adenoma and cancer: objective classification of colon biopsy specimens with gene expression signature," *Dis Markers* 25(1):1-16, (2008).
Gazzano-Santoro et al. "A Non-Radioactive Complement-Dependent Cytotoxicity Assay for Anti-CD20 Monoclonal Antibody," *J. Immunol. Methods* 202:163-171, (1996).
Geisse et al., "Eukaryotic expression systems: A comparison," *Protein Expression and Purification* 8:271-282, (1996).
Geoghegan et al. "Site-Directed Conjugation of Nonpeptide Groups to Peptides and Proteins via Periodate Oxidation of a 2-Amino Alcohol. Application Modification at N Terminator Serine," *Bioconjugate Chem.* 3(2):138-146, (1992).
Gerspach et al. "Target-selective activation of a TNF prodrug by urokinase-type plasminogen activator (uPA) mediated proteolytic processing at the cell surface," *Cancer Immunol. Immunother* 55:1590-1600 (2006).
Gold et al. "A novel bispecific, trivalent antibody construct for targeting pancreatic carcinoma," *Cancer Res.* 68(12):4819-4826, (2008).
Goldenberg et al. "Bi-Specific Antibodies that Bind Specific Target Tissue and Targeted Conjugates," Derwent Information Ltd., 12 pages, (2012).
Goodman et al. Chapter 6: Basic and Clinical Immunology, 8th edition, Appleton & Lange, Norwalk, CT, pp. 66-79, (1994).
Graham et al. "A new technique for the assay of infectivity of human adenovirus 5 DNA," *Virology* 52 (2):456-467, (1973).
Graham et al. "Characteristics of a Human Cell Line Transformed by DNA From Human Adenovirus Type 5," *J. Gen Virol.* 36:59-72, (1977).
Greenwood et al. "Structural Motifs Involved in Human IgG Antibody Effector Functions,". *Eur. J. Immunology* 23(5):1098-1104, (May 1993).
Grönwall et al. "Generation of Affibody ligands binding interleukin-2 receptor alpha/CD25," *Biotechnol. Appl. Biochem.* 50(Pt. 2):97-112, (Jun. 2008).
Grote et al. "Bispecific Antibody Derivatives Based on Full-Length IgG Formats," Chapter 16 in *Methods in Molecular Biology* 901:247-263, (2012).
Gunasekaran et al. "Enhancing antibody Fc heterodimer formation through electrostatic steering effects: Applications to bispecific molecules and monovalent IgG," *The Journal of Biological Chemistry* 285(25):19637-19646, (Jun. 18, 2010).
Guss et al. "Structure of the IgG-Binding Regions of Streptococcal Protein G," *EMBO J.* 5(7):1567-1575 (1986).
Guyer et al. "Immunoglobulin Binding by Mouse Intestinal Epithelial Cell Receptors," *J. Immunol.* 117(2):587-593, (Aug. 1976).
Ham et al. "Media and Growth Requirements," *Meth. Enz.* 58:44-93 (1979).
Hamers-Casterman et al. "Naturally occurring antibodies devoid of light chains," *Nature* 363:446-448, (1993).
Hara et al. "Overproduction of Penicillin-Binding Protein 7 Suppresses Thermosensitive Growth Defect at Low Osmolarity Due to an spr Mutation of *Escherichia coli*," *Microbial Drug Resistance* 2(1):63-72, (1996).
Hartog et al. "The Insulin-like growth factor 1 receptor in cancer: Old focus, new future," European Journal of Cancer, Pergamon Press, Oxford, GB, 43(13):1895-1904, (Aug. 23, 2007).
Henry et al. "Clinical implications of fibroblast activation protein in patients with colon cancer," *Clin Cancer Res.* 13(6):1736-1741, (Mar. 15, 2007).
Hezareh et al. "Effector Function Activities of a Panel of Mutants of a Broadly Neutralizing Antibody against Human Immunodeficiency Virus Type 1," *Journal of Virology* 75(24):12161-12168, (Dec. 2001).
Hinman et al. "Preparation and Characterization of Monoclonal Antibody Conjugates of the Calicheamicins: A Novel and Potent Family of Antitumor Antibiotics," *Cancer Res.* 53:3336-3342, (Jul. 15, 1993).
Hollander. "Bispecific antibodies for cancer therapy," *Immunotherapy* 1(2):211-222, (Mar. 2009).
Holliger et al. "Diabodies': Small bBvalent and Bispecific Antibody Fragments," *Proc. Natl. Acad. Sci. USA* 90-6444-6448, (Jul. 1993).
Holt et al. "Domain Antibodies: Proteins for Therapy," *Trends Biotechnol.* 21(11):484-490, (Nov. 2003).
Hoogenboom and Winter. "By-passing immunisation. Human antibodies from synthetic repertoires of germline $V_H$ gene segments rearranged in vitro," *J Mol Biol.* 227 (2):381-388, (Sep. 20, 1992).
Huston et al. "Medical Applications of Single-Chain Antibodies," *Intern. Rev. Immunol.* 10(2-3):195-217, (1993).
Huston et al. "Protein Engineering of Antibody Binding Sites: Recovery of Specific Activity in an Anti-Digoxin Single-Chain Fv Analogue Produced in *Escherichia coli*," *Proc. Natl. Acad. Sci. U.S.A.* 85(16):5879-5883, (Aug. 1988).

(56) References Cited

OTHER PUBLICATIONS

Ibragimova et al. "Stability of the β-Sheet of the WW domain: A molecular dynamics simulation study," *Biophysical Journal* 77:2191-2198, (Oct. 1999).

Idusogie et al. "Mapping of the C1q binding site on rituxan, a Chimeric antibody with a human IgG1Fc," *The Journal of Immunology* 164:4178-4184, (2000).

International Search Report dated Dec. 6, 2011, for PCT Patent Application No. PCT/EP2011/064476 filed on Aug. 23, 2011, seven pages.

International Search Report dated Dec. 6, 2011, for PCT Patent Application No. PCT/EP2011/064468 filed on Aug. 23, 2011, seven pages.

Jackman et al. "Development of a Two-part Strategy to Identify a Therapeutic Human Bispedfic Antibody That Inhibits IgE Receptor Signaling," *The Journal of Biological Chemistry* 285(27):20850-20859, (Jul. 2, 2010).

Jakobovits et al. "Analysis of Homozygous Mutant Chimeric Mice: Deletion of the Immunoglobulin Heavy-Chain Joining Region Blocks B-cell Development and Antibody Production," *Proc. Natl. Acad. Sci. USA* 90(6):2551-2555, (Mar. 15, 1993).

Jakobovits et al. "Germ-line Transmission and Expression of a Human-derived Yeast Artificial Chromosome," *Nature* 362:255-258, (Mar. 1993).

Janeway. (Oct. 12, 1989). "Immunotherapy by Peptdes?," *Nature* 341:482-483.

Jang et al., "The structural basis for DNA binding by an anti-DNA autoantibody," *Mol. Immunol.* 35(18):1207-1217 (1998).

Jefferis et al. "IgG-Fc-mediated effector functions: molecular definition of interaction sites for effector ligands and the role of glycosylation," *Immunol Rev.* 163:59-76, (1998).

Jendreyko et al. "Simultaneous, Phenotypic Knockout of VEGF-R2 and Tie-2 With an Intradiabody Enhances Antiangiogenic Effects in Vivo," Therapieoptimierung and Risikostratifizierung, *Kiln Padiatr*, 218:143-151, (2006).

Jia et al. "A novel trifunctional IgG-like bispecific antibody to inhibit HIV-1 infection and enhance lysis of HIV by targeting activation of complement," *Virology Journal* 7(142):1-4, (Jun. 29, 2010).

Johnson et al., "Kabat Database and its applications: 30 years after the first variability plot," *Nucleic Acids Research* 28(1):214-218, (2000).

Johnson et al. "Construction of Single-Chain Fv Derivatives Monoclonal Antibodies and Their Production in *Escherichia coli*," *Methods Enzymol.* 203:88-98, (1991).

Johnson et al. "The Kabat Database and a Bioinformatics Example," Chapter 2 in *Methods in Molecular Biology*, Lo, B.K.C, Humana Press, Totawa, N.J., 248:11-25 (2003).

Joly et al. "Overexpression of *Escherichia coli* Oxidoreductases Increases Recombinant Insulin-like Growth Factor-I Accumulation," *Proc. Natl. Acad. Sci. USA* 95:2773-2777, (Mar. 1998).

Jones et al. "Replacing the Complementarity-Determining Regions in a Human Antibody With Those From a Mouse," *Nature* 321:522-525, (May 29, 1986).

Kabat et al. "Evolutionary and structural influences on light chain constant ($C_L$) region of human and mouse immunoglobulins," *Proc. Natl. Acad. Sci. USA* 72(7):2785-2788, (Jul. 1975).

Kabat et al. Sequences of Proteins of Immunological Interest (Table of Contents and Introduction), 5th edition, Bethesda, MD: Public Health Service, NIH, vol. 1, (1991).

Karadag et al. "ADAM-9 (MDC-9/meltrin-γ), a member of the a disintegrin and metalloproteinase family, regulates myeloma-cell-induced interleukin-6 production in osteoblasts by direct interaction with the αvβ5 integrin," *Blood* 107(8):3271-3278, (Apr. 15, 2006).

Kaufman. "Overview of Vector Design for Mammalian Gene Expression," *Molecular Biotechnology* 16:151-160, (2000).

Kazama et al. "Hepsin, a putative membrane-associated serine protease, activates human factor VII and initiates a pathway of blood coagulation on the cell surface leading to thrombin formation," *JBC* 270:66-72, (1995).

Kim et al. "Inhibition of Vascular Endothelial Growth Factor-Induced Angiogenesis Suppresses Tumour Growth in Vivo," *Nature* 362:841-844, (1993).

Kim et al. "Localization of the Site of the Murine IgG1 Molecule that is Involved in Binding to the Murine Intestinal Fc Receptor," *Eur J Immunol.* 24:2429-2434, (1994).

Klein et al. "Progress in Overcoming the Chain Association Issue in Bispecific Heterodimeric IgG Antibodies" *mAbs* 4(6):653-663, (2012).

Kleinschmidt et al. "Design of a modular immunotoxin connected by polyionic adapter peptides," *J. Mol. Biol.* 327(2):445-452, (Mar. 21, 2003).

Kobayashi et al. "Similarities in the Biodistribution of Iodine-Labeled Anti-Tac Single-Chain Disulfide-Stabilized Fv Fragment and Anti-Tac Disulfide-Stabilized Fv Fragment," *Nuclear Medicine & Biology* 25:387-393, (1998).

Kobayshi et al. "Tryptophan H33 plays an important role in pyrimidine (6-4) pyrimidone photoproduct binding by a high-affinity antibody," *Protein Engineering* 12(10):879-844, (1999).

Kodukula et al. "Biosynthesis of phosphatidylinositol glycan-anchored membrane proteins. Design of a simple protein substrate to characterize the enzyme that cleaves the COOH-terminal signal peptide," *The Journal of Biological Chemistry* 266(7):4464-4470, (Mar. 5, 1991).

Krugmann et al. "Structural Requirements for Assembly of Dimeric IgA Probed by Site-Directed Mutagenesis of J Chain and a Cysteine Residue of the α-chain CH2 Domain," *The Journal of Immunology* 159:244-249, (1997).

Kumar et al. "Molecular Cloning and Expression of the Fabs of Human Autoantibodies in *Escherichia coli*," *J. Biol. Chem.* 275(45):35129-35136, (Nov. 10, 2000).

Lamkanfi et al., "Inflammasomes: guardians of cytosolic sanctity," *Immunol. Rev.* 227(1):95-105, (Jan. 2009).

Lazar et al. "Transforming growth factor α: Mutation of aspartic acid 47 and leucine 48 results in different biological activities," *Molecular and Cellular Biology* 8(3):1247-1252, (Mar. 1988).

Lee et al. "Using substrate specificity of antiplasmin-cleaving enzyme for fibroblast activation protein inhibitor design," *Biochemistry* 48(23):5149-5158, (Jun. 16, 2009).

Leeman et al. "The Structure, Regulation, and Function of Human Matrix Metalloproteinase-13," *Crit. Rev Biochem Mol. Biol.* 37(3):149-166, (2002).

Liang et al. "Cross-species Vascular Endothelial Growth Factor (VEGF)-blocking Antibodies Completely Inhibit the Growth of Human Tumor Xenografts and Measure the Contribution of Stromal VEGF," *Journal of Biological Chemistry* 281(2):951-961, (2006).

Lifely et al. "Glycosylation and Biological Activity of CAMPATH-1H Expressed in Different Cell Lines and Grown Under Different Culture Conditions," *Glycobiology* 5(8):813-822, (Dec. 1995).

Lin et al. "Structure-Function relationships in glucagon: Properties of highly purified des-his-, monoiodo-, and [Des-Asn$^{28}$, Thr$^{29}$](homoserine lactone$^{27}$)-glucagon," *Biochemistry USA* 14:1559-1563, (1975).

Lindmark et al. "Binding of Immunoglobulins to Protein A and Immunoglobulin Levels in Mammalian Sera," *J. Immunol. Meth.* 62:1-13 (1983).

Liotta et al. "Metastatic potential correlates with enzymatic degradation of basement membrane collagen," *Nature* 284(5751) 67-68, (Mar. 6, 1980).

Liu et al. "Heterogeneity of Monoclonal Antibodies," *Journal of Pharmaceutical Sciences* 97(7):2426-2447, (Jul. 2008).

Liu et al. "Clinical and imaging diagnosis of primary hepatic lymphoma," *J First Mil Med. Univ*, 25(10):1290-1292, three pages, (2005). (Translation of the Abstract Only.).

Liu et al. "Eradication of Large Colon Tumor Xenografts by Targeted Delivery of Maytansinoids," *Proc. Natl. Acad. Sci. USA* 93:8618-8623, (Aug. 6, 1996).

Lode et al. "Targeted Therapy With a Novel Enediyene Antibiotic Calicheamicin θ$^I$ Effectively Suppresses Growth and Dissemination of Liver Metastases in a Syngeneic Model of Murine Neuroblastoma," *Cancer Res.* 58:2925-2928, (Jul. 15, 1998).

Lopez-Otin et al. "The regulatory crosstalk between kinases and proteases in cancer," *Nat. Rev. Cancer* 10(4):278-292, (Apr. 2010).

(56) References Cited

OTHER PUBLICATIONS

Love et al. "Recombinant antibodies possessing novel effector functions," *Methods in Enzymology* 178:515-527, (1989).
Lu et al. "A Fully Human Recombinant IgG-Like Bispecific Antibody to Both the Epidermal growth Factor Receptor and the Insulin-Like Growth Factor Receptor for Enhanced Antitumor Activity," *The Journal of Biological Chemistry* 280(20):19665-19672, (May 20, 2005).
Lu et al. "ADAMTS1 and MMP1 proteolytically engage EGF-like ligands in an osteolytic signaling cascade for bone metastasis," *Genes Dev.* 23(16):1882-1894, (Aug. 2009).
Lukas et al. "Inhibition of C1-Mediated Immune Hemolysis by Monomeric and Dimeric Peptides from the Second Constant Domain of Human Immunoglobulin G," *The Journal of Immunolgy* 127(6):2555-2560, (Dec. 1981).
Lund et al. "Oligosaccharide-protein interactions in IgG can modulate recognition by Fcγ receptors," *FASEB Journal* 9:115-119, (1995).
MacCallum et al. "Antibody-antigen Interactions: Contact Analysis and Binding Site Topography," *J. Mol. Biol.* 262:732-745, (1996).
Makrides. "Components of Vectors for Gene Transfer and Expression in Mammalian Cells," *Protein Expression and Purification* 17:183-202, (1999).
Malmborg et al. "BIAcore as a Tool in Antibody Engineering," *J. Immunol. Methods* 183:7-13, (1995).
Mamoune et al. "Calpain-2 as a target for limiting prostate cancer invasion," *Cancer Res.* 63(15):4632-4640, (Aug. 2003).
Mandler et al. "Immunoconjugates of Geldanamycin and Anti-HER2 Monoclonal Antibodies: Antiproliferative Activity on Human Breast Carcinoma Cell Lines," *J. of the Nat. Cancer Inst.* 92(19):1573-1581, (Oct. 4, 2000).
Mandler et al. "Modifications in Synthesis Strategy Improve the Yield and Efficacy of Geldanamycin-herceptin Immunoconjugates," *Bioconjugate Chem.* 13(4):786-791, (Jul.-Aug. 2002, e-pub. Jun. 19, 2002).
Mandler et al. "Synthesis and Evaluation of Antiproliferative Activity of a Geldanamycin-Herceptin Immunoconjugate," *Biorganic & Med. Chem. Letters* 10:1025-1028, (May 15, 2000).
Marks et al. "By-Passing Immunization: Human Antibodies From V-gene Libraries Displayed on Phage," *J Mol Biol.* 222(3):581-597, (Dec. 5, 1991).
Marvin et al. "Recombinant approaches to IgG-like bispecific antibodies," *Acta Pharmacol. Sin.* 26:649-658, (2005).
Marvin et al. "Bispecific antibodies for dual-modality cancer therapy: killing two signaling cascades with one stone," *Curr. Opin. Drug Discov. Devl.* 9:184-193, (2006).
Mason et al. (2004). "Coiled Coil Domains: Stability, Specificity, and Biological Implications," *ChemBioChem* 5:170-176.
Mather. "Establishment and Characterization of Two Distinct Mouse Testicular Epithelial Cell Lines," *Biology Reproduction* 23:243-251, (1980).
Mather et al. "Culture of Testicular Cells in Hormone-supplemented Serum-Free Medium," *Annals N.Y. Aca. Sci.* 383:44-68, (1982).
Matrisian. "Cancer biology: extracellular proteinases in malignancy," *Curr. Biol.* 9(20):R776-R778, (Oct. 1999).
McLean et al. "A point mutation in the CH3 domain of human IgG3 inhibits antibody secretion without affecting antigen specificity", *Molecular Immunology*, 42:1111-1119, (2005).
Meissner et al. "Transient Gene Expression: Recombinant Protein Production with Suspension-Adapted HEK293-EBNA Cells," *Biotechnology and Bioengineering* 75(2):197-203, (Oct. 20, 2001).
Melnyk et al. "Vascular Endothelial Growth Factor Promotes Tumor Dissemination by a Mechanism Distinct from Its Effect on Primary Tumor Growth," *Cancer Research* 56:921-924, (Feb. 15, 1996).
Merchant et al. "An efficient route to human bispecific IgG," *Nature Biotechnology* 16:677-681, (1998).
Milstein et al. "Hybrid Hybridomas and Their Use in Immunohistochemistry," *Nature* 305: 537-540, (Oct. 6, 1983).
Miller et al. "Design, Construction, and in Vitro Analyses of Multivalent Antibodies," *J. Immunol.* 170:4854-4861, (2003).
Mimura et al. "Role of Oligosaccharide Residues of IgG1-Fc in FcγRIIb Binding," *The Journal of Biological Chemistry* 276(49):45539-45547, (Dec. 7, 2001).
Minn et al. "Genes that Mediate Breast Cancer Metastasis to Lung," *Nature* 436(7050):518-524, (Jul. 2005).
Mirny et al. "Protein Folding Theory: From Lattice to All-Atom Models", *Annu. Rev. Biophys. Biomol. Struct.* 30:361-96, (2001).
Morgan et al. "The N-terminal End of the $C_H2$ Domain of Chimeric Human IgG1 anti-HLA-DR is Necessary for C1q, FcγRI and FcγRIII Binding," *Immunology* 86:319-324, (1995).
Morrison et al. "Chimeric Human Antibody Molecules: Mouse Antigen-Binding Domains with Human Constant Region Domains," *Proc. Natl. Acad. Sci. USA* 81(21):6851-6855, (Nov. 1984).
Morrison et al. "Variable region domain exchange influences the functional properties of IgG," *Journal of Immunology, American Association of Immunologists* 160:2802-2808, (Jan. 1, 1998).
Morrison. "Two Heads are Better than One," *Nature Biotechnology* 25(11):1233-1234, (Nov. 2007).
Morrison. "Success in Specification," *Nature* 368:812-813, (Apr. 1994).
Müller et al. "Recombinant Bispecific Antibodies for Cellular Cancer Immunotherapy," *Current Opinion in Molecular Therapeutics* 9:319-326, (2007).
Muller et al. "Processing and Sorting of the Prohormone Convertase 2 Propeptide," *J. Biol. Chem.* 275(50):39213-39222, (Dec. 15, 2000).
Müller et al. "The first constant domain ($C_H1$ and $C_L$) of an antibody used as heterodimerization domain for bispecific miniantibodies," *FEBS Letters* 422:259-264, (1998).
Mukhopadhyay et al. "Matrix metalloproteinase-12 is a therapeutic target for asthma in children and young adults," *J. Allergy Clin Immunol.* 126:70-76, (2010).
Murakami et al. "Cell Cycle Regulation, Oncogenes, and Antineoplastic Drugs" Chapter 1 in *The Molecular Basis of Cancer*, Mendelsohn and Israel, Philadelphia, W.B. Saunders, Philadelphia pp. 3-17, (1995).
Muyldermans et al. "Recognition of Antigens by Single-domain Antibody Fragments: the Superfluous Luxury of Paired Domains," *Trend Biochem. Sci.* 26(4):230-235, (Apr. 2001).
Natsume et al. "Fucose Removal From Complex-type Oligosaccharide Enhances the Antibody-dependent Cellular Cytotoxicity of Single-gene-encoded Bispecific Antibody Comprising of Two Single-Chain Antibodies Linked to the Antibody Constant Region," *Journal of Biochemistry* 140(3):359-368, (Sep. 1, 2006).
Nicolaou et al., "Calicheamicin $\theta^1_1$: A Rationally Designed Molecule with Extremely Potent and Selective DNA Cleaving Properties and Apoptosis Inducing Activity," *Agnew Chem. Intl. Ed. Engl.* 33(2):183-186, (1994).
Niculescu-Duvaz et al. "Antibody-directed Enzyme Prodrug Therapy (ADEPT): A Review," *Adv. Drg. Del. Rev.* 26:151-172, (1997).
Nieri et al. "Antibodies for Therapeutic Uses and the Evolution of Biotechniques," *Current Med. Chem.* 16(6):753-779, (Feb. 1, 2009).
Nilsson et al. "A synthetic IgG-binding domain based on staphylococcal protein A," *Prot. Eng.* 1:107-133, (1987).
Niwa et al. "IgG subclass-independent improvement of antibody-dependent cellular cytotoxicity by fucose removal from $Asn^{297}$-linked oligosaccharides," *J. Immunol. Methods* 306:151-160, (2005).
Nord et al. "A combinatorial library of an α-helical bacterial receptor domain,"*Prot. Eng.* 8:601-608, (1995).
Nord et al. "Binding proteins selected from combinatorial libraries of an α-helical bacterial receptor domain," *Nat. Biotech.* 15:772-777, (1997).
Norderhaug et al. "Versatile Vectors for Transient and Stable Expression of Recombinant Antibody Molecules in Mammalian Cells," *Journal of Immunological Methods* 204:77-87, (1997).
Novotný et al. "Structural invariants of antigen binding: Comparison of immunoglobulin $V_L$-$V_H$ and $V_L$-$V_L$ domain dimmers", *Proc. Natl. Acad. Sci. USA*, 82:4592-4596, (1985).
Offner et al. "T Cell Receptor Peptide Therapy Triggers Autoregulation of Experimental Encephalomyelitis," *Science* 251:430-432, (Jan. 25, 1991).

(56) References Cited

OTHER PUBLICATIONS

Ohno et al. "Antigen-binding specificities of antibodies are primarily determined by seven residues of $V_H$," *Proc. Natl. Acad. Sci. USA* 82(9):2945-2949, (May 1985).

Oliner et al. "Suppression of Angiogenesis and Tumor Growth by Selective Inhibition of Angiopoietin-2," *Cancer Cell* 6:507-516, (2004).

Orcutt, et al. "A modular IgG-scFv bispecific antibody topology," *Protein Engineering, Design & Selection* 23(4):221-228, (Apr. 2010, e-pub. Dec. 17, 2009).

Orlandi et al. "Cloning Immunoglobulin Variable Domains for Expression by the Polymerase Chain Reaction," *Proc. Natl. Acad. Sci. USA* 86:3833-3837, (May 1989).

O'Shea et al. "Peptide 'Velcro': design of a heterodimeric coiled coil," *Current Biology* 3(10):658-667, (1993).

Pace et al. "How to Measure and Predict the Molar Absorption Coefficient of a Protein," *Protein Science* 4(11): 2411-2423, (Nov. 1995).

Pakula et al. "Genetic analysis of protein stability and function," *Annu. Rev. Genet.* 23:289-310, (1989).

Pan et al. "Blocking Neuropilin-1 Function Has an Additive Effect with nti-VEGF to Ihibit Tumor Growth," *Cancer Cell* 11:53-67, (Jan. 2007).

Petitt et al. "Marine animal biosynthetic constituents for cancer chemotherapy," *J. Nat. Prod.* 44:482-485, (Jul.-Aug. 1981).

Pettit et al. "The Dolastatins," *Fortschr. Chem. Org. Naturst.* 70:1-79, (1997).

Pettit et al. "Antineoplastic Agents 360. Synthesis and Cancer Cell Growth Inhibitory Studies of Dolastatin 15 Structural Modifications," *Anti-Cancer Drug Design* 13:47-66, (1998).

Pettit et. al. "Specific Activities of Dolastatin 10 and Peptide Derivatives Against Cryptococcus Neoformans," *Antimirob. Agents Chemother.* 42:2961-2965, (Nov. 1998).

Pleass et al. "Identification of Residues in the CH2/CH3 Domain Interface of IgA Essential for Interaction With the Human fcα Receptor (Fcα R) CD89," *The Journal of Biology Chemistry* 274(33):23508-23514, (Aug. 13, 1999).

Plückthun et al. "New Protein Engineering Approaches to Multivalent and Bispecific Antibody Fragments," *Immunotechnology* 3:83-105, (1997).

Pluckthun. "Antibodies from *Escherichia coli*" Chapter 11 in *The Pharmacology of Monoclonal Antibodies: Handbook of Phannacology*, Rosenberg and Moore, eds., Berlin:Springer-Verlag, vol. 113, pp. 269-315, (1994).

Poncet. "The Dolastatins, A Family of Promising Antineoplastic Agents," *Curr. Pharm. Des.* 5:139-162, (1999).

PreScission Protease, GE Healthcare Catalogue No. 27-0843-01, located at http://www.gelifesciences.com/webapp/wcs/stores/servlet/productByld/en/GELifeScience, last visited on Jul. 10, 2013, one page.

Presta. "Antibody Engineering," *Curr. Op. Struct. Biol.* 2:593-596, (1992).

Presta et al. "Humanization of an Antibody Directed Against IgE," *J. Immunol.* 151(5):2623-2632, (Sep. 1, 1993).

Proba et al. "Functional Antibody Single-Chain Fragments From the Cytoplasm of *Escherichia coli*: Influence of Thioredoxin Reductase (TrxB)," *Gene* 159:203-207, (Jul. 4, 1995).

Raag et al. "Single-chain Fvs," *The FASEB Journal* 9:73-80, (Jan. 1995).

Radaev et al. "Recognition of IgG by Fcγ Receptor," *The Journal of Biological Chemistry* 276(19):16478-16483, (May 11, 2001).

Rajagopal et al. "A Form of Anti-Tac(Fv) Which is Both Single-chain and Disulfide Stabilized: Comparison with its single-chain and Disulfide-stabilized Homologs," *Protein Engineering* 10(12):1453-1459, (1997).

Raju. "Glycosylation Variations with Expression Systems and Their Impact on Biological Activity of Therapeutic Immunoglobulins," *BioProcess International* 1(4): 44-53, (Apr. 2003).

Ramm et al. "The Peroplasmic *Escherichia coli* Peptidylproly cis,trans-Isomerase FkpA," *J. Biol. Chem.* 275(22):17106-17113, (Jun. 2, 2001).

Ravetch et al. "Fc Receptors," *Annu. Rev. Immunol.* 9:457-492, (1991).

Rawlings. "A large and accurate collection of peptidase cleavages in the MEROPS database," Database (Oxford), pp. 1-14, (2009, e-pub. Nov. 2, 2009).

Reiter et al. (1994). "Stabilization of the Fv Fragments in Recombinant Immunotoxins by Disulfide Bonds Engineered into Conserved Framework Regions," *Biochemistry* 33(18):5451-5449.

Reiter et al. "Improved Binding and Antitumor Activity of a Recombinant Anti-erbB2 Immunotoxin by Disulfide Stabilization of the Fv Fragment," *J. Biol. Chem.* 269(28):18327-18331, (Jul. 15, 1994).

Reiter et al. "Engineering Interchain Disulfide Bonds Into Conserved Framework Regions of Fv Fragments: Improved Biochemical Characteristics of Recombinant Immunotoxins Containing Disulfide-Stabilized Fv," *Protein Eng.* 7(5):697-704, (May 1994).

Reiter et al. "Cytotoxic and antitumor activity of a recombinant immunotoxin composed of disulfide-stabilized anti-Tac Fv fragment and truncated *Pseudomonas* exotoxin," *International Journal of Cancer* 58:142-149, (1994).

Reiter et al., "Antitumor activity and pharmacokinetics in mice of a recombinant immunotoxin containing a disulfide-stabilized Fv fragment," *Cancer Research* 54:2714-2718, (1994).

Reiter et al. "Antibody engineering of recombinant Fv immunotoxins for improved targeting of cancer: disulfide-stabilized Fv immunotoxins," *Clin. Cancer Res.* 2(2):245-252, (Feb. 1, 1996).

Reiter et al. "Disulfide stabilization of antibody Fv: computer predictions and experimental evaluation," *Protein Engineering* 8:1323-1331, (1995).

Reiter et al. "Construction of a functional disulfide-stabilized TCR Fv indicates that antibody and TCR Fv frameworks are very similar in structure," *Immunity* 2:281-287, (1995).

Reiter et al. "Engineering antibody Fv fragments for cancer detection and therapy: disulfide-stabilized Fv fragments," *Nature Biotechnology* 14:1239-1245, (1996).

Remacle et al. "Substrate Cleavage Analysis of Furin and Related Proprotein Convertases," *Journal of Biological Chemistry* 283(30):20897-20906, (Jul. 25, 2008).

Riechmann et al. "Reshaping Human Antibodies for Therapy," *Nature* 332:323-327, (Mar. 24, 1988).

Roitt et al. (2000). "Immunology," Moscow, Mir., pp. 100-101 (English Translation).

Roitt A. et al. "Multispecific Antibodies Comprising Full Length Antibodies and Single Chain Fab Fragments," *Immunology*, English Translation, Moscow:Mir, pp. 388-389, (2000).

Rossi et al. "Multivalent Anti-CD20/Anti-CD22 Bispecific Antibody Fusion Proteins Made by the DNL Method Show Potent Lymphoma Cytotoxicity," *Blood, American Society of Hematology* 108(11):707A, Poster Board No. Session 673-II, Abstract No. 2495, from 48th Annual Meeting of the American Society of Hematology, Orland, Florida, Dec. 9-12, 2006, (2006).

Routier et al. "The Glycosylation Pattern of a Humanized IgGI Antibody (D1.3) Expressed in CHO Cells," *Glycoconjugate Journal* 14:201-207, (1997).

Rowland et al. "Drug Localisation and Growth Inhibition Studies of Vindesine-Monoclonal Anti-CEA Conjugates in a Human Tumour Xenograft," *Cancer Immunol. Immunother.* 21:183-187, (1986).

Rupert et al. "Cloning and Expression of Human $TAF_{II}250$: a TBP-Associated Factor Implicated in Cell-Cycle Regulation," *Nature* 362:175-179, (Mar. 11, 1993).

Ruppert et al. "Protease levels in breast, ovary and other gynecological tumor tissues: prognostic importance in breast cancer," *Cancer Detect. Prev.* 21(5):452-459, (1997).

Sambrook et al. Molecular Cloning: A Laboratory Manual "The Table of Contents" Cold Spring Harbor, New York: Cold Spring Harbor Laboratory Press, (1989).

Santos et al. "Generation and Characterization of a Single Gene-Encoded Single-Chain-tetravalent Antitumor Antibody" *Clinical Cancer Research* 5(10 Suppl):3118s-3123s, (Oct. 1999).

(56) References Cited

OTHER PUBLICATIONS

Schaefer et al. "Immunoglobulin domain crossover as a generic approach for the production of bispecific IgG antibodies," *Proc. Natl. Acad. Sci. U.S.A.* 108(27):11187-11192, (Jul. 5, 2011, e-pub. Jun. 20, 2011).
Schmidt et al. "Suppression of Metastasis Formation by a Recombinant Single Chain Antibody-Toxin Targeted to Full-length and Oncogenic Variant EGF Receptors," *Oncogene* 18:1711-1721, (1999).
Schmiedl et al. "Expression of a bispecific dsFv-dsFv' antibody fragment in *Escherichia coli*," *Protein Engineering* 13(10):725-734, (Oct. 2000).
Schoonjans et al. "Fab Chains as an Efficient Heterodimerization Scaffold for the Production of Recombinant Bispecific and Trispecific Antibody Derivatives," *Journal of Immunology* 165:7050-7057, (2000).
Schröder et al. "III. Formation of the Peptide Bond," *The Peptides*, vol. 1, Academic Press, New York, New York, pp. 76-136, (1965).
Schwartz et al. "A superactive insulin: (B10-aspartic acid]insulin(human)," *Proc. Natl. Acad. Sci. USA* 84:6408-6411, (Sep. 1987).
Scott et al. "Biologic protease inhibitors as novel therapeutic agents," *Biochimie* 92(11):1681-1688, (Nov. 2010).
Shechter et al. "Selective Chemical Cleavage of Tryptophanyl Peptide Bonds by Oxidative Chlorination With N-Chlorosuccinimide," *Biochemistry* 15(23):5071-5075, (1976).
Shen et al. "Single variable domain-IgG fusion: A novel recombinant approach to Fc domain-containing bispecific antibodies," *J. of Biological Chemistry* 281(16):10706-10714, (Apr. 21, 2006, e-pub. Feb. 15, 2006).
Sheriff et al. "Redefining the minimal antigen-binding fragment," *Nature Struct. Biol.* 3:733-736, (1996).
Shields et al. "High Resolution Mapping of the Binding Site on Human IgG1 for FcγRI, FcγRII, FcγRIII and FcRn and Design of IgG1 Variants with Improved Binding to the FcγR," *Journal of Biological Chemistry* 276 (9):6591-6604, (2001).
Shields et al. "Lack of Fucose on Human IgG1 N-Linked Oligosaccharide Improves Binding to Human FcγRIII and Antibody-dependent Cellular Toxicity," *J Biol Chem.* 277(30):26733-26740, (Jul. 26, 2002).
Shinkawa et al. "The Absence of Fucose but Not the Presence of galactose or Bisecting N-Acetylglucosamine of Human IgG1 Complex-Type Oligosaccharides Shows the Critical Role of Enhancing Antibody-Dependent Cellular cytotoxicity," *J. Biol. Chem.* 278 (5) 3466-3473, (2003).
Siebenlist et al. "*E. coli* RNA Polymerase Interacts Homologously with Two Different Promoters," *Cell* 20:269-281, (1980).
Simmons et al. "Expression of full-length immunoglobulins in *Escherichia coli*: Rapid and Efficient production of aglycosylated antibodies," *Journal of Immunological Methods* 263:133-147, (2002).
Simon et al. "Antibody Domain Mutants Demonstrate Autonomy of the Antigen Binding Site," *The EMBO Journal* 9(4):1051-1056, (1990).
Sims et al. "A Humanized CD18 Antibody Can Block Function Without Cell Destruction," *J. Immunol.* 151(4):2296-2308, (Aug. 15, 1993).
Singer et al. "Genes and Genomes," Moscoer, MIR 1:63-64 (1998). (With English Translation.).
Smith-Gill et al. "Contributions of Immunoglobulin Heavy and Light Chain to Antibody Specificity for Lysozyme and Two Haptens," *J. Immunol.* 139(12):4135-4144, (Dec. 15, 1987).
Song et al. "Light Chain of Natural Anibody Plays a Dominant Role in Protein Antigen Binding," *Biochem. Biophys. Res. Comm.* 268(2):390-394, (2000).
Steiner. "The Biosynthesis of Biologically Active Peptides: A Perspective," Chapter 1 in *Peptide Biosynthesis and Processing*, Fricker ed., CRC Press, Boca Raton, FL, pp. 1-15, (1991).
Stella et al. "Prodrugs: A Chemical Approach to Target Drug Delivery" *Directed Drug Delivery*, Borchardt et al (ed.), Human Press, pp. 247-267, (1985).
Stetler-Stevenson et al. "Progelatinase A activation during tumor cell invasion," *Invasion Metastasis* 14(1-6):259-268, (1994-1995).

Stevenson et al. "A chimeric antibody with dual Fc regions (bisFabFc) prepared by manipulations at the IgG hinge," *Anti-cancer Drug Des.* 3(4):219-230, (Mar. 1989).
Stites et al. "Immunoglobulin Protiens," Chapter 6 in *Basic Clinical Immunology*, 8th Edition, Appleton & Lange, Norwalk, CT, pp. 66-79, (1994).
Stork et al. "A Novel Tri-Functional Antibody Fusion Protein With Improved Pharmacokinetic Properties Generated by Fusing a Bispecific Single-Chain Diabody With an Albumin-Binding Domain From Streptococcal Protein G," *Protein Eng. Des. Sel.* 20(11):569-576, (Nov. 2007, e-pub. Nov. 3, 2007).
Syrigos et al. "Antibody Directed Enzyme Prodrug Therapy (ADEPT): A Review of the Experimental and Clinical Considerations," *Anticancer Research* 19:605-614, (1999).
Tao et al. "The Differential Ability of Human IgG1 and IgG4 to Activate Complement is Determined by the COOH-terminal Sequence of the $C_H2$ Domain," *J. Exp. Med* 173:1025-1028, (Apr. 1991).
Thie et al. "Multimerization Domains for Antibody Phage Display and Antibody Production," *New Biotech.* 26(6):314-321, (Jul. 22, 2009).
Thommesen et al. "Lysine 322 in the human IgG3 $C_H2$ domain is crucial for antibody dependent complement activation," *Molecular Immunology* 37:995-1004, (2000).
Thorpe. "Antibody Carriers of Cyotoxic Agents in Cancer Therapy: A Review," in *A Monoclonal Antibodies 84: Biological and Clinical Applications*, A. Pinchera et al (eds) pp. 475-506, (1985).
Torres et al. "Variable-Region-Identical Antibodies Differing in Isotype Demonstrate Differences in Fine Specificity and Idiotype", *The Journal of Immunology*, 174:2132-2142, (2005).
Tripathi et al. "Laminin-332 is a substrate for hepsin, a protease associated with prostate cancer progression," *JBC* 283:30576-30584, (2008).
Tso et al. "Preparation of a Bispecific F(ab')$_2$ Targeted to the Human II-2 Receptor," *J. Hematotherapy* 4:389-94, (1995).
Umaña et al. "Engineered Glycoforms of an Antineuroblastoma IgG1 with Optimized Antibody-Dependent Cellular Cytotoxic Activity," *Nature Biotechnology* 17(2):176-180 (Feb. 1999).
Urlaub et al. "Isolation of Chinese Hamster Cell Mutants Deficient in Dihydrofolate Reductase Activity," *Proc. Natl. Acad Sci USA* 77(7):4216-4220, (Jul. 1980).
U.S. Appl. No. 14/551,957, filed Nov. 24, 1014 for Castoldi et al.
U.S. Appl. No. 14/735,024, filed Jun. 9, 2015 for Christensen et al.
Van Dijk et al. "Human antibodies as next generation therapeutics," *Curr Opin Chem Biol.* 5(4): 368-374, (Aug. 2001).
Van Spriel et al. "Immunotherapeutic perspective for bispecific antibodies," *Immunology Today* 21(8):391-397, (Aug. 2000).
Van't Veer et al. "Gene expression profiling predicts clinical outcome of breast cancer," *Nature* 415(6871):530-536, (Jan. 2002).
Vazquez-Ortiz et al. "Overexpression of cathepsin F, matrix metalloproteinases 11 and 12 in cervical cancer," *BMC Cancer* 5:68, (Jun. 30, 2005).
Velasco et al. "Human cathepsin O. Molecular cloning from a breast carcinoma, production of the active enzyme in *Escherichia coli*, and expression analysis in human tissues," *J. Biol Chem* 269(43):27136-27142, (Oct. 28, 1994).
Verhoeyen et al. "Reshaping Human Antibodies: Grafting an Antilysozyme Activity," *Science* 239:1534-1536, (Mar. 25, 1988).
Veveris-Lowe et al. "Seminal Fluid Characterization for Male Fertility and Prostate Cancer: Kallikrein-Related Serine Proteases and whole Proteome Approaches," *Semin Thromb Hemost.* 33(1):87-99, (2007).
Vijayalakshmi. "Antibody Purification Methods," *Applied Biochemistry and Biotechnology* 75:93-102, (1998).
Vitetta et al. "Redesigning Nature's Poisons to Create Anti-tumor Reagents," *Science* 238:1098-1104, (Nov. 20, 1987).
Walker et al. "Efficient and Rapid Affinity Purification of Proteins Using Recombinant Fusion Proteases," *Bio/Technology* 12:601-605, (1994).
Walker et al. "Efficient Recovery of High-Affinity Antibodies From a Single-Chain Fab Yeast Display Library," *J. Mol. Biol.* 389(2):365-375, (Jun. 5, 2009, e-pub. Apr. 16, 2009).

(56) References Cited

OTHER PUBLICATIONS

Ward et al. "Binding Activities of a Repertoire of Single Immunoglobulin Variable Domains Secreted From *Escherichia coli*," *Nature* 341:544-546, (Oct. 12, 1989).
Warren et al. "Regulation by Vascular Endothelial Growth Factor of Human Colon Cancer Tumorigenesis in a Mouse Model of Experimental Liver Metastasis," *J. Clin. Invest.* 95:1789-1797, (1995).
Webber et al. "Preparation and characterization of a disulfide-stabilized Fv fragment of the anti-Tac antibody: comparison with its single-chain analog," *Molecular Immunology* 32:249-258, (1995).
Werner et al. "Appropriate Mammalian Expression Systems for Biopharmaceuticals," *Drug Research* 48(8):870-880, (1998).
Wielockx et al. "Matrilysin (matrix metalloproteinase-7): a new promising drug target in cancer and inflammation?" *Cytokine Growth Factor Rev.* 15(2-3):111-115, (Apr.-Jun. 2004).
Willems et al. "Optimizing expression and purification from cell culture medium of trispecific recombinant antibody derivatives," *Journal of Chromatography B* 786:161-176, (2003).
Wilman. "Prodrugs in Cancer Chemotherapy," *Biochemical Society Transactions* 14:375-382, 615th Meeting Belfast, 8 pages, (1986).
Woof et al. "Human antibody-FC receptor interactions illuminated by crystal structures," *Nat. Rev. Immunol.* 4:1-11, (2004).
Woyke et al. "In Vitro Activities and Postantifungal Effects of the Potent Dolastatin10 Derivative Auristatin PHE," *Antimicrob. Agents and Chemother.* 45(12):3580-3584, (Dec. 2001).
Wranik et al. "Luz-Y: A Novel Platform for the Mammalian Cell Production of Full-length IgG Bispeciic Antibodies," *Journal of Biological Chemistry* 287(52):43331-43339, (Dec. 21, 2012).
Wright et al. "ADAM28: a potential oncogene involved in asbestos-related lung adenocarcinomas," *Genes Chromosomes Cancer* 49(8): 688-698, (Aug. 2010).
Wright et al. "Effect of Glycosylation on Antibody Function: Implications for Genetic Engineering," *Trends in Biotechnology* 15:26-32, (Jan. 1997).
Written Opinion of the International Searching Authority dated Dec. 6, 2011, for PCT Patent Application No. PCT/EP2011/064476 filed on Aug. 23, 2011, four pages.
Written Opinion of the International Searching Authority dated Dec. 6, 2011, for PCT Patent Application No. PCT/EP2011/064468 filed on Aug. 23, 2011, four pages.
Xu et al. (2000). "Diversity in the CDR3 region of V(H) is sufficient for most antibody specificities," *Immunity* 13:37-45.
Yamaguchi et al. "Proteolytic Fragmentation With High Specificity of Mouse Immunoglobulin G," *Journal of Immunological Methods* 181:259-267, (1995).
Yaniv. "Enhancing Elements for Activation of Eukaryotic Promoters," *Nature* 297:17-18, (May 6, 1982).
Zapata et al. "Engineering Linear F(ab')$_2$ Fragments for Efficient Production in *Escherichia coli* and Enhanced Antiproliferative Activity," *Protein Eng.* 8(10):1057-1062, (1995).
Zeidler et al. "Simultaneous activation of T cells and accessory cells by a new class of intact bispecific antibody results in efficient tumor cell killing," *Journal of Immunology* 163:1246-1252, (1999).
Zhu et al. "Remodeling Domain Interfaces to Enhance Heterodimer Formation," *Protein Science* 6:781-788, (1997).
Zuo et al. "An efficient route to the production of an IgG-like bispecific antibody," *Protein Engineering* 13(5):361-367, (2000).
International Search Report dated Aug. 6, 2013, for PCT Application No. PCT/US2013/025365, filed Feb. 8, 2013, 6 pages.
Written Opinion dated Aug. 6, 2013, for PCT Application No. PCT/US2013/025365, filed Feb. 8, 2013, 9 pages.
International Preliminary Report on Patentability dated Aug. 21, 2014, for PCT Patent Application No. PCT/US2013/025365, filed on Feb. 8, 2013, 11 pages.
International Search Report dated Jun. 15, 2011 for PCT Patent Application No. PCT/US2010/002546 filed on Sep. 16, 2010, five pages.
Written Opinion of the International Searching Authority dated Jun. 15, 2011 for PCT Patent Application No. PCT/US2010/002546 filed on Sep. 16, 2010, seven pages.
International Search Report dated Aug. 5, 2010, for PCT Application No. PCT/EP2010/003559, filed on Jun. 14, 2010, 10 pages.
Bao et al., "HER2-mediated upregulation of MMP-1 is involved in gastric cancer cell invasion," *Arch Biochem Biophys* 499(1-2):49-55, (Jul. 2010).
Neuberger et al., "A hapten-specific chimaeric IgE antibody with human physiological effector function," *Nature* 314:268-270, (Mar. 21, 1985).
Netzel-Arnett et al., "Sequence Specificities of Human Fibroblast and Neutrophil Collagenases," *J. Biol. Chem.* 266(11):6747-6755, (Apr. 15, 1991).
Netzel-Arnett et al., "Comparative sequence specificities of human 72- and 92-kDa gelatinases (type IV collagenases) and PUMP (matrilysin)," *Biochemistry* 32(25):6427-6432, (Jun. 29, 1993).
International Preliminary Report on Patentability for PCT/EP2011/054505, dated Oct.2, 2012, filed on Mar. 24, 2011, 8 pages.
Adams et al. "Highly Specific in Vivo Tumor Targeting by Monovalent and Divalent Forms of 741F8 Anti-c-erbB-2 Single-Chain Fv," *Cancer Res.* 53:4026-4034, (Sep. 1, 1993).
Alt et al. "Novel Tetravalent and Bispecific IgG-Like Antibody Molecules Combining Single-chain Diabodies With the Immunoglobulin γ1 Fc or CH3 Region," *FEBS Lett.* 454(1-2):90-94, (Jul. 2, 1999).
An et al. "Targeted Drug Delivery to Mesothelioma Cells Using Functionally Selected Internalizing Human Single-Chain Antibodies," *Mol. Cancer Ther.* 7:569-578, (Mar. 2008), 17 pages.
Anthony et al. "A Recombinant IgG Fc That Recapitulates the Anti-inflammatory Activity of IVIG," *Science* 320(5874):373-376, (Apr. 2008), 12 pages.
Armour et al. "Recombinant Human IgG Molecules Lacking Fcγ Receptor I Binding and Monocyte Triggering Activities," *Eur. J. Immunol.* 29:2613-2624, (1999).
Backer et al. "Molecular vehicles for targeted drug delivery," *Bioconjugate Chem.* 13:462-467, (2002).
Behrens. "Synthesis of Achiral Linker Reagents for Direct Labelling of Oligonucleotides on Solid Supports," *Nucleosides & Nucleotides* 18:291-305, (1999).
Bordusa. "Protease-Catalyzed Formation of C-N Bonds," *Highlights in Bioorganic Chemistry*, Schmuck, C. and Wennemers, H., (eds.), Wiley VCH, Weinheim, pp. 389-403, (2004).
Brennan et al. "Preparation of Bispecific Antibodies by Chemical Recombination of Monoclonal Immunoglobulin G1 Fragments," *Science* 229:81-83, (1985).
Carmichael et al. "Evaluation of a Tetrazolium-Based Semiautomated Colorimetric Assay: Assessment of Chemosensitivity Testing," *Cancer Res.* 47:936-942, (Feb. 15, 1987).
Carter et al. "High Level *Escherichia Coli* Expression and Production of a Bivalent Humanized Antibody Fragment," *Bio/Technology* 10:163-167, (Feb. 1992).
Carter. "Potent Antibody Therapeutics by Design", *Nature Reviews Immunology* 6:343-357, (May 2006).
Chames et al. "Bispecific Antibodies for Cancer Therapy," *Current Opinion in Drug Discovery & Development* 12(2):276-283, (2009).
Chan et al. "Therapeutic Antibodies for Autoimmunity and Inflammation," *Nature Reviews* 10(5):301-316, (2010).
Charlton. "Expression and Isolation of Recombinant Antibody Fragments in *E. coli*," *Methods in Molecular Biology*, vol. 248, Lo, B.K.C. (ed.), Humana Press, Totowa, N.J., pp. 245-254, (2003).
Chen et al. "Improved Variants of SrtA for Site-Specific Conjugation on Antibodies and Proteins With High Efficiency," *Scientific Reports* 6(31899):1-12, (Aug. 18, 2016).
Cheong et al. "Affinity Enhancement of Bispecific Antibody Against Two Different Epitopes in the Same Antigen," *Biochem. Biophys. Res. Commun.* 173:795-800, (1990).
Chin et al. "Addition of p-azido-L-Phenylalanine to the Genetic Code of *Escherichia coli*," *J. Am. Chem. Soc.*, 124(31):9026-9027, (2002).
Chin et al. "In Vivo Photocrosslinking With Unnatural Amino Acid Mutagenesis", *ChemBioChem*, 3(11):1135-1137, (2002).
Chin et al. "Addition of a Photocrosslinking Amino Acid to the Genetic Code of *Escherichia coli*", *Proc. Natl. Acad. Sci. U.S.A.*, 99(17):11020-11024, (Aug. 20, 2002).

(56) References Cited

OTHER PUBLICATIONS

Clackson et al. "Making antibody fragments using phage display libraries," *Nature* 352:624-628, (1991).
Clancy et al. "Sortase Transpeptidases: Insights Into Mechanism, Substrate Specificity, and Inhibition," *Biopolymers* 94(4):385-396, (2010).
Cocuzza. "A Phosphoramidite Reagent for automated solid phase synthesis of 5'-biotinylated oligonucleotides," *Tetrahedron Letters* 30:6287-6290, (1989).
De Graaf et al. "Nonnatural Amino Acids for Site Specific Protein Conjugation," *Bioconjug. Chem.* 20:1281-1295, (2009).
Dervan. "Molecular Recognition of DNA by Small Molecules," *Bioorg. Med. Chem.* 9:2215-2235, (2001).
Ding et al. "Gold Nanorods Coated with Multilayer Polyelectrolyte as Contrast Agents for Multimodal Imaging," *J. Phys. Chem. C* 111:12552-12557, (2007).
Dubowchik et al. "Doxorubicin immunoconjugates Containing Bivalent, Lysosomally-Cleavable Dipeptide Linkages," *Bioorg. & Med. Chem. Letters* 12:1529-1532, (2002).
Ellman et al. "Biosynthetic Method for Introducing Unnatural Amino Acids Site-Specifically Into Proteins," *Meth. Enzym.* 202:301-336, (1991).
Frese et al. "Formylglycine aldehyde Tag—Protein Engineering Through a Novel Post-Translational Modification," *ChemBioChem* 10:425-427, (2009).
Friend et al. "Phase I study of an Engineered Aglycosylated Humanized CD3 Antibody in Renal Transplant Rejection," *Transplantation* 68(11):1632-1637, (Dec. 15, 1999).
Gautier et al. "An Engineered Protein Tag for Multiprotein Labeling in Living Cells," *Chem. Biol.* 15:128-136, (Feb. 2008).
Gerngross. "Advances in the Production of Human Therapeutic Proteins in Yeasts and Filamentous Fungi," *Nat. Biotech.* 22(11):1409-1414, (Nov. 2004).
Goldenberg et al. "Multifunctional Antibodies by the Dock-and-Lock Method for Improved Cancer Imaging and Therapy by Pretargeting," *J. Nuc. Med.* 49(1):158-163, (Jan. 2008).
Gruber et al. "Efficient Tumor Cell Lysis Mediated by a Bispecific Single Chain Antibody Expressed in *Escherichia coli*," *J. Immunol.* 152:5368-5374, (1994).
Hackenberger et al. "Chemoselective Ligation and Modification Strategies for Peptides and Proteins," *Angew. Chem. Int. Ed.* 47:10030-10074, (2008).
Hatfield et al. "Antiangiogenic Therapy in Acute Myelogenous Leukemia: Targeting of Vascular Endothelial Growth Factor and Interleukin 8 as Possible Antileukemic Strategies," *Curr. Cancer Drug Targets* 5:229-248 (2005).
Hayashi et al. "Application of L-DNA as a Molecular Tag," *Nucl. Acids Symp. Ser.* 49:261-262, (2005).
Herberman. "Immunodiagnosis of Cancer," in *The Clinical Biochemistry of Cancer*, Fleisher, ed., American Association of Clinical Chemists, p. 347, (1979).
Hey et al. "Artificial, Non-Antibody Binding Proteins for Pharmaceutical and Industrial Applications," *Trends Biotechnol.* 23:514-522, (Oct. 2005).
Hoppe et al. "A Parallel Three Stranded Alpha-Helical Bundle at the Nucleation Site of Collagen Triple-Helix Formation," *FEBS Lett.* 344:191-195, (1994).
Huber, R. et al. (1976). "Crystallographic Structure Studies of an IgG Molecule and an Fc Fragment,", *Nature*, 264:415-420.
Hudson et al. "Engineered Antibodies," *Nat. Med.* 9(1):129-134, (Jan. 2003).
Huynh et al. Nucleic Acids Symposium Series 29, Second International Symposium on Nucleic Acids Chemistry, pp. 19-20, (1993).
Ilangovan et al. "Structure of Sortase, the Transpeptidase That Anchors Proteins to the Cell Wall of *Staphylococcus aureus*," *Proc. Natl. Acad. Sci. U.S.A.* 98(11):6056-6061, (May 22, 2001).
Iyer. "Abasic Oligodeoxyribonucleoside Phosphorothioates: Synthesis and Evaluation as Anti-HIV-1 Agents," *Nucleic Acids Research* 18:2855-2859, (1990).
Jeffrey et al. "Dipeptide-Based Highly Potent Doxorubicin Antibody Conjugates," *Bioorg. Med. Chem. Lett.* 16:358-362, (2006).
Jiang et al. "Advances in the Assessment and Control of the Effector Functions of Therapeutic Antibodies," *Nat. Rev. Drug Discov.*, 10(2):101-111, (Feb. 2011).
Kindt et al. Kuby Immunology, 6th ed., W.H. Freeman and Co., N.Y., p. 91, (2007).
King et al. "Monoclonal Antibody Conjugates of Doxorubicin Prepared With Branched Peptide Linkers: Inhibition of Aggregation by Methoxytriethyleneglycol Chains," *J. Med. Chem.* 45(19):4336-4343, (2002).
Kontermann. "Dual Targeting strategies With Bispecific Antibodies," *MABS Landes Bioscience* 4(2):182-197, (2012).
Kostelny et al. "Formation of a Bispecific Antibody by the use of Leucine Zippers," *J. Immunol.* 148:1547-1553, (Mar. 1, 1992).
Kratz et al. "Prodrugs of Anthracyclines in Cancer Chemotherapy," *Current Med. Chem.* 13(5):477-523, (2006).
Labrijn et al. "Species-Specific Determinants in the IgG CH3 Domain Enable Fab-Arm Exchange by Affecting the Noncovalent CH3—CH3 Interaction Strength," *The Journal of Immunology* 187:3238-3246, (2011, e-pub. Aug. 12, 2011).
Landschulz et al. "The Leucine Zipper: A Hypothetical Structure Common to a New Class of DNA Binding Proteins," *Science* 240:1759-1764, (1988).
Levary et al. "Protein-Protein Fusion Catalyzed by Sortase A," *PLOS One* 6(4):e18342.1-e18342.6, (Apr. 6, 2011).
Li et al. "Optimization of Humanized IgGs in Glycoengineered *Pichia pastoris*," *Nat. Biotech.* 24(2):210-215, (Feb. 2006).
Liu et al. "Mapping Tumor Epitope Space by Direct Selection of Single-Chain Fv Antibody Libraries on Prostate Cancer Cells," *Cancer Res.* 64:704-710, (Jan. 15, 2004).
Madej et al. "Engineering of an Anti-Epidermal Growth Factor Receptor Antibody to Single Chain Format and Labeling by Sortase A-Mediated Protein Ligation," *Biotechnology and Bioengineering*, 109(6):1461-1470, (Jun. 2012, e-pub. Dec. 26, 2011).
Mann. "Proteomic Analysis of Post-Translational Modifications," *Biochemistry* 21:255-261, (Mar. 2003).
McCarron et al. "Antibody Conjugates and Therapeutic Strategies," *Mol. Interventions* 5:368-380, (2005).
McKeen et al. "Synthesis of Fluorophore and Quencher Monomers for Use in Scorpion Primers and Nucleic Acid Structural Probes," *Organic & Biomol. Chem.* 1:2267-2275, (2003, e-pub. May 28, 2003).
Metz et al. "Bispecific Digoxigenin-Binding Antibodies for Targeted Payload Delivery," *Proc. Natl. Acad. Sci. U.S.A.* 108(20):8194-8199, (May 17, 2011).
Metz et al. "Bispecific Antibody Derivatives with Restricted Binding Functionalities that are Activated by Proteolytic Processing," *Protein Engineering Design and Selection* 25(10):571-580, (2012, e-pub. Sep. 13, 2012).
Meyer et al. "Oligonucleotide sequential bis-conjugation via click-oxime and click-Huisgen procedures," *Journal of Organic Chemistry* 75:3927-3930, (2010, e-pub. Mar. 5, 2010).
Mizukami et al. "Induction of Interleukin-8 Preserves the Angiogenic Response in HIF-1α-Deficient Colon Cancer Cells," *Nature Med.* 11(9):992-997, (Sep. 2005).
Möhlmann et al. "In Vitro Sortagging of an Antibody Fab Fragment: Overcoming Unproductive Reactisakamotons of Sortase With Water and Lysine Side Chains," *Chembiochem: A European Journal of Chemical Biology* 12(11):1774-1780, (2011).
Morimoto et al. "Single-Step Purification of F(ab')2 Fragments of Mouse Monoclonal Antibodies (Immunoglobulins G1) by Hydrophobic Interaction High Performance Liquid Chromatography Using TSKgel Phenyl-5PW," *J. Biochem. Biophys. Meth.* 24:107-117, (1992).
Morocho et al. "Novel Biotin Phosphoramidites With Super-Long Tethering Arms," *Nucleosides, Nucleotides & Nucleic Acids* 22:1439-1441, (2003, e-pub. Aug. 31, 2006).
Muller et al. "A Dimeric Bispecific Miniantibody Combines Two Specificities With Avidity," *FEBS Lett.* 432:45-49, (1998).

(56) References Cited

OTHER PUBLICATIONS

Nagy et al., "Stability of Cytotoxic Luteinizing Hormone-Releasing Hormone Conjugate (AN-152) Containing Doxorubicin 14-O-Hemiglutarate in Mouse and Human Serum in Vitro: Implications for the Design of Preclinical Studies," *Proc. Natl. Acad. Sci. USA* 97(2):829-834, (Jan. 18, 2000).
Nelson et al. "Oligonucleotide Labeling Methods. 3. Direct Labeling of Oligonucleotides Employing a Novel, Non-Nucleosidic, 2-Aminobutyl-1,3-Propanediol Backbone," *Nucleic Acids Research* 20:6253-6259, (1992).
Neri et al. "High-Affinity Antigen Binding by Chelating Recombinant Antibodies (CRAbs)," *J. Mol. Biol.* 246:367-373, (1995).
Nielsen et al. "Therapeutic Efficacy of Anti-ErbB2 Immunoliposomes Targeted by a Phage Antibody Selected for Cellular Endocytosis," *Biochim. Biophys. Acta* 1591:109-118, (2002).
Noren et al. "A General Method for Site-Specific Incorporation of Unnatural Amino Acids into Proteins," *Science* 244:182-188, (1989).
Novellino et al. "A Listing of Human Tumor Antigens Recognized by T Cells: Mar. 2004 Update," *Cancer Immunol. Immunother.* 54:187-207, (2005).
Pack et al. "Miniantibodies: Use of Amphipathic Helices to Produce Functional, Flexibly Linked Dimeric FV Fragments With High Avidity in *Escherichia coli,*" *Biochem.* 31(6):1579-1584, (Feb. 18, 1992).
Parmiani et al. "Unique Human Tumor Antigens: Immunobiology and use in Clinical Trials," *J. Immunol.* 178:1975-1979, (2007).
Pon. "A Long Chain Biotin Phosphoramidite Reagent for the Automated Synthesis of 5'-Biotinylated Oligonucleotides," *Tetrahedron Letters* 32:1715-1718, (1991).
Popp et al. "Making and Breaking Peptide Bonds: Protein Engineering Using Sortase," *Angewandte Chemie* 50(22):5024-5032, (2011).
Portolano et al. "Lack of Promiscuity in Autoantigen-Specific H and L Chain Combinations as Revealed by Human H and L Chain Roulette," *J. Immunol.* 150(3):880-887, (Feb. 1, 1993).
Presta et al. "Humanization of an Anti-Vascular Endothelial Growth Factor Monoclonal Antibody for the Therapy of Solid Tumors and Other Disorders," *Cancer Res.* 57:4593-4599, (Oct. 15, 1997).
Presta. "Molecular Engineering and Design of Therapeutic Antibodies," *Current Opinion in Immunology* 20:460-470, (2008).
Prokhorenko et al. "Incorporation of a Pyrene Nucleoside Analogue Into Synthetic Oligodeoxynucleotides Using a Nucleoside-Like Synthon," *Bioorganic & Medicinal Chemistry Letters* 5(18):2081-2084 (1995).
Putnam et al. "Synthesis and evaluation of RNA transesterification efficiency using stereospecific serinol-terpyridine conjugates," *Nucleosides, Nucleotides & Nucleic Acids* 24(9):1309-1323, (2005, e-pub. Aug. 31, 2006).
Ramzaeva et al. "Oligonucleotides Fuctionalized by Fluorescein and Rhodamine Dyes: Michael Addition of Methyl acrylate to 2'-Deoxypseudouridine," *Helv. Chim. Acta* 83:1108-1126, (2000).
Ren et al. "Macrophage Migration Inhibitory Factor Stimulates Angiogenic Factor Expression and Correlates With Differentiation and Lymph Node Status in Patients with Esophageal Squamous Cell Carcinoma," *Ann. Surg.* 242(1):55-63, (Jul. 2005).
Ren et al. "A biocompatible Condensation Reaction for the Labeling of Terminal Cysteine Residues on Proteins," *Angew. Chem. Int. Ed.* 48:9658-9662, (2009).
Roget et al. "Synthesis and Use of Labelled Nucleoside Phosphoramidite Building Blocks Bearing a Reporter Group: Biotinyl, Dinitrophenyl, Pyrenyl and Dansyl," *Nucleic Acids Research* 17:7643-7651, (1989).
Roux et al. "Comparisons of the Ability of Human IgG3 Hinge Mutants, IgM, IgE, and IgA2, to Form Small Immune Complexes: A Role for Flexibility and Geometry," *J. Immunol.* 161(8):4083-4090, (1998).
Salfeld. "Isotype Selection in Antibody Engineering," *Nat. Biotechnol.* 25(12):1369-1372, (Dec. 2007).
Schlaeger. "The Protein Hydrolysate, Primatone RL, is a Cost-Effective Multiple Growth Promoter of Mammalian Cell Culture in Serum-Containing and Serum-Free Media and Displays Anti-Apoptosis Properties," *J. Immunol. Methods* 194:191-199, (1996).
Schlaeger et al. "Transient Gene Expression in Mammalian Cells Grown in Serum-Free Suspension Culture," *Cytotechnology* 30:71-83, (1999).
Seela. "Oligodeoxyribonucleotides Containing 1,3-Propanediol as Nucleoside Substitute," *Nucleic Acids Research* 15(7):3113-3129, (1987).
Sensi et al. "Unique Tumor Antigens: Evidence for Immune Control of Genome Integrity and Immunogenic Targets for T cell-Mediated Patient-Specific Immunotherapy," *Clin. Cancer Res.* 12:5023-5032, (Sep. 1, 2006).
Senter. "Potent Antibody Drug Conjugates for Cancer Therapy," *Curr. Opin. Chem. Biol.* 13:235-244, (2009, e-pub. May 4, 2009).
Seo et al. "Post-Translational Modifications and Their Biological Functions: Proteomic Analysis and Systematic Approaches," *Biochemistry and Molecular Biology* 37(1):35-44, (Jan. 2004).
Shi et al. "A Stereospecific Synthesis of L-deoxyribose, L-ribose and L-ribosides," *Tetrahed.* 58:3287-3296, (2002).
Silva et al. "Biotinylated for the Preparation Oligonucleotide Multibiotinilados," *Biotecnologia Aplicada* 15:154-158, (1998). (English Abstract Only).
Sondermann et al. "The 3.2-A Crystal Structure of the Human IgG1 Fc Fragment-FcγRIII Complex," *Nature*, 406:267-273, (Jul. 20, 2000).
Strop et al. "Generating Bispecific Human IgG1 and IgG2 Antibodies from Any Antibody Pair," *Journal of Molecular Biology* 420(3):204-219, (2012, e-pub. Apr. 25, 2012).
Su et al. "Novel Non-Nucleosidic Phosphoramidites for Oligonucleotide Modification and Labeling," *Bioorganic & Medicinal Chemistry Letters* 7(13):1639-1644, (1997).
Sunbulet al. "Site Specific Protein Labeling by Enzymatic Post-translational Modification," *Org. Biomol. Chem.* 7:3361-3371, (2009, e-pub. Jul. 28, 2009).
Ta et al. "Enzymatic Single-Chain Antibody Tagging a Universal Approach to Targeted Molecular Imaging and Cell Homing in Cardiovascular Disease", *Circulation Research*, 109(4):365-373, (2011).
Taki et al. "Transglutaminase-Mediated N- and C-Terminal Fluorescein Labeling of a Protein Can Support the Native Activity of the Modified Protein," *Prot. Eng. Des. Sel.* 17(2):119-126, (2004, e-pub. Jan. 12, 2004).
Taylor et al. "Native Chemical Ligation: Semisynthesis of Post-Translationally Modified Proteins and Biological Probes,"*Nucl. Acids Mol. Biol.* 22:65-96, (2009).
Thies et al. "Folding and Association of the Antibody Domain CH3:prolyl Isomerization Preceeds Dimerization," *J. Mol. Biol.* 293:67-69, (1999).
Theisen et al. "Fluorescent Dye Phosphoramidite Labelling of Oligonucleotides," *Nucleic Acids Symposium Series 27, Nineteenth Symposium on Nucleic Acids Chemistry* 27:99-100, (1992).
Ton-That, H. et al. "Purification and Characterization of Sortase, the Transpeptidase that Cleaves Surface Proteins of *Staphylococcus aureus* at the LPXTG Motif," *Proc. Natl. Acad. Sci. U.S.A.* 96(22):12424-12429, (Oct. 26, 1999).
Torgov et al. "Generation of an Intensely Potent Anthracycline by a Monoclonal Antibody-Beta-Galactosidase Conjugate," *Bioconjug. Chem.* 16(3):717-721, (2005).
Tsukiji et al. "Sortase-Mediated Ligation: A Gift from Gram-Positive Bacteria to Protein Engineering," *Chembiochem* 10(5):787-798, (2009).
Urata et al., "Synthesis and Properties of Mirror-Image DNA," *Nucl. Acids Res.* 20(13):3325-3332, (1992).
Vallbohmer et al. "Molecular Determinants of Cetuximab Efficacy," *J. Clin. Oncol.* 23(15):3536-3544, (May 20, 2005).
Wagner et al. "Bispecific Antibody Generated With Sortase and Click Chemistry has Broad Antiinfluenza Virus Activity," *Proc. Natl. Acad. Sci. USA* 111:16820-16825, (Nov. 25, 2014).
Wang et al. "Site-Specific Fluorescent Labeling of DNA Using Staudinger Ligation,"*Bioconjugate Chemistry* 14(3):697-701, (2003).

(56) References Cited

OTHER PUBLICATIONS

Wang et al. "Expanding the Genetic Code," *Chem. Commun (Camb.)*, 7:1-11, (2002).
Ward et al. "The Effector Functions of Immunoglobulins: Implications for Therapy," *Ther. Immunol.* 2:77-94, (1995).
Witte et al. "Preparation of Unnatural N-to-N and C-to-C protein Fusions," *Proc. Natl. Acad. Sci. USA* 109(30):11993-11998, (Jul. 24, 2012).
Wojczewski et al. "Fluorescent Oligonucleotides—Versatile Tools as Probes and Primers for DNA and RNA Analysis," *Synlett* 10:1667-1678, (1999).
Wörn et al. "Stability Engineering aof Antibody Single-Chain Fv Fragments," *J. Mol. Biol.* 305:989-1010, (2001).
Wright et al. "Phage Display of Chelating Recombinant Antibody Libraries," *Molecular Immunology* 44:2860-2869, (2007).
Yazaki et al. "Expression of Recombinant Antibodies in Mammalian Cell Lines," *Methods in Molecular Biology*, vol. 248, Lo, B.K.C. (ed.), Humana Press, Totowa, NJ (2004), pp. 255-268.
Zahn et al. "Alternative Heterocycles for DNA Recognition: A 3-Pyrazole/Pyrrole Pair Specifies for G.C Base Pairs," *Bioorg. Med. Chem.* 8:2467-2474, (2000).

\* cited by examiner

BISPECIFIC ANTIBODIES

The present invention relates to bispecific antibodies, methods for their production, pharmaceutical compositions containing said antibodies, and uses thereof.

CROSS-REFERENCE TO RELATED APPLICATIONS

This application claims the benefit of European Patent Application No. 10003270.5, filed on Mar. 26, 2010, the disclosure of which is incorporated herein by reference in its entirety.

BACKGROUND OF THE INVENTION

A wide variety of multispecific recombinant antibody formats have been developed in the recent past, e.g. tetravalent bispecific antibodies by fusion of, e.g., an IgG antibody format and single chain domains (see e.g. Coloma, M. J., et al., Nature Biotech 15 (1997) 159-163; WO 2001/077342; and Morrison, S. L., Nature Biotech. 25 (2007) 1233-1234).

Also several other new formats wherein the antibody core structure (IgA, IgD, IgE, IgG or IgM) is no longer retained such as dia-, tria- or tetrabodies, minibodies, several single chain formats (scFv, Bis-scFv), which are capable of binding two or more antigens, have been developed (Holliger, P., et al., Nature Biotech 23 (2005) 1126-1136; Fischer, N., Léger O., Pathobiology 74 (2007) 3-14; Shen, J., et al., Journal of Immunological Methods 318 (2007) 65-74; Wu, C., et al., Nature Biotech. 25 (2007) 1290-1297).

All such formats use linkers either to fuse the antibody core (IgA, IgD, IgE, IgG or IgM) to a further binding protein (e.g. scFv) or to fuse e.g. two Fab fragments or scFvs (Fischer N., Léger O., Pathobiology 74 (2007) 3-14). It has to be kept in mind that one may want to retain effector functions, such as e.g. complement-dependent cytotoxicity (CDC) or antibody dependent cellular cytotoxicity (ADCC), which are mediated through the Fc receptor binding, by maintaining a high degree of similarity to naturally occurring antibodies.

In WO 2007/024715 are reported dual variable domain immunoglobulins as engineered multivalent and multispecific binding proteins. A process for the preparation of biologically active antibody dimers is reported in U.S. Pat. No. 6,897,044. Multivalent $F_V$ antibody construct having at least four variable domains which are linked with each over via peptide linkers are reported in U.S. Pat. No. 7,129,330. Dimeric and multimeric antigen binding structures are reported in US 2005/0079170. Tri- or tetra-valent monospecific antigen-binding protein comprising three or four Fab fragments bound to each other covalently by a connecting structure, which protein is not a natural immunoglobulin are reported in U.S. Pat. No. 6,511,663. In WO 2006/020258 tetravalent bispecific antibodies are reported that can be efficiently expressed in prokaryotic and eukaryotic cells, and are useful in therapeutic and diagnostic methods. A method of separating or preferentially synthesizing dimers which are linked via at least one interchain disulfide linkage from dimers which are not linked via at least one interchain disulfide linkage from a mixture comprising the two types of polypeptide dimers is reported in US 2005/0163782. Bispecific tetravalent receptors are reported in U.S. Pat. No. 5,959,083. Engineered antibodies with three or more functional antigen binding sites are reported in WO 2001/077342.

Multispecific and multivalent antigen-binding polypeptides are reported in WO 1997/001580. WO 1992/004053 reports homoconjugates, typically prepared from monoclonal antibodies of the IgG class which bind to the same antigenic determinant are covalently linked by synthetic cross-linking Oligomeric monoclonal antibodies with high avidity for antigen are reported in WO 1991/06305 whereby the oligomers, typically of the IgG class, are secreted having two or more immunoglobulin monomers associated together to form tetravalent or hexavalent IgG molecules. Sheep-derived antibodies and engineered antibody constructs are reported in U.S. Pat. No. 6,350,860, which can be used to treat diseases wherein interferon gamma activity is pathogenic. In US 2005/0100543 are reported targetable constructs that are multivalent carriers of bi-specific antibodies, i.e., each molecule of a targetable construct can serve as a carrier of two or more bi-specific antibodies.

Genetically engineered bispecific tetravalent antibodies are reported in WO 1995/009917. In WO 2007/109254 stabilized binding molecules that consist of or comprise a stabilized scFv are reported.

Bispecific antibodies against EGFR and IGF-1R are known from Lu, D., et al., Biochemical and Biophysical Research Communications 318 (2004) 507-513; Lu, D., et al., J. Biol. Chem., 279 (2004) 2856-2865; and Lu, D., et al., J. Biol Chem. 280 (2005) 19665-72.

US 2007/0274985 relates to synthetic antibody molecules comprising single chain Fab (scFab) proteins which can also be associated to dimers, including heteromeric antibodies, wherein at least two single chain antibody molecules are associated.

WO 2009/080253 relates to bispecific bivalent antibodies.

However in view of different problems and aspects of multispecific antibodies (like e.g. pharmacokinetic and biological properties, stability, aggregation, expression yield, side products) there is a need of further alternative multispecific antibody formats.

SUMMARY OF THE INVENTION

In one aspect the invention is directed to a bispecific antibody comprising
  a) the heavy chain and the light chain of a first full length antibody that specifically binds to a first antigen;
  b) the heavy chain and the light chain of a second full length antibody that specifically binds to a second antigen, wherein the N-terminus of the heavy chain is connected to the C-terminus of the light chain via a peptide linker.

In another aspect of the invention the bispecific antibody according to the invention is further characterized in that
  the CH3 domain of the heavy chain of the full length antibody of a) and the CH3 domain of the heavy chain of the full length antibody of b) each meet at an interface which comprises an alteration in the original interface between the antibody CH3 domains;
  wherein i) in the CH3 domain of one heavy chain
  an amino acid residue is replaced with an amino acid residue having a larger side chain volume, thereby generating a protuberance within the interface of the CH3 domain of one heavy chain which is positionable in a cavity within the interface of the CH3 domain of the other heavy chain
  and wherein
  ii) in the CH3 domain of the other heavy chain
  an amino acid residue is replaced with an amino acid residue having a smaller side chain volume, thereby generating a cavity within the interface of the second CH3 domain within which a protuberance within the interface of the first CH3 domain is positionable.

In another aspect the bispecific antibody according to the invention is characterized in that
both CH3 domains are further altered by the introduction of cysteine (C) as amino acid in the corresponding positions of each CH3 domain such that a disulfide bridge between both CH3 domains can be formed.

In another aspect of the invention the bispecific antibody according to the invention is characterized in that
the antibody heavy chain variable domain (VH) and the antibody light chain variable domain (VL) of the heavy and light chain of the second full length antibody under b) are disulfide stabilized by introduction of a disulfide bond between the following positions:
i) heavy chain variable domain position 44 to light chain variable domain position 100,
ii) heavy chain variable domain position 105 to light chain variable domain position 43, or
iii) heavy chain variable domain position 101 to light chain variable domain position 100.

In another aspect of the invention the bispecific antibody according to the invention is characterized in that
a) the first full length antibody specifically binds to IGF-1R and comprises a heavy chain with the amino acid sequence of SEQ ID NO: 1, and a light chain with the amino acid sequence of SEQ ID NO: 2, and
b) the second full length antibody specifically binds to EGFR and comprises a heavy chain connected to the light chain via a peptide linker wherein said peptide connected heavy and light chain have the amino acid sequence of SEQ ID NO: 3.

In another aspect of the invention the bispecific antibody according to the invention is characterized in that
a) the first full length antibody specifically binds to IGF-1R and comprises a heavy chain with the amino acid sequence of SEQ ID NO: 1, and a light chain with the amino acid sequence of SEQ ID NO: 2, and
b) the second full length antibody specifically binds to EGFR and comprises a heavy chain connected to the light chain via a peptide linker wherein said peptide connected heavy and light chain have amino acid sequence of SEQ ID NO: 4.

In another aspect of the invention the bispecific antibody according to the invention is characterized in that
a) the first full length antibody specifically binds to EGFR and comprises a heavy chain with the amino acid sequence of SEQ ID NO: 5, and a light chain with the amino acid sequence of SEQ ID NO: 6, and
b) the second full length antibody specifically binds to IGF-1R and comprises a heavy chain connected to the light chain via a peptide linker wherein said peptide connected heavy and light chain have amino acid sequence of SEQ ID NO: 7.

In another aspect of the invention the bispecific antibody according to the invention is characterized in that
a) the first full length antibody specifically binds to EGFR and comprises a heavy chain with the amino acid sequence of SEQ ID NO: 5, and a light chain with the amino acid sequence of SEQ ID NO: 6, and
b) the second full length antibody specifically binds to IGF-1R and comprises a heavy chain connected to the light chain via a peptide linker wherein said peptide connected heavy and light chain have amino acid sequence of SEQ ID NO: 8.

In another aspect of the invention the bispecific antibody according to the invention is characterized in that the antibody comprises a constant region of IgG1.

In another aspect of the invention the bispecific antibody according to the invention is characterized in that the antibody is glycosylated with a sugar chain at Asn297 wherein the amount of fucose within the sugar chain is 65% or lower.

Still further aspects of the invention are a pharmaceutical composition comprising said bispecific antibody, said composition for the treatment of cancer, the use of said bispecific antibody for the manufacture of a medicament for the treatment of cancer, a method of treatment of patient suffering from cancer by administering said bispecific antibody. to a patient in the need of such treatment.

A further aspect of the invention is a nucleic acid molecule encoding a chain of a bispecific antibody according to the invention.

The invention further provides expression vectors containing said nucleic acid according to the invention capable of expressing said nucleic acid in a prokaryotic or eukaryotic host cell, and host cells containing such vectors for the recombinant production of a bispecific antibody according to the invention.

The invention further comprises a prokaryotic or eukaryotic host cell comprising a vector according to the invention.

The invention further comprises a method for the production of a bispecific antibody according to the invention, characterized by expressing a nucleic acid according to the invention in a prokaryotic or eukaryotic host cell and recovering said bispecific antibody from said cell or the cell culture supernatant. The invention further comprises the antibody obtained by such method for the production of a bispecific antibody.

Another aspect of the invention is a method for the preparation of a bispecific antibody according to the invention comprising the steps of
a) transforming a host cell with vectors comprising nucleic acid molecules encoding
aa) the heavy chain and the light chain of a first full length antibody that specifically binds to a first antigen; and
ab) the heavy chain and the light chain of a second full length antibody that specifically binds to a second antigen, wherein the N-terminus of the heavy chain is connected to the C-terminus of light chain via a peptide linker; and
b) culturing the host cell under conditions that allow synthesis of said antibody molecule; and
c) recovering said antibody molecule from said culture.

It has now been found that the bispecific antibodies according to the invention have valuable characteristics such as good expression yields in mammalian cells like HEK293 cells and CHO cells, stability, biological or pharmacological activity, pharmacokinetic properties They can be used e.g. for the treatment of diseases such as cancer. These bispecific antibodies according to the invention comprising 3 poylpeptide chains especially have a valuable side product profile during expression in mammalian cells.

DETAILED DESCRIPTION OF THE INVENTION

In one aspect the invention is directed to a bispecific antibody comprising
a) the heavy chain and the light chain of a first full length antibody that specifically binds to a first antigen;
b) the heavy chain and the light chain of a second full length antibody that specifically binds to a second antigen, wherein the N-terminus of the heavy chain is connected to the C-terminus of light chain via a peptide linker.

Figure 1:
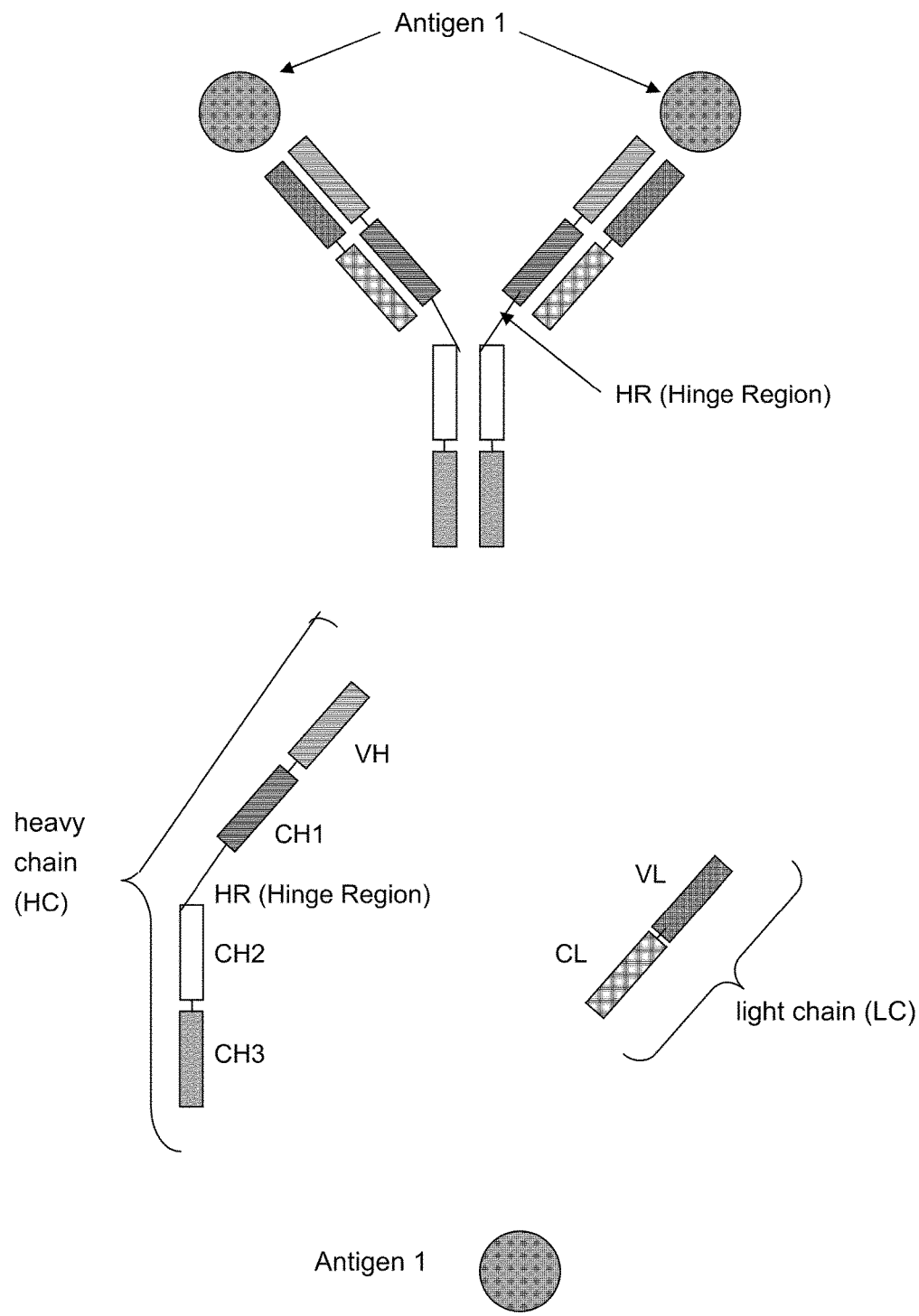
FIG. 1 Schematic structure of a full length antibody without CH4 domain specifically binding to a first antigen 1 with two pairs of heavy and light chain which comprise variable and constant domains in a typical order.
Figure 2:
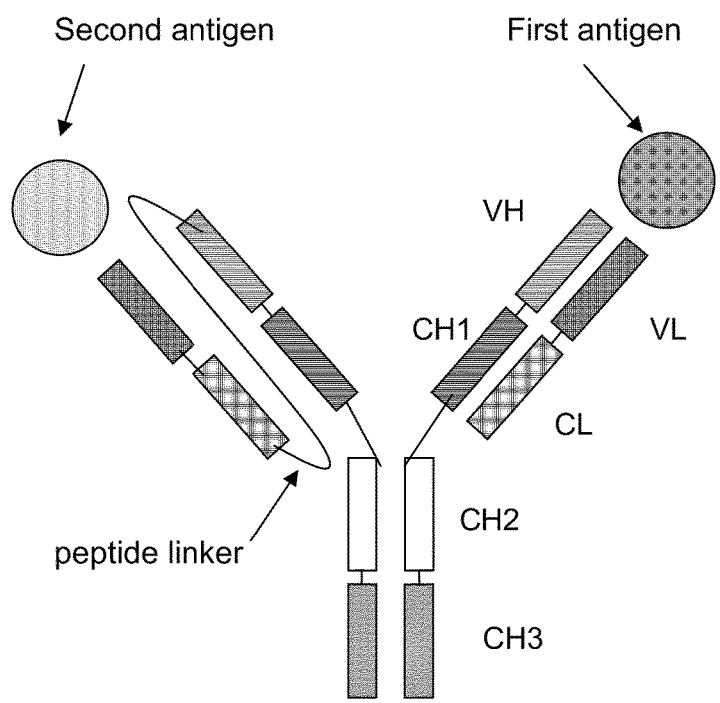
FIG. 2 Schematic structure of the bispecific antibody according to the invention.
Figure 3A:
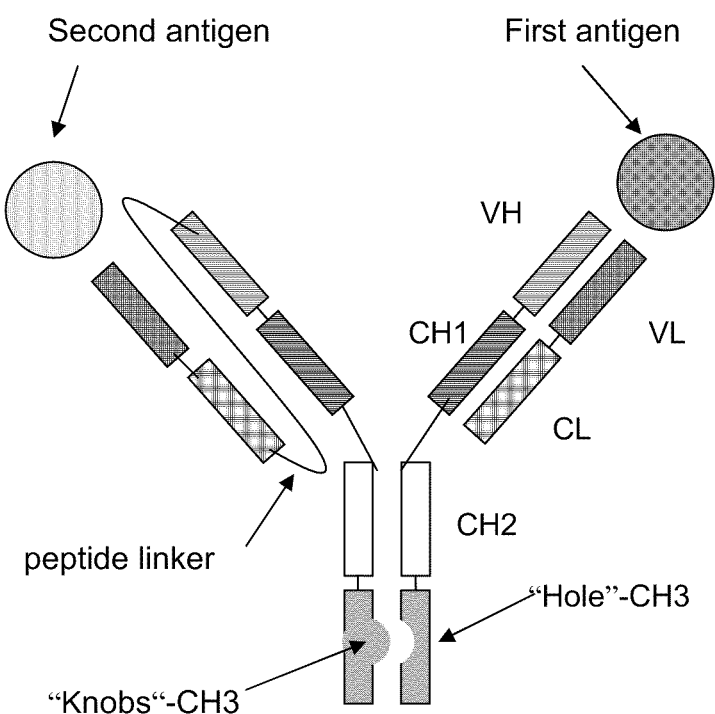
FIGS. 3a and 3b Schematic structure of the bispecific antibody according to the invention including knobs-into hole modified CH3 domains.
Figure 3B:
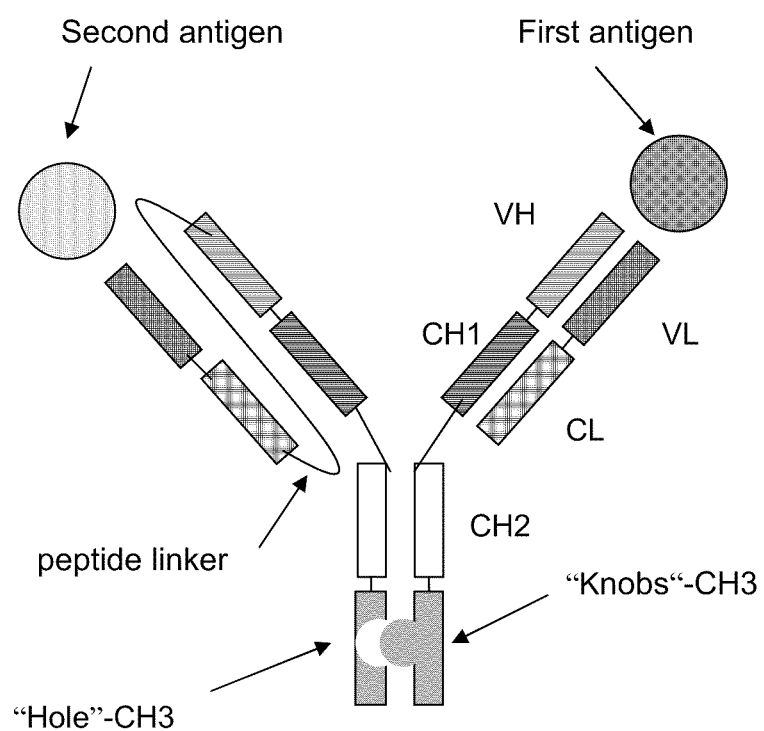
Figure 4A:
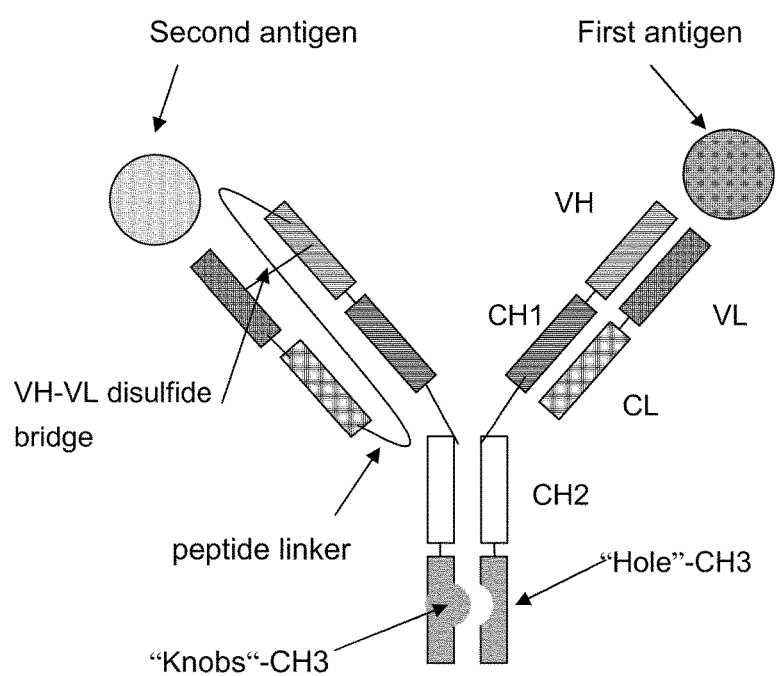
FIGS. 4a and 4b Schematic structure of the bispecific antibody according to the invention including knobs-into hole modified CH3 domains and disulfide stabilization of the VH and VL domain of the second antibody heavy and light chain.
Figure 4B:
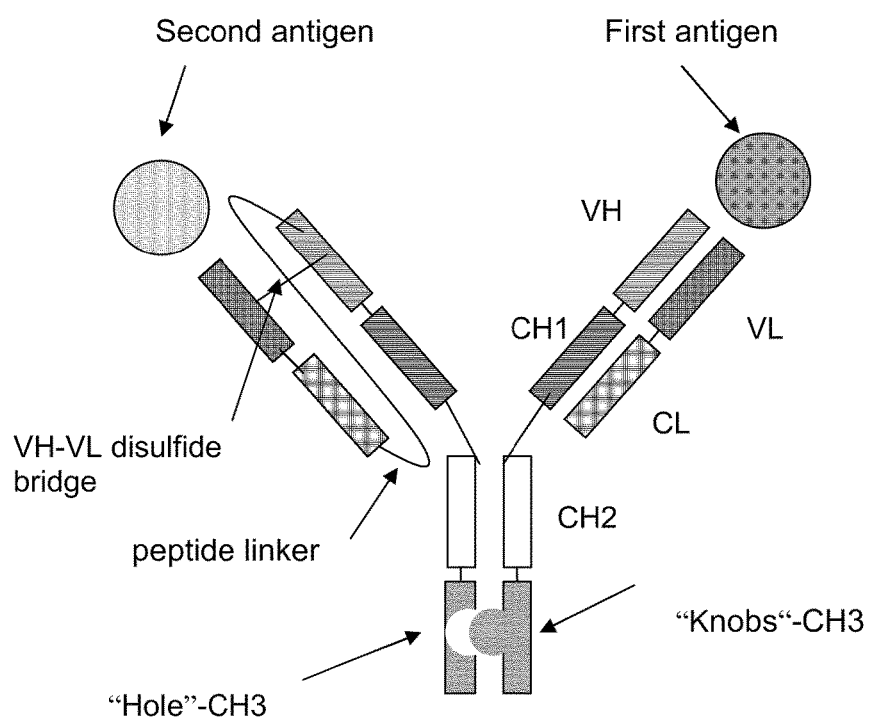

The term "full length antibody" denotes an antibody consisting of two "full length antibody heavy chains" and two "full length antibody light chains" (see FIG. 1). A "full length antibody heavy chain" is a polypeptide consisting in N-terminal to C-terminal direction of an antibody heavy chain variable domain (VH), an antibody constant heavy chain domain 1 (CH1), an antibody hinge region (HR), an antibody heavy chain constant domain 2 (CH2), and an antibody heavy chain constant domain 3 (CH3), abbreviated as VH-CH1-HR-CH2-CH3; and optionally an antibody heavy chain constant domain 4 (CH4) in case of an antibody of the subclass IgE. Preferably the "full length antibody heavy chain" is a polypeptide consisting in N-terminal to C-terminal direction of VH, CH1, HR, CH2 and CH3. A "full length antibody light chain" is a polypeptide consisting in N-terminal to C-terminal direction of an antibody light chain variable domain (VL), and an antibody light chain constant domain (CL), abbreviated as VL-CL. The antibody light chain constant domain (CL) can be κ (kappa) or λ (lambda). The two full length antibody chains are linked together via inter-polypeptide disulfide bonds between the CL domain and the CH1 domain and between the hinge regions of the full length antibody heavy chains. Examples of typical full length antibodies are natural antibodies like IgG (e.g. IgG 1 and IgG2), IgM, IgA, IgD, and IgE. The full length antibodies according to the invention can be from a single species e.g. human, or they can be chimerized or humanized antibodies. The full length antibodies according to the invention comprise two antigen binding sites each formed by a pair of VH and VL, which both specifically bind to the same antigen. The C-terminus of the heavy or light chain of said full length antibody denotes the last amino acid at the C-terminus of said heavy or light chain. The N-terminus of the heavy or light chain of said full length antibody denotes the last amino acid at the N-terminus of said heavy or light chain.

The term "peptide linker" as used within the invention denotes a peptide with amino acid sequences, which is preferably of synthetic origin. These peptides according to invention are used to connect the C-terminus of the light chain to the N-terminus of heavy chain of the the second full length antibody (that specifically binds to a second antigen) via a peptide linker. The peptide linker within the second full length antibody heavy and light chain is a peptide with an amino acid sequence with a length of at least 30 amino acids, preferably with a length of 32 to 50 amino acids. In one the peptide linker is a peptide with an amino acid sequence with a length of 32 to 40 amino acids. In one embodiment said linker is (G×S)n with G=glycine, S=serine, (x=3, n=8, 9 or 10 and m=0, 1, 2 or 3) or (x=4 and n=6, 7 or 8 and m=0, 1, 2 or 3), preferably with x=4, n=6 or 7 and m=0, 1, 2 or 3, more preferably with x=4, n=7 and m=2. In one embodiment said linker is $(G_4S)_6G_2$. Preferably the CH3 domains of the bispecific antibody according to the invention can be altered by the "knob-into-holes" technology which is described in detail with several examples in e.g. WO 96/027011, Ridgway J. B., et al., Protein Eng 9 (1996) 617-621; and Merchant, A. M., et al., Nat Biotechnol 16 (1998) 677-681. In this method the interaction surfaces of the two CH3 domains are altered to increase the heterodimerisation of both heavy chains containing these two CH3 domains. Each of the two CH3 domains (of the two heavy chains) can be the "knob", while the other is the "hole". The introduction of a disulfide bridge stabilizes the heterodimers (Merchant, A. M, et al., Nature Biotech 16 (1998) 677-681; Atwell, S., et al. J. Mol. Biol. 270 (1997) 26-35) and increases the yield.

In one aspect of the invention the bispecific antibody according to the invention is further is characterized in that
the CH3 domain of one heavy chain and the CH3 domain of the other heavy chain each meet at an interface which comprises an original interface between the antibody CH3 domains;
wherein said interface is altered to promote the formation of the bispecific antibody, wherein the alteration is characterized in that:
a) the CH3 domain of one heavy chain is altered,
so that within the original interface the CH3 domain of one heavy chain that meets the original interface of the CH3 domain of the other heavy chain within the bispecific antibody,
an amino acid residue is replaced with an amino acid residue having a larger side chain volume, thereby generating a protuberance within the interface of the CH3 domain of one heavy chain which is positionable in a cavity within the interface of the CH3 domain of the other heavy chain and
b) the CH3 domain of the other heavy chain is altered,
so that within the original interface of the second CH3 domain that meets the original interface of the first CH3 domain within the bispecific antibody an amino acid residue is replaced with an amino acid residue having a smaller side chain volume, thereby generating a cavity within the interface of the second CH3 domain within which a protuberance within the interface of the first CH3 domain is positionable.

Thus the antibody according to invention is preferably characterized in that the CH3 domain of the heavy chain of the full length antibody of a) and the CH3 domain of the heavy chain of the full length antibody of b) each meet at an interface which comprises an alteration in the original interface between the antibody CH3 domains;

wherein i) in the CH3 domain of one heavy chain an amino acid residue is replaced with an amino acid residue having a larger side chain volume, thereby generating a protuberance within the interface of the CH3 domain of one heavy chain which is positionable in a cavity within the interface of the CH3 domain of the other heavy chain and wherein ii) in the CH3 domain of the other heavy chain an amino acid residue is replaced with an amino acid residue having a smaller side chain volume, thereby generating a cavity within the interface of the second CH3 domain within which a protuberance within the interface of the first CH3 domain is positionable.

Preferably said amino acid residue having a larger side chain volume is selected from the group consisting of arginine (R), phenylalanine (F), tyrosine (Y), tryptophan (W).

Preferably said amino acid residue having a smaller side chain volume is selected from the group consisting of alanine (A), serine (S), threonine (T), valine (V).

In one aspect of the invention both CH3 domains are further altered by the introduction of cysteine (C) as amino acid in the corresponding positions of each CH3 domain such that a disulfide bridge between both CH3 domains can be formed.

In one embodiment, the bispecific antibody comprises a T366W mutation in the

CH3 domain of the "knobs chain" and T366S, L368A, Y407V mutations in the CH3 domain of the "hole chain". An additional interchain disulfide bridge between the CH3 domains can also be used (Merchant, A. M, et al., Nature Biotech 16 (1998) 677-681) e.g. by introducing a Y349C mutation into the CH3 domain of the "knobs chain" and a E356C mutation or a S354C mutation into the CH3 domain of the "hole chain".

In another embodiment, the bispecific antibody according to the invention comprises Y349C, T366W mutations in one of the two CH3 domains and E356C, T366S, L368A, Y407V mutations in the other of the two CH3 domains. In a another preferred embodiment the bispecific antibody comprises Y349C, T366W mutations in one of the two CH3 domains and S354C, T366S, L368A, Y407V mutations in the other of the two CH3 domains (the additional Y349C mutation in one CH3 domain and the additional E356C or S354C mutation in the other CH3 domain forming a interchain disulfide bridge) (numbering always according to EU index of Kabat). But also other knobs-in-holes technologies as described by EP 1870459A1, can be used alternatively or additionally. Thus another example for the bispecific antibody are R409D; K370E mutations in the CH3 domain of the "knobs chain" and D399K; E357K mutations in the CH3 domain of the "hole chain" (numbering always according to EU index of Kabat).

In another embodiment the bispecific antibody comprises a T366W mutation in the CH3 domain of the "knobs chain" and T366S, L368A, Y407V mutations in the CH3 domain of the "hole chain" and additionally R409D; K370E mutations in the CH3 domain of the "knobs chain" and D399K; E357K mutations in the CH3 domain of the "hole chain".

In another embodiment the bispecific antibody comprises Y349C, T366W mutations in one of the two CH3 domains and S354C, T366S, L368A, Y407V mutations in the other of the two CH3 domains or said trivalent, bispecific antibody comprises Y349C, T366W mutations in one of the two CH3 domains and S354C, T366S, L368A, Y407V mutations in the other of the two CH3 domains and additionally R409D; K370E mutations in the CH3 domain of the "knobs chain" and D399K; E357K mutations in the CH3 domain of the "hole chain".

In one embodiment the antibody heavy chain variable domain (VH) and the antibody light chain variable domain (VL) of the heavy and light chain of the second full length antibody (that specifically binds to a second antigen) are disulfide stabilized by introduction of a disulfide bond between the following positions:

i) heavy chain variable domain position 44 to light chain variable domain position 100, ii) heavy chain variable domain position 105 to light chain variable domain position 43, or iii) heavy chain variable domain position 101 to light chain variable domain position 100 (numbering always according to EU index of Kabat).

In one embodiment the antibody heavy chain variable domain (VH) and the antibody light chain variable domain (VL) of the heavy and light chain of the second full length antibody (that specifically binds to a second antigen) are disulfide stabilized by introduction of a disulfide bond between the following positions: heavy chain variable domain position 44 to light chain variable domain position 100.

Such further disulfide stabilization is achieved by the introduction of a disulfide bond between the variable domains VH and VL of the second full length antibody heavy and light chain. Techniques to introduce unnatural disulfide bridges for stabilization for a single chain Fv are described e.g. in WO 94/029350, Rajagopal, V., et al, Prot. Engin. 10 (1997) 1453-59; Kobayashi, H., et al., Nuclear Medicine & Biology, Vol. 25, (1998) 387-393; or Schmidt, M., et al., Oncogene (1999) 18, 1711-1721. In one embodiment the optional disulfide bond between the variable domains of the second full length antibody heavy and light chain is between heavy chain variable domain position 44 and light chain variable domain position 100. In one embodiment the optional disulfide bond between the variable domains is between heavy chain variable domain position 105 and light chain variable domain position 43 (numbering always according to EU index of Kabat).

In one embodiment a bispecific antibody according to the invention with said optional disulfide stabilization between the variable domains VH and VL of the second full length antibody heavy and light chain is preferred.

In one embodiment a bispecific antibody according to the invention without said optional disulfide stabilization between the variable domains VH and VL of the second full length antibody heavy and light chain is preferred.

Both parts of the bispecific antibody according to the invention comprise antigen-binding sites (the first full length antibody heavy and light chain comprise one antigen binding site, and the second full length antibody heavy and light chain comprise one antigen binding site). The terms "binding site" or "antigen-binding site" as used herein denotes the region(s) of said bispecific antibody according to the invention to which the respective antigen actually binds. The antigen binding sites either in the first full length antibody heavy and light chain and the second full length antibody heavy and light chain are formed each by a pair consisting of an antibody light chain variable domain (VL) and an antibody heavy chain variable domain (VH).

The antigen-binding sites that bind to the desired antigen (e.g EGFR) can be derived a) from known antibodies to the antigen (e.g anti-EGFR antibodies) or b) from new antibodies or antibody fragments obtained by de novo immunization methods using inter alia either the antigen protein or nucleic acid or fragments thereof or by phage display.

An antigen-binding site of an antibody of the invention contains six complementarity determining regions (CDRs) which contribute in varying degrees to the affinity of the binding site for antigen. There are three heavy chain variable domain CDRs (CDRH1, CDRH2 and CDRH3) and three light chain variable domain CDRs (CDRL1, CDRL2 and CDRL3). The extent of CDR and framework regions (FRs) is determined by comparison to a compiled database of amino acid sequences in which those regions have been defined according to variability among the sequences.

Antibody specificity refers to selective recognition of the antibody for a particular epitope of an antigen. Natural antibodies, for example, are monospecific. The term "bispecific" antibody as used herein denotes an antibody that has two or more anigen-binding sites and binds to two different antigens or two different epitopes of the same antigen. "Bispecific antibodies" according to the invention are antibodies which have two different antigen-binding specificities. In one embodiment antibodies of the present invention are bispecific for two different antigens, i.e. VEGF as first antigen and ANG-2 as second antigen or e.g. EGFR as first antigen and IGF-1R as second antigen, or vice versa.

The term "monospecific" antibody as used herein denotes an antibody that has one or more binding sites each of which bind to the same epitope of the same antigen.

The term "valent" as used within the current application denotes the presence of a specified number of binding sites in an antibody molecule. As such, the terms "trivalent", "tetravalent", "pentavalent" and "hexavalent" denote the presence of three binding sites, four binding sites, five binding sites, and six binding sites, respectively, in an antibody molecule. A natural antibody for example or a bispecific antibody according to the invention has two binding sites and is bivalent.

The term "EGFR" as used herein refers to human epidermal growth factor receptor (also known as HER-1 or Erb-B1, SEQ ID NO: 13) is a 170 kDa transmembrane receptor encoded by the c-erbB proto-oncogene, and exhibits intrinsic tyrosine kinase activity (Modjtahedi, H., et al., Br. J. Cancer 73 (1996) 228-235; Herbst, R. S., and Shin, D. M., Cancer 94 (2002) 1593-1611). SwissProt database entry P00533 provides the sequence of EGFR. There are also isoforms and variants of EGFR (e.g., alternative RNA transcripts, truncated versions, polymorphisms, etc.) including but not limited to those identified by Swissprot database entry numbers P00533-1, P00533-2, P00533-3, and P00533-4. EGFR is known to bind ligands including α), epidermal growth factor (EGF), transforming growth factor-α (TGf-amphiregulin, heparin-binding EGF (hb-EGF), betacellulin, and epiregulin (Herbst, R. S., and Shin, D. M., Cancer 94 (2002) 1593-1611; Mendelsohn, J., and Baselga, J., Oncogene 19 (2000) 6550-6565). EGFR regulates numerous cellular processes via tyrosine-kinase mediated signal transduction pathways, including, but not limited to, activation of signal transduction pathways that control cell proliferation, differentiation, cell survival, apoptosis, angiogenesis, mitogenesis, and metastasis (Atalay, G., et al., Ann. Oncology 14 (2003) 1346-1363; Tsao, A. S., and Herbst, R. S., Signal 4 (2003) 4-9; Herbst, R. S., and Shin, D. M., Cancer 94 (2002) 1593-1611; Modjtahedi, H., et al., Br. J. Cancer 73 (1996) 228-235).

The term "IGF-1R" as used herein refers to human Insulin-like growth factor I receptor (IGF-IR, CD 221 antigen; SEQ ID NO: 14) belongs to the family of transmembrane protein tyrosine kinases (LeRoith, D., et al., Endocrin. Rev. 16 (1995) 143-163; and Adams, T. E., et al., Cell. Mol. Life Sci. 57 (2000) 1050-1063). SwissProt database entry P08069 provides the sequence of IGF-1R. IGF-IR binds IGF-I with high affinity and initiates the physiological response to this ligand in vivo. IGF-IR also binds to IGF-II, however with slightly lower affinity. IGF-IR overexpression promotes the neoplastic transformation of cells and there exists evidence that IGF-IR is involved in malignant transformation of cells and is therefore a useful target for the development of therapeutic agents for the treatment of cancer (Adams, T. E., et al., Cell. Mol. Life Sci. 57 (2000) 1050-1063).

In a preferred aspect of the invention the bispecific antibody according to the invention specifically binds to human IGF-1R as well as to human EGFR (i.e. the bispecific antibody according to the invention is a bispecific anti-IGF-1R/anti-EGFR antibody). The bispecific antibody is based on the antigen-binding sites of human <IGF-1R> HUMAB Clone 18 (DSM ACC 2587; WO 2005/005635, abbreviated as <IGF-1R>Clone18 or <IGF-1R> AK18) and humanized <EGFR>ICR62 (WO 2006/082515 abbreviated as <EGFR>ICR62). The relevant light and heavy chain amino acid sequences of these bispecific, bivalent antibodies are given in SEQ ID NO: 1, SEQ ID NO: 2, SEQ ID NO: 3 (for OA-Ak18-scFab-GA201); in SEQ ID NO: 5, SEQ ID NO: 6, SEQ ID NO: 7 (for OA-GA201-scFab-Ak18); in SEQ ID NO: 1, SEQ ID NO: 2, SEQ ID NO: 4 (for OA-Ak18-scFab-GA201_WT), and in SEQ ID NO: 5, SEQ ID NO: 6, SEQ ID NO: 8 (for OA-GA201-scFab-Ak18_WT).

The bispecific <EGFR-IGF-1R> antibodies according to the invention show benefits for human patients in need of a EGFR and IGF-1R targeting therapy. The antibodies according to the invention have highly valuable properties causing a benefit for a patient suffering from such a disease, especially suffering from cancer. The bispecific <EGFR-IGF-1R> antibodies according to the invention show e.g. a reduction of the internalization of IGF-1R receptor compared to the monospecific parent <IGF-1R> antibody. Furthermore they show good targeting of tumor cells expressing both antigens EGFR and IGF-1R which represents a benefit with respect to the efficacy/toxicity ratio for patients suffering from a cancer expressing both antigens EGFR and IGF-1R.

Thus in one aspect of the invention the bispecific antibody according to the invention is characterized in that
a) the first full length antibody specifically binds to IGF-1R and comprises a heavy chain with the amino acid sequence of SEQ ID NO: 1, and a light chain with the amino acid sequence of SEQ ID NO: 2, and
b) the second full length antibody specifically binds to EGFR and comprises a heavy chain connected to the light chain via a peptide linker wherein said connected heavy and light chain have the amino acid sequence of SEQ ID NO: 3.

In another aspect of the invention the bispecific antibody according to the invention is characterized in that
a) the first full length antibody specifically binds to IGF-1R and comprises a heavy chain with the amino acid sequence of SEQ ID NO: 1, and a light chain with the amino acid sequence of SEQ ID NO: 2, and
b) the second full length antibody specifically binds to EGFR and comprises a heavy chain connected to the light chain via a peptide linker wherein said connected heavy and light chain have the amino acid sequence of SEQ ID NO: 4.

In another aspect of the invention the bispecific antibody according to the invention is characterized in that
a) the first full length antibody specifically binds to EGFR and comprises a heavy chain with the amino acid sequence of SEQ ID NO: 5, and a light chain with the amino acid sequence of SEQ ID NO: 6, and
b) the second full length antibody specifically binds to IGF-1R and comprises a heavy chain connected to the light chain via a peptide linker wherein said connected heavy and light chain have the amino acid sequence of SEQ ID NO: 7.

In another aspect of the invention the bispecific antibody according to the invention is characterized in that
a) the first full length antibody specifically binds to EGFR and comprises a heavy chain with the amino acid sequence of SEQ ID NO: 5, and a light chain with the amino acid sequence of SEQ ID NO: 6, and
b) the second full length antibody specifically binds to IGF-1R and comprises a heavy chain connected to the light chain via a peptide linker wherein said connected heavy and light chain have the amino acid sequence of SEQ ID NO: 8.

Thus in one embodiment of the invention the bispecific antibody is an anti-IGF-1R/anti-EGFR antibody and is characterized in comprising the amino acid sequences of SEQ ID NO: 1, of SEQ ID NO: 2, and of SEQ ID NO: 3. 22. Accordingly one aspect of the invention is a bispecific antibody that specifically binds to human IGF-1R and to human EGFR, characterized in comprising the amino acid sequences of SEQ ID NO: 1, of SEQ ID NO: 2, and of SEQ ID NO: 3.

Thus in one embodiment of the invention the bispecific antibody is an anti-IGF-1R/anti-EGFR antibody and is characterized in comprising the amino acid sequences of SEQ ID NO: 1, of SEQ ID NO: 2, and of SEQ ID NO: 4. Accordingly one aspect of the invention is a bispecific antibody that specifically binds to human IGF-1R and to human EGFR, characterized in comprising the amino acid sequences of SEQ ID NO: 1, of SEQ ID NO: 2, and of SEQ ID NO: 4.

Thus in one embodiment of the invention the bispecific antibody is an anti-IGF-1R/anti-EGFR antibody and is characterized in comprising the amino acid sequences of SEQ ID NO: 5, of SEQ ID NO: 6, and of SEQ ID NO: 7. Accordingly one aspect of the invention is a bispecific antibody that specifically binds to human IGF-1R and to human EGFR, characterized in comprising the amino acid sequences of SEQ ID NO: 5, of SEQ ID NO: 6, and of SEQ ID NO: 7.

Thus in one embodiment of the invention the bispecific antibody is an anti-IGF-1R/anti-EGFR antibody and is characterized in comprising the amino acid sequences of SEQ ID NO: 5, of SEQ ID NO: 6, and of SEQ ID NO: 8. Accordingly one aspect of the invention is a bispecific antibody that specifically binds to human IGF-1R and to human EGFR, characterized in comprising the amino acid sequences of SEQ ID NO: 5, of SEQ ID NO: 6, and of SEQ ID NO: 8.

In one embodiment of the invention the bispecific antibody is an anti-IGF-1R/anti-EGFR antibody and is characterized in
a) comprising the amino acid sequences of SEQ ID NO: 1, of SEQ ID NO: 2, and of SEQ ID NO: 3.
b) comprising the amino acid sequences of SEQ ID NO: 1, of SEQ ID NO: 2, and of SEQ ID NO: 4.
c) comprising the amino acid sequences of SEQ ID NO: 5, of SEQ ID NO: 6, and of SEQ ID NO: 7, or
d) comprising the amino acid sequences of SEQ ID NO: 5, of SEQ ID NO: 6, and of SEQ ID NO: 8.

In one embodiment of the invention said bispecific antibody anti-IGF-1R/anti-EGFR antibody is characterized in having one or more of the following properties (determined in assays as described in Example 4 and 5):
the anti-IGF-1R/anti-EGFR antibody inhibits the phosphorylation of IGF-1R with an IC50 of 5 nM or less (preferably 2 nM or less) on H322M tumor cells;
the bispecific anti-IGF-1R/anti-EGFR antibody inhibits the phosphorylation of EGFR with an IC50 of 5 nM or less (preferably 2 nM or less) on H322M tumor cells;
the bispecific anti-IGF-1R/anti-EGFR antibody reduces the downregulation of IGF-1R by 50% or more compared to the anti-IGF-1R antibody <IGF-1R> HUMAB Clone 18 (DSM ACC 2587).

In another aspect of the invention the bispecific antibody according to the invention is characterized in that
a) the first full length antibody specifically binds to EGFR and comprises a heavy chain with the amino acid sequence of SEQ ID NO: 5, and a light chain with the amino acid sequence of SEQ ID NO: 6, and
b) the second full length antibody specifically binds to IGF-1R and comprises a heavy chain connected to the light chain via a peptide linker wherein said connected heavy and light chain have the amino acid sequence of SEQ ID NO: 7 with no more than 1 amino acid residue substitutions in the CDRs, and wherein the KD value of binding affinity is equal or is reduced less than 4 fold when compared to the KD value of binding affinity of unmutated amino acid sequence of SEQ ID NO: 7.

In another aspect of the invention the bispecific antibody according to the invention is characterized in that
a) the first full length antibody specifically binds to EGFR and comprises a heavy chain with the amino acid sequence of SEQ ID NO: 5, and a light chain with the amino acid sequence of SEQ ID NO: 6, and
b) the second full length antibody specifically binds to IGF-1R and comprises a heavy chain connected to the light chain via a peptide linker wherein said connected heavy and light chain have the amino acid sequence of SEQ ID NO: 8 with no more than 1 amino acid residue substitutions in the CDRs, and wherein the KD value of binding affinity is equal or is reduced less than 4 fold when compared to the KD value of binding affinity of unmutated amino acid sequence of SEQ ID NO: 8.

In another aspect of the invention the bispecific antibody according to the invention is characterized in that
a) the first full length antibody specifically binds to EGFR and comprises a heavy chain with the amino acid sequence of SEQ ID NO: 5, and a light chain with the amino acid sequence of SEQ ID NO: 6, and
b) the second full length antibody specifically binds to IGF-1R and comprises a heavy chain connected to the light chain via a peptide linker wherein said connected heavy and light chain have the amino acid sequence of SEQ ID NO: 7 with no more than 1 amino acid residue substitutions in the CDR3H, and wherein the KD value of binding affinity is equal or is reduced less than 4 fold when compared to the KD value of binding affinity of unmutated amino acid sequence of SEQ ID NO: 7.

In another aspect of the invention the bispecific antibody according to the invention is characterized in that
a) the first full length antibody specifically binds to EGFR and comprises a heavy chain with the amino acid sequence of SEQ ID NO: 5, and a light chain with the amino acid sequence of SEQ ID NO: 6, and
b) the second full length antibody specifically binds to IGF-1R and comprises a heavy chain connected to the light chain via a peptide linker wherein said connected heavy and light chain have the amino acid sequence of SEQ ID NO: 8 with no more than 1 amino acid residue substitutions in the CDR3H, and wherein the KD value of binding affinity is equal or is reduced less than 4 fold when compared to the KD value of binding affinity of unmutated amino acid sequence of SEQ ID NO: 8.

In another aspect of the invention the bispecific antibody according to the invention is characterized in that
a) the first full length antibody specifically binds to EGFR and comprises a heavy chain with the amino acid sequence of SEQ ID NO: 5, and a light chain with the amino acid sequence of SEQ ID NO: 6, and
b) the second full length antibody specifically binds to IGF-1R and comprises a heavy chain connected to the light chain via a peptide linker wherein said connected heavy and light chain have the amino acid sequence of SEQ ID NO: 7 with no more than 1 amino acid residue substitutions in the CDRs, and wherein the KD value of binding affinity is equal or is reduced less than 4 fold when compared to the KD value of binding affinity of unmutated amino acid sequence of SEQ ID NO: 7;
and having one or more of the following properties (determined in assays as described in Example 4 and 5):
the anti-IGF-1R/anti-EGFR antibody inhibits the phosphorylation of IGF-1R with an IC50 of 5 nM or less (preferably 2 nM or less) on H322M tumor cells
the bispecific anti-IGF-1R/anti-EGFR antibody inhibits the phosphorylation of EGFR with an IC50 of 5 nM or less (preferably 2 nM or less) on H322M tumor cells
the bispecific anti-IGF-1R/anti-EGFR antibody reduces the downregulation of IGF-1R by 50% or more compared to the anti-IGF-1R antibody <IGF-1R> HUMAB Clone 18 (DSM ACC 2587).

In another aspect of the invention the bispecific antibody according to the invention is characterized in that
a) the first full length antibody specifically binds to EGFR and comprises a heavy chain with the amino acid sequence of SEQ ID NO: 5, and a light chain with the amino acid sequence of SEQ ID NO: 6, and
b) the second full length antibody specifically binds to IGF-1R and comprises a heavy chain connected to the light chain via a peptide linker wherein said connected heavy and light chain have the amino acid sequence of SEQ ID NO: 8 with no more than 1 amino acid residue substitutions in the CDRs, and wherein the KD value of binding affinity is equal or is reduced less than 4 fold when compared to the KD value of binding affinity of unmutated amino acid sequence of SEQ ID NO: 8;
and having one or more of the following properties (determined in assays as described in Example 4 and 5):
the anti-IGF-1R/anti-EGFR antibody inhibits the phosphorylation of IGF-1R with an IC50 of 5 nM or less (preferably 2 nM or less) on H322M tumor cells
the bispecific anti-IGF-1R/anti-EGFR antibody inhibits the phosphorylation of EGFR with an IC50 of 5 nM or less (preferably 2 nM or less) on H322M tumor cells
the bispecific anti-IGF-1R/anti-EGFR antibody reduces the downregulation of IGF-1R by 50% or more compared to the anti-IGF-1R antibody <IGF-1R> HUMAB Clone 18 (DSM ACC 2587).

In another aspect of the invention the bispecific antibody according to the invention is characterized in that
a) the first full length antibody specifically binds to EGFR and comprises a heavy chain with the amino acid sequence of SEQ ID NO: 5, and a light chain with the amino acid sequence of SEQ ID NO: 6, and
b) the second full length antibody specifically binds to IGF-1R and comprises a heavy chain connected to the light chain via a peptide linker wherein said connected heavy and light chain have the amino acid sequence of SEQ ID NO: 7 with no more than 1 amino acid residue substitutions in the CDR3H, and wherein the KD value of binding affinity is equal or is reduced less than 4 fold when compared to the KD value of binding affinity of unmutated amino acid sequence of SEQ ID NO: 7;
and having one or more of the following properties (determined in assays as described in Example 4 and 5):
the anti-IGF-1R/anti-EGFR antibody inhibits the phosphorylation of IGF-1R with an IC50 of 5 nM or less (preferably 2 nM or less) on H322M tumor cells
the bispecific anti-IGF-1R/anti-EGFR antibody inhibits the phosphorylation of EGFR with an IC50 of 5 nM or less (preferably 2 nM or less) on H322M tumor cells
the bispecific anti-IGF-1R/anti-EGFR antibody reduces the downregulation of IGF-1R by 50% or more compared to the anti-IGF-1R antibody <IGF-1R> HUMAB Clone 18 (DSM ACC 2587).

In another aspect of the invention the bispecific antibody according to the invention is characterized in that
a) the first full length antibody specifically binds to EGFR and comprises a heavy chain with the amino acid sequence of SEQ ID NO: 5, and a light chain with the amino acid sequence of SEQ ID NO: 6, and
b) the second full length antibody specifically binds to IGF-1R and comprises a heavy chain connected to the light chain via a peptide linker wherein said connected heavy and light chain have the amino acid sequence of SEQ ID NO: 8 with no more than 1 amino acid residue substitutions in the CDR3H, and wherein the KD value of binding affinity is equal or is reduced less than 4 fold when compared to the KD value of binding affinity of unmutated amino acid sequence of SEQ ID NO: 8;
and having one or more of the following properties (determined in assays as described in Example 4 and 5):
the anti-IGF-1R/anti-EGFR antibody inhibits the phosphorylation of IGF-1R with an IC50 of 5 nM or less (preferably 2 nM or less) on H322M tumor cells
the bispecific anti-IGF-1R/anti-EGFR antibody inhibits the phosphorylation of EGFR with an IC50 of 5 nM or less (preferably 2 nM or less) on H322M tumor cells
the bispecific anti-IGF-1R/anti-EGFR antibody reduces the downregulation of IGF-1R by 50% or more compared to the anti-IGF-1R antibody <IGF-1R> HUMAB Clone 18 (DSM ACC 2587).

Examples of amino acid residue substitutions in the CDR3H of SEQ ID NO: 7 or of SEQ ID NO: 8 wherein the KD value of binding affinity is equal or is reduced less than 4 fold when compared to the KD value of binding affinity of unmutated amino acid sequence, are described e.g in EP10166860.6.

The term "VEGF" as used herein refers to human vascular endothelial growth factor (VEGF/VEGF-A) (SEQ ID No: 15) which is described in e.g. Leung, D. W., et al., Science 246 (1989) 1306-9; Keck, P. J., et al., Science 246 (1989) 1309-12 and Connolly, D. T., et al., J. Biol. Chem. 264 (1989) 20017-24. VEGF is involved in the regulation of normal and abnormal angiogenesis and neovascularization associated with tumors and intraocular disorders (Ferrara, N., et al., Endocr. Rev. 18 (1997) 4-25; Berkman, R. A., et al., J. Clin. Invest. 91 (1993) 153-159; Brown, L. F., et al., Human Pathol. 26 (1995) 86-91; Brown, L. F., et al., Cancer Res. 53 (1993) 4727-4735; Mattern, J., et al., Brit. J. Cancer. 73 (1996) 931-934; and Dvorak, H., et al., Am. J. Pathol. 146 (1995) 1029-1039). VEGF is a homodimeric glycoprotein that has been isolated from several sources. VEGF shows highly specific mitogenic activity for endothelial cells.

The term "ANG-2" as used herein refers to human angiopoietin-2 (ANG-2) (alternatively abbreviated with ANGPT2 or ANG2) (SEQ ID No: 16) which is described in Maisonpierre, P. C., et al, Science 277 (1997) 55-60 and Cheung, A. H., et al., Genomics 48 (1998) 389-91. The angiopoietins-1 and -2 and ANG-2 were discovered as ligands for the Ties, a family of tyrosine kinases that is selectively expressed within the vascular endothelium. Yancopoulos, G. D., et al., Nature 407 (2000) 242-48. There are now four definitive members of the angiopoietin family. Angiopoietin-3 and -4 (Ang-3 and Ang-4) may represent widely diverged counterparts of the same gene locus in mouse and man. Kim, I., et al., FEBS Let, 443 (1999) 353-56; Kim, I., et al., J Biol Chem 274 (1999) 26523-28. ANG-1 and ANG-2 were originally identified in tissue culture experiments as agonist and antagonist, respectively (see for ANG-1: Davis, S., et al., Cell 87 (1996) 1161-69; and for ANG-2: Maisonpierre, P. C., et al., Science 277 (1997) 55-60) All of the known angiopoietins bind primarily to Tie2, and both Ang-1 and -2 bind to Tie2 with an affinity of 3 nM (Kd). Maisonpierre, P. C., et al., Science 277 (1997) 55-60.

In a preferred embodiment said bispecific antibody according to the invention specifically binds to human VEGF as well as to human ANG-2 (i.e. the bispecific antibody according to the invention is a bispecific anti-VEGF/anti-ANG-2 antibody). The bispecific antibody preferably based on the antigen-binding sites of the anti-VEGF antibody bevacizumab and ANG2i-LCO6 (which is decribed in the WO2010/040508 (PCT application No. PCT/EP2009/007182) and which was obtained via phage display). The relevant light and heavy chain amino acid sequences of these bispecific, bivalent antibodies are given in SEQ ID NO: 9, SEQ ID NO: 10, SEQ ID NO: 11 (for Ang2-VEGF OA-Ava-N-scFabLCO6SS), and in SEQ ID NO: 9, SEQ ID NO: 10, SEQ ID NO: 12 (for Ang2-VEGF OA-Ava-N-scFabLC06).

Thus in one aspect of the invention the bispecific antibody according to the invention is characterized in that
a) the first full length antibody specifically binds to VEGF and comprises a heavy chain with the amino acid sequence of SEQ ID NO: 9, and a light chain with the amino acid sequence of SEQ ID NO: 10, and
b) the second full length antibody specifically binds to ANG-2 and comprises a heavy chain connected to the light chain via a peptide linker wherein said connected heavy and light chain have the amino acid sequence of SEQ ID NO: 11.

In another aspect of the invention the bispecific antibody according to the invention is characterized in that
a) the first full length antibody specifically binds to VEGF and comprises a heavy chain with the amino acid sequence of SEQ ID NO: 9, and a light chain with the amino acid sequence of SEQ ID NO: 10, and
b) the second full length antibody specifically binds to ANG-2 and comprises a heavy chain connected to the light chain via a peptide linker wherein said connected heavy and light chain have the amino acid sequence of SEQ ID NO: 12.

Thus in one embodiment of the invention the bispecific antibody is an anti-VEGF/anti-ANG-2 antibody and is characterized in comprising the amino acid sequences of SEQ ID NO: 9, of SEQ ID NO: 10, and of SEQ ID NO: 11.

Thus in one embodiment of the invention the bispecific antibody is an anti-VEGF/anti-ANG-2 antibody and is characterized in comprising the amino acid sequences of SEQ ID NO: 9, of SEQ ID NO: 10, and of SEQ ID NO: 12.

The full length antibodies of the invention comprise immunoglobulin constant regions of one or more immunoglobulin classes. Immunoglobulin classes include IgG, IgM, IgA, IgD, and IgE isotypes and, in the case of IgG and IgA, their subtypes. In a preferred embodiment, an full length antibody of the invention has a constant domain structure of an IgG type antibody.

The terms "monoclonal antibody" or "monoclonal antibody composition" as used herein refer to a preparation of antibody molecules of a single amino acid composition.

The term "chimeric antibody" refers to an antibody comprising a variable region, i.e., binding region, from one source or species and at least a portion of a constant region derived from a different source or species, usually prepared by recombinant DNA techniques. Chimeric antibodies comprising a murine variable region and a human constant region are preferred. Other preferred forms of "chimeric antibodies" encompassed by the present invention are those in which the constant region has been modified or changed from that of the original antibody to generate the properties according to the invention, especially in regard to C1q binding and/or Fc receptor (FcR) binding. Such chimeric antibodies are also referred to as "class-switched antibodies.". Chimeric antibodies are the product of expressed immunoglobulin genes comprising DNA segments encoding immunoglobulin variable regions and DNA segments encoding immunoglobulin constant regions. Methods for producing chimeric antibodies involve conventional recombinant DNA and gene transfection techniques are well known in the art. See, e.g., Morrison, S. L., et al., Proc. Natl. Acad. Sci. USA 81 (1984) 6851-6855; U.S. Pat. No. 5,202, 238 and U.S. Pat. No. 5,204,244.

The term "humanized antibody" refers to antibodies in which the framework or "complementarity determining regions" (CDR) have been modified to comprise the CDR of an immunoglobulin of different specificity as compared to that of the parent immunoglobulin. In a preferred embodiment, a murine CDR is grafted into the framework region of a human antibody to prepare the "humanized antibody." See, e.g., Riechmann, L., et al., Nature 332 (1988) 323-327; and Neuberger, M. S., et al., Nature 314 (1985) 268-270. Particularly preferred CDRs correspond to those representing sequences recognizing the antigens noted above for chimeric antibodies. Other forms of "humanized antibodies" encompassed by the present invention are those in which the constant region has been additionally modified or changed from that of the original antibody to generate the properties according to the invention, especially in regard to C1q binding and/or Fc receptor (FcR) binding.

The term "human antibody", as used herein, is intended to include antibodies having variable and constant regions derived from human germ line immunoglobulin sequences. Human antibodies are well-known in the state of the art (van Dijk, M. A., and van de Winkel, J. G., Curr. Opin. Chem. Biol. 5 (2001) 368-374). Human antibodies can also be produced in transgenic animals (e.g., mice) that are capable, upon immunization, of producing a full repertoire or a selection of human antibodies in the absence of endogenous immunoglobulin production. Transfer of the human germline immunoglobulin gene array in such germ-line mutant mice will result in the production of human antibodies upon antigen challenge (see, e.g., Jakobovits, A., et al., Proc. Natl. Acad. Sci. USA 90 (1993) 2551-2555; Jakobovits, A., et al., Nature 362 (1993) 255-258; Bruggemann, M., et al., Year Immunol. 7 (1993) 33-40). Human antibodies can also be produced in phage display libraries (Hoogenboom, H. R., and Winter, G., J. Mol. Biol. 227 (1992) 381-388; Marks, J. D., et al., J. Mol. Biol. 222 (1991) 581-597). The techniques of Cole, et al. and Boerner, et al., are also available for the preparation of human monoclonal antibodies (Cole, et al., Monoclonal Antibodies and Cancer Therapy, Alan R. Liss, p. 77 (1985); and Boerner, P., et al., J. Immunol. 147 (1991) 86-95). As already mentioned for chimeric and humanized antibodies according to the invention the term "human antibody" as used herein also comprises such antibodies which are modified in the constant region to generate the properties according to the invention, especially in regard to C1q binding and/or FcR binding, e.g. by "class switching" i.e. change or mutation of Fc parts (e.g. from IgG1 to IgG4 and/or IgG1/IgG4 mutation).

The term "recombinant human antibody", as used herein, is intended to include all human antibodies that are prepared, expressed, created or isolated by recombinant means, such as antibodies isolated from a host cell such as a NS0 or CHO cell or from an animal (e.g. a mouse) that is transgenic for human immunoglobulin genes or antibodies expressed using a recombinant expression vector transfected into a host cell. Such recombinant human antibodies have variable and constant regions in a rearranged form. The recombinant human antibodies according to the invention have been subjected to in vivo somatic hypermutation. Thus, the amino acid sequences of the VH and VL regions of the recombinant antibodies are sequences that, while derived from and related to human germ line VH and VL sequences, may not naturally exist within the human antibody germ line repertoire in vivo.

The "variable domain" (variable domain of a light chain (VL), variable region of a heavy chain (VH) as used herein denotes each of the pair of light and heavy chains which is involved directly in binding the antibody to the antigen. The domains of variable human light and heavy chains have the same general structure and each domain comprises four framework (FR) regions whose sequences are widely conserved, connected by three "hypervariable regions" (or complementarity determining regions, CDRs). The framework regions adopt a β-sheet conformation and the CDRs may form loops connecting the β-sheet structure. The CDRs in each chain are held in their three-dimensional structure by the framework regions and form together with the CDRs from the other chain the antigen binding site. The antibody heavy and light chain CDR3 regions play a particularly important role in the binding specificity/affinity of the antibodies according to the invention and therefore provide a further object of the invention.

The terms "hypervariable region" or "antigen-binding portion of an antibody" when used herein refer to the amino acid residues of an antibody which are responsible for antigen-binding. The hypervariable region comprises amino acid residues from the "complementarity determining regions" or "CDRs". "Framework" or "FR" regions are those variable domain regions other than the hypervariable region residues as herein defined. Therefore, the light and heavy chains of an antibody comprise from N- to C-terminus the domains FR1, CDR1, FR2, CDR2, FR3, CDR3, and FR4. CDRs on each chain are separated by such framework amino acids. Especially, CDR3 of the heavy chain is the region which contributes most to antigen binding. CDR and FR regions are determined according to the standard definition of Kabat et al., Sequences of Proteins of Immunological Interest, 5th ed., Public Health Service, National Institutes of Health, Bethesda, Md. (1991).

As used herein, the terms "binding to" or "which specifically binds to" or "specifically binding to" refers to the binding of the antibody to an epitope of the antigen in an in vitro assay, preferably in an plasmon resonance assay (BIACORE™, GE-Healthcare Uppsala, Sweden) with purified wild-type antigen. The affinity of the binding is defined by the terms ka (rate constant for the association of the antibody from the antibody/antigen complex), $k_D$ (dissociation constant), and $K_D$ ($k_D$/ka). In one embodiment binding or specifically binding means a binding affinity ($K_D$) of $10^{-8}$ mol/l or less, preferably $10^{-9}$ M to $10^{-13}$ mol/l. Thus, a bispecific antibody according to the invention is preferably specifically binding to each antigen for which it is specific with a binding affinity ($K_D$) of $10^{-8}$ mol/l or less, preferably $10^{-9}$ M to $10^{-13}$ mol/l.

Binding of the antibody to the FcγRIII can be investigated by a BIACORE™ assay (GE-Healthcare Uppsala, Sweden). The affinity of the binding is defined by the terms ka (rate constant for the association of the antibody from the antibody/antigen complex), $k_D$ (dissociation constant), and $K_D$ ($k_D$/ka).

The term "epitope" includes any polypeptide determinant capable of specific binding to an antibody. In certain embodiments, epitope determinant include chemically active surface groupings of molecules such as amino acids, sugar side chains, phosphoryl, or sulfonyl, and, in certain embodiments, may have specific three dimensional structural characteristics, and or specific charge characteristics. An epitope is a region of an antigen that is bound by an antibody.

In certain embodiments, an antibody is said to specifically bind an antigen when it preferentially recognizes its target antigen in a complex mixture of proteins and/or macromolecules.

The term "constant region" as used within the current applications denotes the sum of the domains of an antibody other than the variable region. The constant region is not involved directly in binding of an antigen, but exhibit various effector functions. Depending on the amino acid sequence of the constant region of their heavy chains, antibodies are divided in the classes: IgA, IgD, IgE, IgG and IgM, and several of these may be further divided into subclasses, such as IgG1, IgG2, IgG3, and IgG4, IgA1 and IgA2. The heavy chain constant regions that correspond to the different classes of antibodies are called α, δ, ε, γ, and μ, respectively. The light chain constant regions (CL) which can be found in all five antibody classes are called κ (kappa) and λ (lambda).

The term "constant region derived from human origin" as used in the current application denotes a constant heavy chain region of a human antibody of the subclass IgG1, IgG2, IgG3, or IgG4 and/or a constant light chain kappa or lambda region. Such constant regions are well known in the state of the art and e.g. described by Kabat, E. A., (see e.g. Johnson, G. and Wu, T. T., Nucleic Acids Res. 28 (2000) 214-218; Kabat, E. A., et al., Proc. Natl. Acad. Sci. USA 72 (1975) 2785-2788).

The term "complement-dependent cytotoxicity (CDC)" denotes a process initiated by binding of complement factor C1q to the Fc part of most IgG antibody subclasses. Binding of C1q to an antibody is caused by defined protein-protein interactions at the so called binding site. Such Fc part binding sites are known in the state of the art (see above). Such Fc part binding sites are, e.g., characterized by the amino acids L234, L235, D270, N297, E318, K320, K322, P331, and P329 (numbering according to EU index of Kabat). Antibodies of subclass IgG1, IgG2, and IgG3 usually show complement activation including C1q and C3 binding, whereas IgG4 does not activate the complement system and does not bind C1q and/or C3.

While antibodies of the IgG4 subclass show reduced Fc receptor (FcγRIIIa) binding, antibodies of other IgG subclasses show strong binding. However Pro238, Asp265, Asp270, Asn297 (loss of Fc carbohydrate), Pro329, Leu234, Leu235, Gly236, Gly237, Ile253, Ser254, Lys288, Thr307, Gln311, Asn434, and residues which, if altered, provide also reduced Fc receptor binding (Shields, R. L., et al., J. Biol. Chem. 276 (2001) 6591-6604; Lund, J., et al., FASEB J. 9 (1995) 115-119; Morgan, A., et al., Immunology 86 (1995) 319-324; EP 0 307 434).

In one embodiment an antibody according to the invention has a reduced FcR binding compared to an IgG1 antibody and the full length parent antibody is in regard to FcR binding of IgG4 subclass or of IgG1 or IgG2 subclass with a mutation in S228, L234, L235 and/or D265, and/or contains the PVA236 mutation. In one embodiment the mutations in the full length parent antibody are S228P, L234A, L235A, L235E and/or PVA236. In another embodiment the mutations in the full length parent antibody are in IgG4 S228P and L235E and in IgG1 L234A and L235A.

In a further embodiment the bispecific antibody according to the invention is characterized in that said full length antibody is of human IgG1 subclass.

The term "antibody-dependent cellular cytotoxicity (ADCC)" refers to lysis of human target cells by an antibody according to the invention in the presence of effector cells. ADCC is measured preferably by the treatment of a preparation of EGFR and IGF-1R expressing cells with an antibody according to the invention in the presence of effector cells such as freshly isolated PBMC or purified effector cells from buffy coats, like monocytes or natural killer (NK) cells or a permanently growing NK cell line.

The term "complement-dependent cytotoxicity (CDC)" denotes a process initiated by binding of complement factor C1q to the Fc part of most IgG antibody subclasses. Binding of C1q to an antibody is caused by defined protein-protein interactions at the so called binding site. Such Fc part binding sites are known in the state of the art (see above). Such Fc part binding sites are, e.g., characterized by the amino acids L234, L235, D270, N297, E318, K320, K322, P331, and P329 (numbering according to EU index of Kabat). Antibodies of subclass IgG1, IgG2, and IgG3 usually show complement activation including C1q and C3 binding, whereas IgG4 does not activate the complement system and does not bind C1q and/or C3.

The constant region of an antibody is directly involved in ADCC (antibody-dependent cell-mediated cytotoxicity) and CDC (complement-dependent cytotoxicity). Complement activation (CDC) is initiated by binding of complement factor C1q to the constant region of most IgG antibody subclasses. Binding of C1q to an antibody is caused by defined protein-protein interactions at the so called binding site. Such constant region binding sites are known in the state of the art and described e.g. by Lukas, T. J., et al., J. Immunol. 127 (1981) 2555-2560; Brunhouse, R., and Cebra, J. J., Mol. Immunol. 16 (1979) 907-917; Burton, D. R., et al., Nature 288 (1980) 338-344; Thommesen, J. E., et al., Mol. Immunol. 37 (2000) 995-1004; Idusogie, E. E., et al., J. Immunol. 164 (2000) 4178-4184; Hezareh, M., et al., J. Virol. 75 (2001) 12161-12168; Morgan, A., et al., Immunology 86 (1995) 319-324; and EP 0 307 434. Such constant region binding sites are, e.g., characterized by the amino acids L234, L235, D270, N297, E318, K320, K322, P331, and P329 (numbering according to EU index of Kabat).

In one embodiment the bispecific antibodies according to the invention comprise a constant region of IgG1 or IgG3 subclass (preferably of IgG1 subclass), which is preferably derived from human origin. In one embodiment the bispecific antibodies according to the invention comprise a Fc part of IgG1 or IgG3 subclass (preferably of IgG1 subclass), which is preferably derived from human origin.

Antibody-dependent cell-mediated cytotoxicity (ADCC) of monoclonal antibodies can be enhanced by engineering their oligosaccharide component as described in Umana, P., et al., Nature Biotechnol. 17 (1999) 176-180, and U.S. Pat. No. 6,602,684. IgG1 type antibodies, the most commonly used therapeutic antibodies, are glycoproteins that have a conserved N-linked glycosylation site at Asn297 in each CH2 domain. The two complex biantennary oligosaccharides attached to Asn297 are buried between the CH2 domains, forming extensive contacts with the polypeptide backbone, and their presence is essential for the antibody to mediate effector functions such as antibody dependent cellular cytotoxicity (ADCC) (Lifely, M. R., et al., Glycobiology 5 (1995) 813-822; Jefferis, R., et al., Immunol. Rev. 163 (1998) 59-76; Wright, A., and Morrison, S. L., Trends Biotechnol. 15 (1997) 26-32). Umana, P., et al. Nature Biotechnol. 17 (1999) 176-180 and WO 99/154342 showed that overexpression in Chinese hamster ovary (CHO) cells of β(1,4)-N-acetylglucosaminyltransferase III ("GnTIII"), a glycosyltransferase catalyzing the formation of bisected oligosaccharides, significantly increases the in vitro ADCC activity of antibodies. Alterations in the composition of the Asn297 carbohydrate or its elimination affect also binding to FcγR and C1q (Umana, P., et al., Nature Biotechnol. 17 (1999) 176-180; Davies, J., et al., Biotechnol. Bioeng. 74 (2001) 288-294; Mimura, Y., et al., J. Biol. Chem. 276 (2001) 45539-45547; Radaev, S., et al., J. Biol. Chem. 276 (2001) 16478-16483; Shields, R. L., et al., J. Biol. Chem. 276 (2001) 6591-6604; Shields, R. L., et al., J. Biol. Chem. 277 (2002) 26733-26740; Simmons, L. C., et al., J. Immunol. Methods 263 (2002) 133-147).

Methods to enhance cell-mediated effector functions of monoclonal antibodies by reducing the amount of fucose are described e.g. in WO 2005/018572, WO 2006/116260, WO 2006/114700, WO 2004/065540, WO 2005/011735, WO 2005/027966, WO 1997/028267, US 2006/0134709, US 2005/0054048, US 2005/0152894, WO 2003/035835, WO 2000/061739, Niwa, R., et al., J. Immunol. Methods 306 (2005) 151-160; Shinkawa, T., et al., J Biol Chem, 278 (2003) 3466-3473; WO 03/055993 or US 2005/0249722.

Glycosylation of human IgG1 or IgG3 occurs at Asn297 as core fucosylated biantennary complex oligosaccharide glycosylation terminated with up to two Gal residues. Human constant heavy chain regions of the IgG1 or IgG3 subclass are reported in detail by Kabat, E. A., et al., Sequences of Proteins of Immunological Interest, 5th Ed. Public Health Service, National Institutes of Health, Bethesda, Md. (1991), and by Brüggemann, M., et al., J. Exp. Med. 166 (1987) 1351-1361; Love, T. W., et al., Methods Enzymol. 178 (1989) 515-527. These structures are designated as G0, G1 (α-1,6- or α-1,3-), or G2 glycan residues, depending from the amount of terminal Gal residues (Raju, T. S., Bioprocess Int. 1 (2003) 44-53). CHO type glycosylation of antibody Fc parts is e.g. described by Routier, F. H., Glycoconjugate J. 14 (1997) 201-207. Antibodies which are recombinantly expressed in non-glycomodified CHO host cells usually are fucosylated at Asn297 in an amount of at least 85%. The modified oligosaccharides of the full length parent antibody may be hybrid or complex. Preferably the bisected, reduced/not-fucosylated oligosaccharides are hybrid. In another embodiment, the bisected, reduced/not-fucosylated oligosaccharides are complex.

According to the invention "amount of fucose" means the amount of said sugar within the sugar chain at Asn297, related to the sum of all glycostructures attached to Asn297 (e.g. complex, hybrid and high mannose structures) measured by MALDI-TOF mass spectrometry and calculated as average value. The relative amount of fucose is the percentage of fucose-containing structures related to all glycostructures identified in an N-Glycosidase F treated sample (e.g. complex, hybrid and oligo- and high-mannose structures, resp.) by MALDI-TOF (see Example 10).

The bispecific <EGFR-IGF-1R> antibodies according to the invention show a reduction of the internalization of EGFR and IGF-1R receptor compared to their parent <EGFR> and/or <IGF-1R> antibodies. Therefore in one preferred embodiment of the invention, the bispecific <EGFR-IGF-1R> antibody is glycosylated (IgG1 or IgG3 subclass, preferably IgG1 subclass) with a sugar chain at Asn297 whereby the amount of fucose within said sugar chain is 65% or lower (Numbering according to Kabat). In another embodiment is the amount of fucose within said sugar chain is between 5% and 65%, preferably between 20% and 40%. "Asn297" according to the invention means amino acid asparagine located at about position 297 in the Fc region. Based on minor sequence variations of antibodies, Asn297 can also be located some amino acids (usually not more than ±3 amino acids) upstream or downstream of position 297, i.e. between position 294 and 300. Such glycoengineered antibodies are also refer to as afocusylated antibodies herein.

The afucosylated bispecific antibody according to the invention can be expressed in a glycomodified host cell engineered to express at least one nucleic acid encoding a polypeptide having GnTIII activity in an amount sufficient to partially fucosylate the oligosaccharides in the Fc region. In one embodiment, the polypeptide having GnTIII activity is a fusion polypeptide. Alternatively α1,6-fucosyltransferase activity of the host cell can be decreased or eliminated according to U.S. Pat. No. 6,946,292 to generate glycomodified host cells. The amount of antibody fucosylation can be predetermined e.g. either by fermentation conditions (e.g. fermentation time) or by combination of at least two antibodies with different fucosylation amount. Such afucosylated antibodies and respective glycoengineering methods are described in WO 2005/044859, WO 2004/065540, WO2007/031875, Umana, P., et al., Nature Biotechnol. 17 (1999) 176-180, WO 99/154342, WO 2005/018572, WO 2006/116260, WO 2006/114700, WO 2005/011735, WO 2005/027966, WO 97/028267, US 2006/0134709, US 2005/0054048, US 2005/0152894, WO 2003/035835, WO 2000/061739. These glycoengineered antibodies have an increased ADCC. Other glycoengineering methods yielding afocusylated antibodies according to the invention are described e.g. in Niwa, R., et al., J. Immunol. Methods 306 (2005) 151-160; Shinkawa, T., et al., J Biol Chem, 278 (2003) 3466-3473; WO 03/055993 or US 2005/0249722.

One embodiment is a method of preparation of the bispecific antibody of IgG1 or IgG3 subclass which is glycosylated with a sugar chain at Asn297 whereby the amount of fucose within said sugar chain is 65% or lower, using the procedure described in WO 2005/044859, WO 2004/065540, WO 2007/031875, Umana, P., et al., Nature Biotechnol. 17 (1999) 176-180, WO 99/154342, WO 2005/018572, WO 2006/116260, WO 2006/114700, WO 2005/011735, WO 2005/027966, WO 97/028267, US 2006/0134709, US 2005/0054048, US 2005/0152894, WO 2003/035835 or WO 2000/061739.

One embodiment is a method of preparation of the bispecific antibody of IgG1 or IgG3 subclass which is glycosylated with a sugar chain at Asn297 whereby the amount of fucose within said sugar chain is 65% or lower, using the procedure described in Niwa, R., et al., J. Immunol. Methods 306 (2005) 151-160; Shinkawa, T., et al., J Biol Chem, 278 (2003) 3466-3473; WO 03/055993 or US 2005/0249722.

The antibody according to the invention is produced by recombinant means. Thus, one aspect of the current invention is a nucleic acid encoding the antibody according to the invention and a further aspect is a cell comprising said nucleic acid encoding an antibody according to the invention. Methods for recombinant production are widely known in the state of the art and comprise protein expression in prokaryotic and eukaryotic cells with subsequent isolation of the antibody and usually purification to a pharmaceutically acceptable purity. For the expression of the antibodies as aforementioned in a host cell, nucleic acids encoding the respective modified light and heavy chains are inserted into expression vectors by standard methods. Expression is performed in appropriate prokaryotic or eukaryotic host cells like CHO cells, NS0 cells, SP2/0 cells, HEK293 cells, COS cells, PER.C6 cells, yeast, or E. coli cells, and the antibody is recovered from the cells (supernatant or cells after lysis). General methods for recombinant production of antibodies are well-known in the state of the art and described, for example, in the review articles of Makrides, S. C., Protein Expr. Purif. 17 (1999) 183-202; Geisse, S., et al., Protein Expr. Purif. 8 (1996) 271-282; Kaufman, R. J., Mol. Biotechnol. 16 (2000) 151-161; Werner, R. G., Drug Res. 48 (1998) 870-880.

The bispecific antibodies according to the invention are suitably separated from the culture medium by conventional immunoglobulin purification procedures such as, for example, protein A-Sepharose, hydroxylapatite chromatography, gel electrophoresis, dialysis, or affinity chromatography. DNA and RNA encoding the monoclonal antibodies is readily isolated and sequenced using conventional procedures. The hybridoma cells can serve as a source of such DNA and RNA. Once isolated, the DNA may be inserted into expression vectors, which are then transfected into host cells such as HEK 293 cells, CHO cells, or myeloma cells that do not otherwise produce immunoglobulin protein, to obtain the synthesis of recombinant monoclonal antibodies in the host cells.

Amino acid sequence variants (or mutants) of the bispecific antibody are prepared by introducing appropriate nucleotide changes into the antibody DNA, or by nucleotide synthesis. Such modifications can be performed, however, only in a very limited range. For example, the modifications do not alter the above mentioned antibody characteristics such as the IgG isotype and antigen binding, but may improve the yield of the recombinant production, protein stability or facilitate the purification.

The term "host cell" as used in the current application denotes any kind of cellular system which can be engineered to generate the antibodies according to the current invention. In one embodiment HEK293 cells and CHO cells are used as host cells.

As used herein, the expressions "cell," "cell line," and "cell culture" are used interchangeably and all such designations include progeny. Thus, the words "transformants" and "transformed cells" include the primary subject cell and cultures derived therefrom without regard for the number of transfers. It is also understood that all progeny may not be precisely identical in DNA content, due to deliberate or inadvertent mutations. Variant progeny that have the same function or biological activity as screened for in the originally transformed cell are included. Where distinct designations are intended, it will be clear from the context.

Expression in NS0 cells is described by, e.g., Barnes, L. M., et al., Cytotechnology 32 (2000) 109-123; Barnes, L. M., et al., Biotech. Bioeng. 73 (2001) 261-270. Transient expression is described by, e.g., Durocher, Y., et al., Nucl. Acids. Res. 30 (2002) E9. Cloning of variable domains is described by Orlandi, R., et al., Proc. Natl. Acad. Sci. USA 86 (1989) 3833-3837; Carter, P., et al., Proc. Natl. Acad. Sci. USA 89 (1992) 4285-4289; and Norderhaug, L., et al., J. Immunol. Methods 204 (1997) 77-87. A preferred transient expression system (HEK 293) is described by Schlaeger, E.-J., and Christensen, K., in Cytotechnology 30 (1999) 71-83 and by Schlaeger, E.-J., in J. Immunol. Methods 194 (1996) 191-199.

The control sequences that are suitable for prokaryotes, for example, include a promoter, optionally an operator sequence, and a ribosome binding site. Eukaryotic cells are known to utilize promoters, enhancers and polyadenylation signals.

A nucleic acid is "operably linked" when it is placed in a functional relationship with another nucleic acid sequence. For example, DNA for a pre-sequence or secretory leader is operably linked to DNA for a polypeptide if it is expressed as a pre-protein that participates in the secretion of the polypeptide; a promoter or enhancer is operably linked to a coding sequence if it affects the transcription of the sequence; or a ribosome binding site is operably linked to a coding sequence if it is positioned so as to facilitate translation. Generally, "operably linked" means that the DNA sequences being linked are contiguous, and, in the case of a secretory leader, contiguous and in reading frame. However, enhancers do not have to be contiguous. Linking is accomplished by ligation at convenient restriction sites. If such sites do not exist, the synthetic oligonucleotide adaptors or linkers are used in accordance with conventional practice.

Purification of antibodies is performed in order to eliminate cellular components or other contaminants, e.g. other cellular nucleic acids or proteins, by standard techniques, including alkaline/SDS treatment, CsCl banding, column chromatography, agarose gel electrophoresis, and others well known in the art. See Ausubel, F., et al., ed. Current Protocols in Molecular Biology, Greene Publishing and Wiley Interscience, New York (1987). Different methods are well established and widespread used for protein purification, such as affinity chromatography with microbial proteins (e.g. protein A or protein G affinity chromatography), ion exchange chromatography (e.g. cation exchange (carboxymethyl resins), anion exchange (amino ethyl resins) and mixed-mode exchange), thiophilic adsorption (e.g. with beta-mercaptoethanol and other SH ligands), hydrophobic interaction or aromatic adsorption chromatography (e.g. with phenyl-sepharose, aza-arenophilic resins, or m-aminophenylboronic acid), metal chelate affinity chromatography (e.g. with Ni(II)- and Cu(II)-affinity material), size exclusion chromatography, and electrophoretical methods (such as gel electrophoresis, capillary electrophoresis) (Vijayalakshmi, M. A. Appl. Biochem. Biotech. 75 (1998) 93-102).

The term "transformation" as used herein refers to process of transfer of a vectors/nucleic acid into a host cell. If cells without formidable cell wall barriers are used as host cells, transfection is carried out e.g. by the calcium phosphate precipitation method as described by Graham, F. L., and van der Eb, A. J., Virology 52 (1973) 456ff. However, other methods for introducing DNA into cells such as by nuclear injection or by protoplast fusion may also be used. If prokaryotic cells or cells which contain substantial cell wall constructions are used, e.g. one method of transfection is calcium treatment using calcium chloride as described by Cohen, F. N, et al, PNAS. 69 (1972) 7110ff.

As used herein, "expression" refers to the process by which a nucleic acid is transcribed into mRNA and/or to the process by which the transcribed mRNA (also referred to as transcript) is subsequently being translated into peptides, polypeptides, or proteins. The transcripts and the encoded polypeptides are collectively referred to as gene product. If the polynucleotide is derived from genomic DNA, expression in a eukaryotic cell may include splicing of the mRNA.

A "vector" is a nucleic acid molecule, in particular self-replicating, which transfers an inserted nucleic acid molecule into and/or between host cells. The term includes vectors that function primarily for insertion of DNA or RNA into a cell (e.g., chromosomal integration), replication of vectors that function primarily for the replication of DNA or RNA, and expression vectors that function for transcription and/or translation of the DNA or RNA. Also included are vectors that provide more than one of the functions as described.

An "expression vector" is a polynucleotide which, when introduced into an appropriate host cell, can be transcribed and translated into a polypeptide. An "expression system" usually refers to a suitable host cell comprised of an expression vector that can function to yield a desired expression product.

It has now been found that the bispecific antibodies according to the invention have valuable characteristics such as good expression yields in mammalian cells, stability, biological or pharmacological activity, pharmacokinetic properties or toxicity. They can be used e.g. for the treatment of diseases such as cancer. The antibodies according to the invention, especially the bispecific <IGF-1R-EGFR> antibodies show highly valuable properties like growth inhibition of cancer cells expressing both receptors IGF-1R and EGFR, and antitumor efficacy causing a benefit for a patient suffering from cancer. The bispecific <IGF-1R-EGFR> antibodies according to the invention show reduced internalization of both receptors IGF-1R and EGFR when compared to their parent monospecific <IGF-1R> and <EGFR> antibodies on cancer cells expressing both receptors IGF-1R and EGFR.

One aspect of the invention is a pharmaceutical composition comprising an antibody according to the invention. Another aspect of the invention is the use of an antibody according to the invention for the manufacture of a pharmaceutical composition. A further aspect of the invention is a method for the manufacture of a pharmaceutical composition comprising an antibody according to the invention. In another aspect, the present invention provides a composition, e.g. a pharmaceutical composition, containing an antibody according to the present invention, formulated together with a pharmaceutical carrier.

One embodiment of the invention is the bispecific antibody according to the invention for the treatment of cancer.

Another aspect of the invention is said pharmaceutical composition for the treatment of cancer.

Another aspect of the invention is the use of an antibody according to the invention for the manufacture of a medicament for the treatment of cancer.

Another aspect of the invention is method of treatment of patient suffering from cancer by administering an antibody according to the invention to a patient in the need of such treatment.

As used herein, "pharmaceutical carrier" includes any and all solvents, dispersion media, coatings, antibacterial and antifungal agents, isotonic and absorption delaying agents, and the like that are physiologically compatible. Preferably, the carrier is suitable for intravenous, intramuscular, subcutaneous, parenteral, spinal or epidermal administration (e.g. by injection or infusion).

A composition of the present invention can be administered by a variety of methods known in the art. As will be appreciated by the skilled artisan, the route and/or mode of administration will vary depending upon the desired results. To administer a compound of the invention by certain routes of administration, it may be necessary to coat the compound with, or co-administer the compound with, a material to prevent its inactivation. For example, the compound may be administered to a subject in an appropriate carrier, for example, liposomes, or a diluent. Pharmaceutically acceptable diluents include saline and aqueous buffer solutions. Pharmaceutical carriers include sterile aqueous solutions or dispersions and sterile powders for the extemporaneous preparation of sterile injectable solutions or dispersion. The use of such media and agents for pharmaceutically active substances is known in the art.

The phrases "parenteral administration" and "administered parenterally" as used herein means modes of administration other than enteral and topical administration, usually by injection, and includes, without limitation, intravenous, intramuscular, intra-arterial, intrathecal, intracapsular, intraorbital, intracardiac, intradermal, intraperitoneal, transtracheal, subcutaneous, subcuticular, intra-articular, subcapsular, subarachnoid, intraspinal, epidural and intrasternal injection and infusion.

The term cancer as used herein refers to proliferative diseases, such as lymphomas, lymphocytic leukemias, lung cancer, non small cell lung (NSCL) cancer, bronchioloalviolar cell lung cancer, bone cancer, pancreatic cancer, skin cancer, cancer of the head or neck, cutaneous or intraocular melanoma, uterine cancer, ovarian cancer, rectal cancer, cancer of the anal region, stomach cancer, gastric cancer, colon cancer, breast cancer, uterine cancer, carcinoma of the fallopian tubes, carcinoma of the endometrium, carcinoma of the cervix, carcinoma of the vagina, carcinoma of the vulva, Hodgkin's Disease, cancer of the esophagus, cancer of the small intestine, cancer of the endocrine system, cancer of the thyroid gland, cancer of the parathyroid gland, cancer of the adrenal gland, sarcoma of soft tissue, cancer of the urethra, cancer of the penis, prostate cancer, cancer of the bladder, cancer of the kidney or ureter, renal cell carcinoma, carcinoma of the renal pelvis, mesothelioma, hepatocellular cancer, biliary cancer, neoplasms of the central nervous system (CNS), spinal axis tumors, brain stem glioma, glioblastoma multiforme, astrocytomas, schwanomas, ependymonas, medulloblastomas, meningiomas, squamous cell carcinomas, pituitary adenoma and Ewings sarcoma, including refractory versions of any of the above cancers, or a combination of one or more of the above cancers.

These compositions may also contain adjuvants such as preservatives, wetting agents, emulsifying agents and dispersing agents. Prevention of presence of microorganisms may be ensured both by sterilization procedures, supra, and by the inclusion of various antibacterial and antifungal agents, for example, paraben, chlorobutanol, phenol, sorbic acid, and the like. It may also be desirable to include isotonic agents, such as sugars, sodium chloride, and the like into the compositions. In addition, prolonged absorption of the injectable pharmaceutical form may be brought about by the inclusion of agents which delay absorption such as aluminum monostearate and gelatin.

Regardless of the route of administration selected, the compounds of the present invention, which may be used in a suitable hydrated form, and/or the pharmaceutical compositions of the present invention, are formulated into pharmaceutically acceptable dosage forms by conventional methods known to those of skill in the art.

Actual dosage levels of the active ingredients in the pharmaceutical compositions of the present invention may be varied so as to obtain an amount of the active ingredient which is effective to achieve the desired therapeutic response for a particular patient, composition, and mode of administration, without being toxic to the patient. The selected dosage level will depend upon a variety of pharmacokinetic factors including the activity of the particular compositions of the present invention employed, the route of administration, the time of administration, the rate of excretion of the particular compound being employed, the duration of the treatment, other drugs, compounds and/or materials used in combination with the particular compositions employed, the age, sex, weight, condition, general health and prior medical history of the patient being treated, and like factors well known in the medical arts.

The composition must be sterile and fluid to the extent that the composition is deliverable by syringe. In addition to water, the carrier preferably is an isotonic buffered saline solution.

Proper fluidity can be maintained, for example, by use of coating such as lecithin, by maintenance of required particle size in the case of dispersion and by use of surfactants. In many cases, it is preferable to include isotonic agents, for example, sugars, polyalcohols such as mannitol or sorbitol, and sodium chloride in the composition.

Description of the Amino Acid Sequences

SEQ ID NO: 1 <IGF-1R> heavy chain, OA-Ak18-scFab-GA201 (+WT)

SEQ ID NO: 2 <IGF-1R> light chain, OA-Ak18-scFab-GA201 (+WT)

SEQ ID NO: 3 <EGFR> peptide connected heavy and light chain with disulfide stabilization VH 44/VL100 of OA-Ak18-scFab-GA201

SEQ ID NO: 4 <EGFR> peptide connected heavy and light chain of OA-Ak18-scFab-GA201_WT SEQ ID NO: 5 <EGFR> heavy chain, OA-GA201-scFab-Ak18 (+WT)

SEQ ID NO: 6 <EGFR> light chain, OA-GA201-scFab-Ak18 (+WT)
SEQ ID NO: 7 <IGF-1R> peptide connected heavy and light chain with disulfide stabilization VH 44/VL 100-OA-GA201-scFab-Ak18
SEQ ID NO: 8 <IGF-1R> peptide connected heavy and light chain of OA-GA201-scFab-Ak18_WT
SEQ ID NO: 9 <VEGF> heavy chain, Ang2-VEGF OA-Ava-N-scFabLC06 (+SS)
SEQ ID NO: 10 <VEGF> light chain, Ang2-VEGF OA-Ava-N-scFabLC06 (+SS)
SEQ ID NO: 11 <ANG-2> peptide connected heavy and light chain with disulfide stabilization VH 44/VL100 of Ang2-VEGF OA-Ava-N-scFabLC06SS
SEQ ID NO: 12 <ANG-2> peptide connected heavy and light chain of Ang2-VEGF OA-Ava-N-scFabLC06
SEQ ID NO: 13 Human EGFR
SEQ ID NO: 14 Human IGF-1R
SEQ ID NO: 15 Human VEGF
SEQ ID NO: 16 Human ANG-2

The following examples, sequence listing and figures are provided to aid the understanding of the present invention, the true scope of which is set forth in the appended claims. It is understood that modifications can be made in the procedures set forth without departing from the spirit of the invention.

Experimental Procedure

EXAMPLES

Materials & Methods
Recombinant DNA Techniques

Standard methods were used to manipulate DNA as described in Sambrook, J. et al., Molecular cloning: A laboratory manual; Cold Spring Harbor Laboratory Press, Cold Spring Harbor, N.Y., 1989. The molecular biological reagents were used according to the manufacturer's instructions.

DNA and Protein Sequence Analysis and Sequence Data Management

General information regarding the nucleotide sequences of human immunoglobulins light and heavy chains is given in: Kabat, E. A., et al., (1991) Sequences of Proteins of Immunological Interest, Fifth Ed., NIH Publication No 91-3242. Amino acids of antibody chains are numbered according to EU numbering (Edelman, G. M., et al., PNAS 63 (1969) 78-85; Kabat, E. A., et al., (1991) Sequences of Proteins of Immunological Interest, Fifth Ed., NIH Publication No 91-3242). The GCG's (Genetics Computer Group, Madison, Wis.) software package version 10.2 and Infomax's Vector NTI Advance suite version 8.0 was used for sequence creation, mapping, analysis, annotation and illustration.

DNA Sequencing

DNA sequences were determined by double strand sequencing performed at SequiServe (Vaterstetten, Germany) and Geneart AG (Regensburg, Germany).

Gene Synthesis

Desired gene segments were prepared by Geneart AG (Regensburg, Germany) from synthetic oligonucleotides and PCR products by automated gene synthesis. The gene segments encoding "knobs-into-hole" antibody heavy chains carrying S354C and T366W mutations and "knobs-into-hole" heavy chains carrying Y349C, T366S, L368A and Y407V mutations in the CH3 domain in combination with umodified VH domains or scFab antibody fragments as well as antibody light chains are flanked by singular restriction endonuclease cleavage sites (BamHI-XbaI or BamHI-KpnI) and were cloned into pGA18 (ampR) plasmids. The plasmid DNA was purified from transformed bacteria and concentration determined by UV spectroscopy. The DNA sequence of the subcloned gene fragments was confirmed by DNA sequencing. All constructs were designed with a 5'-end DNA sequence coding for a leader peptide (MGWSCIILFL-VATATGVHS), which targets proteins for secretion in eukaryotic cells.

Construction of the Expression Plasmids

A Roche expression vector was used for the construction of all "knobs-into-hole" heavy chain as well as antibody light chain encoding expression plasmids. The vector is composed of the following elements:

a hygromycin resistance gene as a selection marker,
an origin of replication, oriP, of Epstein-Barr virus (EBV),
an origin of replication from the vector pUC18 which allows replication of this plasmid in *E. coli*
a beta-lactamase gene which confers ampicillin resistance in *E. coli*,
the immediate early enhancer and promoter from the human cytomegalovirus (HCMV),
the human 1-immunoglobulin polyadenylation ("poly A") signal sequence, and
unique BamHI and XbaI restriction sites.

The immunoglobulin genes comprising the "knobs-into-hole" heavy chains with unmodified VH domains or scFab fragments as well as unmodified light chains were prepared by gene synthesis and cloned into pGA18 (ampR) plasmids as described. The pG18 (ampR) plasmids carrying the synthesized DNA segments and the Roche expression vector were digested with BamHI and XbaI or BamHI and KpnI restriction enzymes (Roche Molecular Biochemicals) and subjected to agarose gel electrophoresis. Purified "knobs-into-hole" heavy and unmodified light chain encoding DNA segments were then ligated to the isolated Roche expression vector BamHI/XbaI or BamHI/KpnI fragment resulting in the final expression vectors. The final expression vectors were transformed into *E. coli* cells, expression plasmid DNA was isolated (Miniprep) and subjected to restriction enzyme analysis and DNA sequencing. Correct clones were grown in 150 ml LB-Amp medium, again plasmid DNA was isolated (Maxiprep) and sequence integrity confirmed by DNA sequencing.

Transient Expression of Bispecific Antibodies in HEK293 Cells

Recombinant bispecific antibodies were expressed by transient transfection of human embryonic kidney 293-F cells using the FreeStyle™ 293 Expression System according to the manufacturer's instruction (Invitrogen, USA). Briefly, suspension FreeStyle™ 293-F cells were cultivated in FreeStyle™ 293 Expression medium at 37° C./8% $CO_2$ and the cells were seeded in fresh medium at a density of $1$-$2 \times 10^6$ viable cells/ml on the day of transfection. "Knobs-into-hole" DNA-293fectin complexes were prepared in Opti-MEM® I medium (Invitrogen, USA) using 325 µl of 293Fectin™ (Invitrogen, Germany) and 250 µg of "Knobs-into-hole" heavy chain 1 and 2 and light chain plasmid DNA in a 1:1:1 or 1:2:1 molar ratio for a 250 ml final transfection volume. Antibody containing cell culture supernatants were harvested 7 days after transfection by centrifugation at 14000 g for 30 minutes and filtered through a sterile filter (0.22 µm). Supernatants were stored at −20° C. until purification.

Purification of Bispecific Antibodies

Bispecific antibodies were purified from cell culture supernatants by affinity chromatography using Protein A-Sepharose™ (GE Healthcare, Sweden) and Superdex200 size exclusion chromatography. Briefly, sterile filtered cell culture supernatants were applied on a HiTrap ProteinA HP (5 ml) column equilibrated with PBS buffer (10 mM $Na_2HPO_4$, 1 mM $KH_2PO_4$, 137 mM NaCl and 2.7 mM KCl, pH 7.4). Unbound proteins were washed out with equilibration buffer. Antibody and antibody variants were eluted with 0.1 M citrate buffer, pH 2.8, and the protein containing fractions were neutralized with 0.1 ml 1 M Tris, pH 8.5. Then, the eluted protein fractions were pooled, concentrated with an Amicon Ultra centrifugal filter device (MWCO: 30 K, Millipore) to a volume of 3 ml and loaded on a Superdex200 HiLoad 120 ml 16/60 gel filtration column (GE Healthcare, Sweden) equilibrated with 20 mM Histidin, 140 mM NaCl, pH 6.0. Fractions containing purified bispecific antibodies with less than 5% high molecular weight aggregates were pooled and stored as 1.0 mg/ml aliquots at −80° C.

Analysis of Purified Proteins

The protein concentration of purified protein samples was determined by measuring the optical density (OD) at 280 nm, using the molar extinction coefficient calculated on the basis of the amino acid sequence. Purity and molecular weight of bispecific and control antibodies were analyzed by SDS-PAGE in the presence and absence of a reducing agent (5 mM 1,4-dithiotreitol) and staining with Coomassie brilliant blue. The NuPAGE® Pre-Cast gel system (Invitrogen, USA) was used according to the manufacturer's instruction (4-20% Tris-Glycine gels). The aggregate content of bispecific and control antibody samples was analyzed by high-performance SEC using a Superdex 200 analytical size-exclusion column (GE Healthcare, Sweden) in 200 mM $KH_2PO_4$, 250 mM KCl, pH 7.0 running buffer at 25° C. 25 µg protein were injected on the column at a flow rate of 0.5 ml/min and eluted isocratic over 50 minutes. For stability analysis, concentrations of 1 mg/ml of purified proteins were incubated at 4° C. and 40° C. for 7 days and then evaluated by high-performance SEC The integrity of the amino acid backbone of reduced bispecific antibody light and heavy chains was verified by NanoElectrospray Q-TOF mass spectrometry after removal of N-glycans by enzymatic treatment with Peptide-N-Glycosidase F (Roche Molecular Biochemicals).

Surface Plasmon Resonance

The binding affinity is determined with a standard binding assay at 25° C., such as surface plasmon resonance technique (BIAcore®, GE-Healthcare Uppsala, Sweden). For affinity measurements, 30 mg/ml of anti Fcγ antibodies (from goat, Jackson Immuno Research) were coupled to the surface of a CM-5 sensor chip by standard amine-coupling and blocking chemistry on a SPR instrument (BIACORE™ T100). After conjugation, mono- or bispecific Her3/cMet antibodies were injected at 25° C. at a flow rate of 5 µL/min, followed by a dilution series (0 nM to 1000 nM) of human HER3 or c-Met ECD at 30 µL/min. As running buffer for the binding experiment PBS/0.1% BSA was used. The chip was then regenerated with a 60 s pulse of 10 mM glycine-HCl, pH 2.0 solution.

EGFR/IGF-1R Surface Plasmon Resonance

SPR experiments were performed using a BIACORE™ T100 instrument (GE Healthcare Biosciences AB, Uppsala, Sweden). IGF-1R or EGFR were immobilized on the surface of a CM5 biosensorchip using standard amine-coupling chemistry. IGF-1R or EGFR were injected in sodium acetate, pH 5.0 at 1 µg/ml using the immobilization wizard procedure with an aim for 200 RU (IGF-1R) or 100 RU (EGFR). Reference control flow cells were treated in the same way but with vehicle buffer only. The antibodies were diluted in 1×PBS pH 7.4, 0.05% Tween®20. (Roche Diagnostics GmbH) and injected at increasing concentrations between 3.125 and 50 nM with a flow rate of 30 µL/min. The contact time (association phase) was 3 min (EGFR binding) and 5 min (IGF-1R binding), the dissociation time was 10 min (EGFR) and 3 min (IGF-1R). EGFR binding was regenerated with an inject of 0.85% phosphoric acid for 30 s at a flow rate of 5 µl/min. IGF-1R binding was regenerated with an inject of 4 M magnesium chloride for 1 min at 5 µl/min. Kinetic rate constants and equilibrium dissociation constants were calculated by using the 1:1 Langmuir binding model within the Biaevaluation software To demonstrate simultaneous binding, the bispecific antibodies are injected onto the EGFR surface at 25 nM for 1 min, 5 µl/min flow rate. After capturing the antibody to the EGFR surface, IGF-1R is injected at increasing concentrations between 2.5 and 80 nM with a flow rate of 30 µl/min. The surface is regenerated with an inject of 0.85% phosphoric acid for 30 s at a flow rate of 5 µl/min. Kinetic rate constants and equilibrium dissociation constants are calculated by using the 1:1 Langmuir binding model within the Biaevaluation software.

ANG-2 Binding Surface Plasmon Resonance (Biacore)

Figure 6:
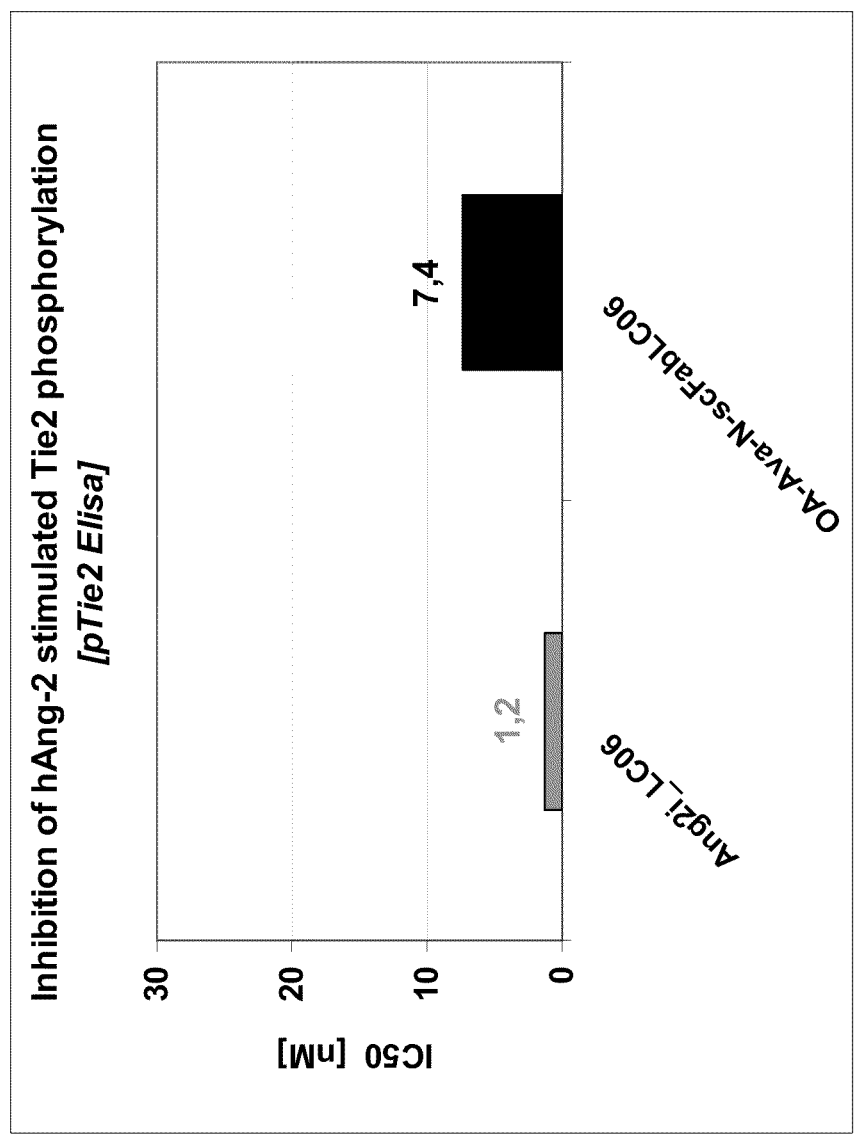
FIG. 6 Inhibition of the Tie2 phosphorylation by bispecific antibody according to the invention Ang2-VEGF OA-Ava-N-scFabLC06.
Figure 7A:
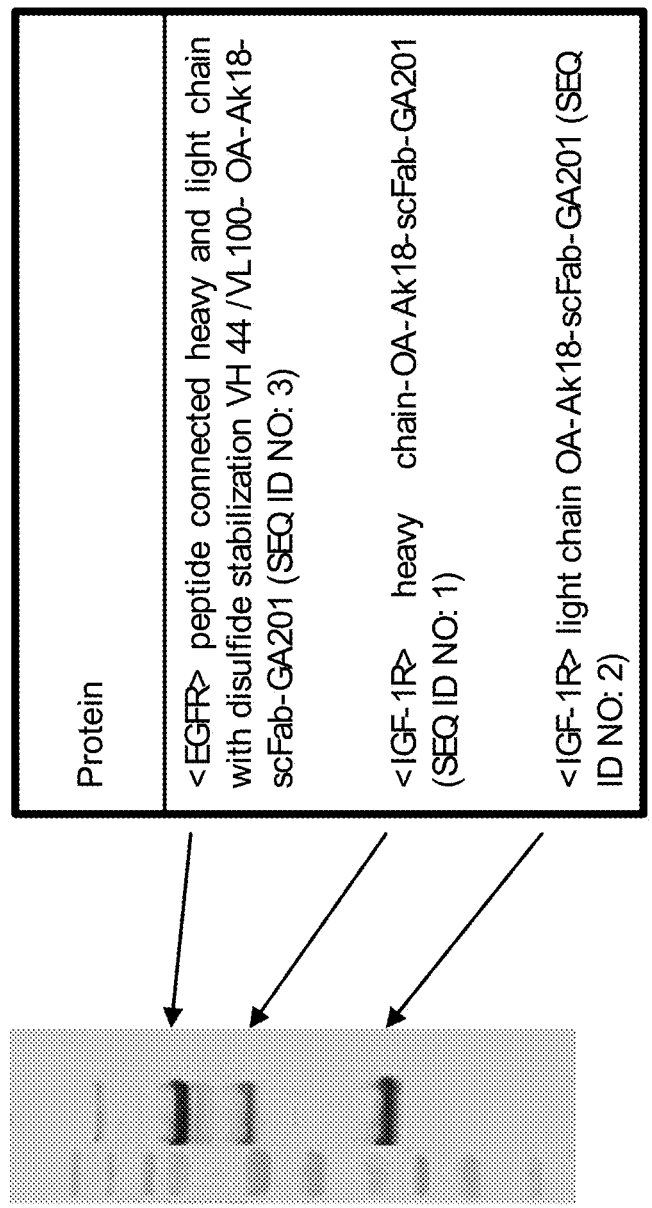
FIG. 7 Western blot (reduced) of OA-Ak18-scFab-GA201 (FIG. 7a) and OA-GA201-scFab-Ak18 (FIG. 7b).
Figure 7B:
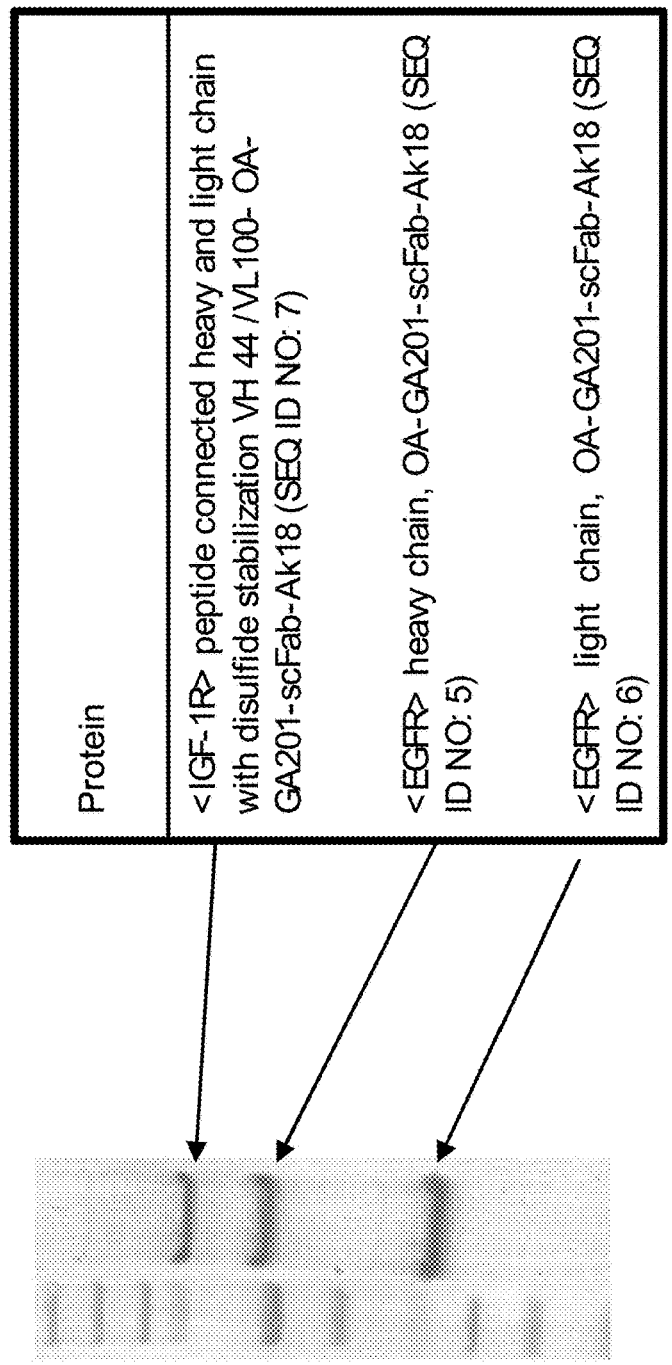

Binding of the antibodies to the antigen e.g. human ANG-2 is investigated by surface plasmon resonance using a BIACORE™ T100 instrument (GE Healthcare Biosciences AB, Uppsala, Sweden). Briefly, for affinity measurements goat<hIgG-Fcgamma> polyclonal antibodies were immobilized on a CM5 chip via amine coupling for presentation of the antibodies against human ANG-2 (FIG. 6B). Binding was measured in HBS buffer (HBS-P (10 mM HEPES, 150 mM NaCl, 0.005% Tween20 Tween®20, ph 7.4), 25° C. Purified ANG-2-His (R&D systems or in house purified) was added in various concentrations between 6.25 nM and 200 nM in solution. Association was measured by an ANG-2-injection of 3 minutes; dissociation was measured by washing the chip surface with HBS buffer for 3 minutes and a KD value was estimated using a 1:1 Langmuir binding model. Due to heterogenity of the ANG-2 preparation no 1:1 binding could be observed; KD values are thus only relative estimations. Negative control data (e.g. buffer curves) were subtracted from sample curves for correction of system intrinsic baseline drift and for noise signal reduction. BIACORE™ T100 Evaluation Software version 1.1.1 was used for analysis of sensorgrams and for calculation of affinity data. Alternatively, Ang-2 could be captured with a capture level of 2000-1700 RU via a PentaHisAntibody (PentaHis-Ab BSA-free, Qiagen No. 34660) that was immobilized on a CM5 chip via amine coupling (BSA-free) (see below).

VEGF Binding Surface Plasmon Resonance (Biacore)

VEGF binding of bispecific <VEGF-Ang-2> antibodies is analyzed using surface plasmon resonance technology on a BIACORE™ T100 instrument according to the following protocol and analyzed using the T100 software package: Briefly <VEGF> antibodies were captured on a CM5-Chip via binding to a Goat Anti Human IgG (JIR 109-005-098). The capture antibody was immobilized by amino coupling using standard amino coupling as follows: HBS-N buffer served as running buffer, activation was done by mixture of EDC/NHS with the aim for a ligand density of 700 RU. The Capture-Antibody was diluted in coupling buffer NaAc, pH 5.0, c=2 µg/mL, finally still activated carboxyl groups were blocked by injection of 1 M Ethanolamine. Capturing of Mabs <VEGF> antibodies was done at a flow of 5 µL/min and c(Mabs<VEGF>)=10 nM, diluted with running buffer+

1 mg/mL BSA; a capture level of approx. 30 RU should be reached. rhVEGF (rhVEGF, R&D-Systems Cat.-No, 293-VE) was used as analyte. The kinetic characterization of VEGF binding to <VEGF> antibodies was performed at 37° C. in PBS+0.005% (v/v) Tween®20, as running buffer. The sample was injected with a flow of 50 µL/min and an association of time 80 sec. and a dissociation time of 1200 sec with a concentration series of rhVEGF from 300-0.29 nM. Regeneration of free capture antibody surface was performed with 10 mM Glycin pH 1.5 and a contact time of 60 sec after each analyte cycle. Kinetic constants were calculated by using the usual double referencing method (control reference: binding of rhVEGF to capture molecule Goat Anti Human IgG, blanks on the measuring flow cell, rhVEGF concentration "0", Model: Langmuir binding 1:1, (Rmax set to local because of capture molecule binding).

Generation of HEK293-Tie2 Cell Line

In order to determine the interference of Angiopoietin-2 antibodies with ANG2 stimulated Tie2 phosphorylation and binding of ANG2 to Tie2 on cells a recombinant HEK293-Tie cell line was generated. Briefly, a pcDNA3 based plasmid (RB22-pcDNA3 Topo hTie2) coding for full-length human Tie2 (SEQ ID 108) under control of a CMV promoter and a Neomycin resistance marker was transfected using Fugene (Roche Applied Science) as transfection reagent into HEK293 cells (ATCC) and resistant cells were selected in DMEM 10% FCS, 500 µg/ml G418. Individual clones were isolated via a cloning cylinder, and subsequently analyzed for Tie2 expression by FACS. Clone 22 was identified as clone with high and stable Tie2 expression even in the absence of G418 (HEK293-Tie2 clone22). HEK293-Tie2 clone22 was subsequently used for cellular assays: ANG2 induced Tie2 phosphorylation and ANG2 cellular ligand binding assay.

VEGF Induced HUVEC Proliferation Assay

VEGF induced HUVEC (Human Umbilical Vein Endothelial Cells, Promocell #C-12200) proliferation was chosen to measure the cellular function of VEGF antibodies. Briefly, 5000 HUVEC cells (low passage number, ≤5 passages) per 96 well were incubated in 100 µl starvation medium (EBM-2 Endothelial basal medium 2, Promocell #C-22211, 0.5% FCS, Penicilline/Streptomycine) in a collagen I-coated BD Biocoat Collagen I 96-well microtiter plate (BD #354407/35640 over night. Varying concentrations of antibody were mixed with rhVEGF (30 ng 1/ml final concentration, BD #354107) and pre-incubated for 15 minutes at room temperature. Subsequently, the mix was added to the HUVEC cells and they were incubated for 72 h at 37° C., 5% CO2. On the day of analysis the plate was equilibrated to room temperature for 30 min and cell viability/proliferation was determined using the CellTiter-Glo™ Luminescent Cell Viability Assay kit according to the manual (Promega, #G7571/2/3). Luminescence was determined in a spectrophotometer.

ANG2 Induced Tie2 Phosphorylation Assay

Inhibition of ANG2 induced Tie2 phosphorylation by the bispecific <ANG2-VEGF> antibodies was measured according to the following assay principle. HEK293-Tie2 clone22 was stimulated with ANG2 for 5 minutes in the absence or presence of <ANG2-VEGF> antibodies and P-Tie2 was quantified by a sandwich ELISA. Briefly, 2×105 HEK293-Tie2 clone 22 cells per well were grown over night on a Poly-D-Lysine coated 96 well-microtiter plate in 100 µl DMEM, 10% FCS, 500 µg/ml Geneticin. The next day a titration row of <ANG2-VEGF> antibodies was prepared in a microtiter plate (4-fold concentrated, 75 µl final volume/well, duplicates) and mixed with 75 µl of an ANGPT2 (R&D systems #623-AN] dilution (3.2 µg/ml as 4-fold concentrated solution). Antibodies and ANG2 were pre-incubated for 15 min at room temperature. 100 µl of the mix were added to the HEK293-Tie2 clone 22 cells (pre-incubated for 5 min with 1 mM NaV3O4, Sigma #S6508) and incubated for 5 min at 37° C. Subsequently, cells were washed with 200 µl ice-cold PBS+1 mM NaV3O4 per well and lysed by addition of 120 µl lysis buffer (20 mM Tris, pH 8.0, 137 mM NaCl, 1% NP-40, 10% glycerol, 2 mM EDTA, 1 mM NaV3O4, 1 mM PMSF and 10 µg/ml Aprotinin) per well on ice. Cells were lysed for 30 min at 4° C. on a microtiter plate shaker and 100 µl lysate were transferred directly into a p-Tie2 ELISA microtiter plate (R&D Systems, R&D #DY990) without previous centrifugation and without total protein determination. P-Tie2 amounts were quantified according to the manufacturer's instructions and IC50 values for inhibition were determined using XLfit4 analysis plug-in for Excel (Dose-response one site, model 205).

Cell Titer Glow Assay

Cell viability and proliferation was quantified using the cell titer glow assay (Promega). The assay was performed according to the manufacturer's instructions. Briefly, cells were cultured in 96-well plates in a total volume of 100 µL for the desired period of time. For the proliferation assay, cells were removed from the incubator and placed at room temperature for 30 min. 100 µL of cell titer glow reagent were added and multi-well plates were placed on an orbital shaker for 2 min. Luminescence was quantified after 15 min on a microplate reader (Tecan).

Example 1a

Expression & Purification Bispecific, Bivalent <VEGF-ANG-2> Antibody Molecules

According the procedures described in the materials and methods above, the bispecific, bivalent <VEGF-ANG-2> antibody molecules Ang2-VEGF OA-Ava-N-scFabLC06SS and Ang2-VEGF OA-Ava-N-scFabLC06, were expressed and purified. The VH and VL of <VEGF> part are based on bevacizumab. The VH and VL of <ANG2> part are based on VH and VL sequences of ANG2i-LC06 (which is decribed in the PCT application No. PCT/EP2009/007182 and which was obtained via phage display). The relevant light and heavy chain amino acid sequences of these bispecific, bivalent antibodies are given in SEQ ID NO: 9, SEQ ID NO: 10, SEQ ID NO: 11 (for Ang2-VEGF OA-Ava-N-scFabLC06SS), and in SEQ ID NO: 9, SEQ ID NO: 10, SEQ ID NO: 12 (for Ang2-VEGF OA-Ava-N-scFabLC06). Expression of Ang2-VEGF OA-Ava-N-scFabLC06SS and Ang2-VEGF OA-Ava-N-scFabLC06 was confirmed by Western blot. Purification of Ang2-VEGF OA-Ava-N-scFabLC06SS and Ang2-VEGF OA-Ava-N-scFabLC06 led to the following yields.

| | | Protein A | | SEC | |
|---|---|---|---|---|---|
| Clone | Supernatant | Yield | Mono. | Yield | Mono. |
| OA-Ava-N-scFabLC06 | 0.5 L | 42.5 mg | 77% | 27.0 mg | 94.8% |
| OA-Ava-N-scFabLC06SS | 1.5 L | 160 mg | 85% | 93 mg | >99% |

* MassSpec: no homomeric heavy chain dimers were detected

Binding and other properties were determined as described.

Example 1b

Expression & Purification Bispecific, Bivalent <IGF-1R-EGFR> Antibody Molecules

TABLE

Overview of bispecific, bivalent <IGF-1R-EGFR> antibody molecules

| Construct | Sequence | scFab VH44-VL100 Disulfide |
|---|---|---|
| OA-Ak18-scFab-GA201 WT | SEQ ID NO: 4 (Heavy chain 1) SEQ ID NO: 1 (Heavy chain 2) SEQ ID NO: 2 (Light chain) | − |
| OA-Ak18-scFab-GA201 | SEQ ID NO: 3 (Heavy chain 1) SEQ ID NO: 1 (Heavy chain 2) SEQ ID NO: 2 (Light chain) | + |
| OA-GA201-scFab-Ak18 WT | SEQ ID NO: 8 (Heavy chain 1) SEQ ID NO: 5 (Heavy chain 2) SEQ ID NO: 6 (Light chain) | − |
| OA-GA201-scFab-Ak18 | SEQ ID NO: 7 (Heavy chain 1) SEQ ID NO: 5 (Heavy chain 2) SEQ ID NO: 6 (Light chain) | + |

According the procedures described in the materials and methods above, the bispecific, bivalent <IGF-1R-EGFR> antibody molecules OA-Ak18-scFab-GA201 and OA-GA201-scFab-Ak18, were expressed with a 1:1:1 plasmid ratio and purified. The bispecific antibody is based on the antigen-binding sites of <IGF-1R> HUMAB Clone 18 (DSM ACC 2587; WO 2005/005635, abbreviated as <IGF-1R>Clone18 or <IGF-1R>AK18) and humanized <EGFR>ICR62 (WO 2006/082515 abbreviated as <EGFR>ICR62). The relevant light and heavy chain amino acid sequences of these bispecific, bivalent antibodies are given in SEQ ID NO: 1, SEQ ID NO: 2, SEQ ID NO: 3 (for OA-Ak18-scFab-GA201), and in SEQ ID NO: 5, SEQ ID NO: 6, SEQ ID NO: 7 (for OA-GA201-scFab-Ak18). Expression of OA-Ak18-scFab-GA201 and OA-GA201-scFab-Ak18 was confirmed by Western blot. After Protein A purification of cell culture supernatants both constructs showed between 50 and 58% of bispecific antibody with the expected molecular weight of approximately 148 kDa as detected by analytical SEC and a high amount of half antibody with a molecular weight of 100 kDa. After SEC purification both constructs showed between 86 and 90% homogenous monomer with a molecular weight of 148 kDa and a residual side product of 100 kDa. The OA-GA201-scFab-Ak18 was also expressed with a 1:2:1 plasmid ratio and subjected to Prot A and SEC purification. In comparison to the 1:1:1 expression ratio, the amount of half antibody after Prot A was reduced from 30% to 6% with a 1:2:1 expression level as detected by a Bioanalyzer (Caliper analysis). Mass Spec analysis of the SEC purified proteins confirmed the efficient removal of the half heavy chain 1 humanized <EGFR>ICR62 antibody by change of the plasmid ratio upon transfection. The OA-GA201-scFab-Ak18 purification yield was increased by 40% with a 1:2:1 plasmid ratio upon expression in HEK293 cells.

The bispecific, bivalent <IGF-1R-EGFR> antibody molecule OA-GA201-scFab-Ak18_WT, (with the relevant light and heavy chain amino acid sequences given in SEQ ID NO: 5, SEQ ID NO: 6, SEQ ID NO: 8) was expressed with a 1:1:1 and 1:2:1 plasmid ratio and purified analogously.

Results for the 1:2:1 plasmid ratio:

| Purification | Protein A | | SEC | |
|---|---|---|---|---|
| Construct | Yield | Monomer | Yield | Monomer |
| OA-GA201-scFab-Ak18_WT (9.9 L) | 283.5 mg | 85.0% (Analyt. SEC) 86.0% (BioAnalyzer) | 204.1 mg | 98.0% (Analyt. SEC) 95.0% (BioAnalyzer) |

The OA-scFab constructs with only 3 plasmids has the advantage of a valuable side product profile over similar heterodimeric approaches using the knobs-into-hole technology to generate bispecific molecules with 4 expression plasmids (see e.g. WO 2009/080253. The antibodies accorsign to the invention show a complete absence of wrongly paired light chains or antibodies lacking the light chain (data not shown).

The described 1:2:1 method was shown to yield bispecific molecules with high purity and a clear reduction of half antibodies and a complete absence of wrongly paired light chains or antibodies lacking the light chain (data not shown).

Binding and other properties were determined as described.

The bispecific, bivalent <IGF-1R-EGFR> antibody molecule OA-Ak18-scFab-GA201_WT, (with the relevant light and heavy chain amino acid sequences given in in SEQ ID NO: 1, SEQ ID NO: 2, SEQ ID NO: 4 (for OA-Ak18-scFab-GA201_WT), can be expressed and purified analogously.

Example 2

(Simultaneous) Binding of Bispecific Antibodies to Both Antigens

The binding of the different bispecific antibody formats were compared to the binding of the 'wildtype' IgGs from which the binding modules and bispecific antibodies were derived. These analyses were carried out by applying Surface Plasmon Resonance (BIACORE™) as described above. Simultaneous binding of bispecific antibody OA-GA201-scFab-A1(18_WT to IGF-1R and EGFR could be detected.
Instrument: BIACORE™ T100 (GE Healthcare), T200 sensitivity enhanced
Software: T200 Control, Version 1.0
Software: T200 Evaluation, Version 1.0
Chip: CM5-Chip
Assay Standard amine coupling on flow cells 1 to 4 according to the manufacturer's instructions: running buffer: HBS-N buffer, activation by mixture of EDC/NHS, aim for ligand density. EGFR was diluted in coupling buffer NaAc, pH 4.5, c=15 µg/mL; finally remaining activated carboxyl groups were blocked by injection of 1 M Ethanolamine.

Amine coupled EGFR on flow cell 1 was used as reference control surface for correction of possible buffer-effects or non specific binding.

The simultaneuos binding was measured at a flow rate of 30 µL/min at 25° C. Bispecific Ab was injected for 2 minutes at a concentration of c=10 nM followed immediately by a consecutive injection of either human or cyno IGF (association time: 2 minute, dissociation time: 3 minutes, c=150 nM).

All samples were diluted with running buffer+1 mg/mL BSA.

After each cycle the regeneration was performed using 15 mM NaOH, contact time 1 minute, flow rate 30 μL/min. Negative control: Instead of IGF1R dilution buffer was injected as negative control.

Results

Figure 9:
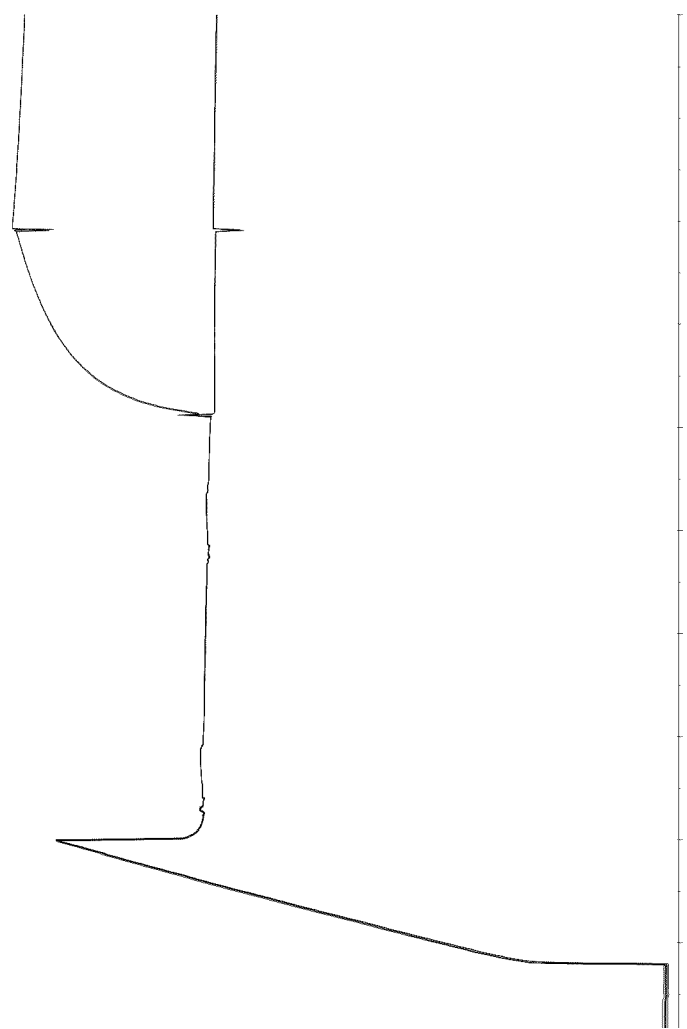
FIG. 9 BIACORE™ (Surface plasmon resonance)-Sensogram: Bispecific antibody OA-GA201-scFab-Ak18 WT showed simultaneous binding of amine coupled human EGFR and human IGF1R (x-axis: response, y-axis: time).

Bispecific Abs: OA-GA201-scFab-Ak18_WT showed simultaneous binding of amine coupled human EGFR and human IGF1R (see sensogram FIG. 9).

Example 3a

ANG2-VEGF-Mab Tie2 Phoshorylation Inhibition

Figure 5:
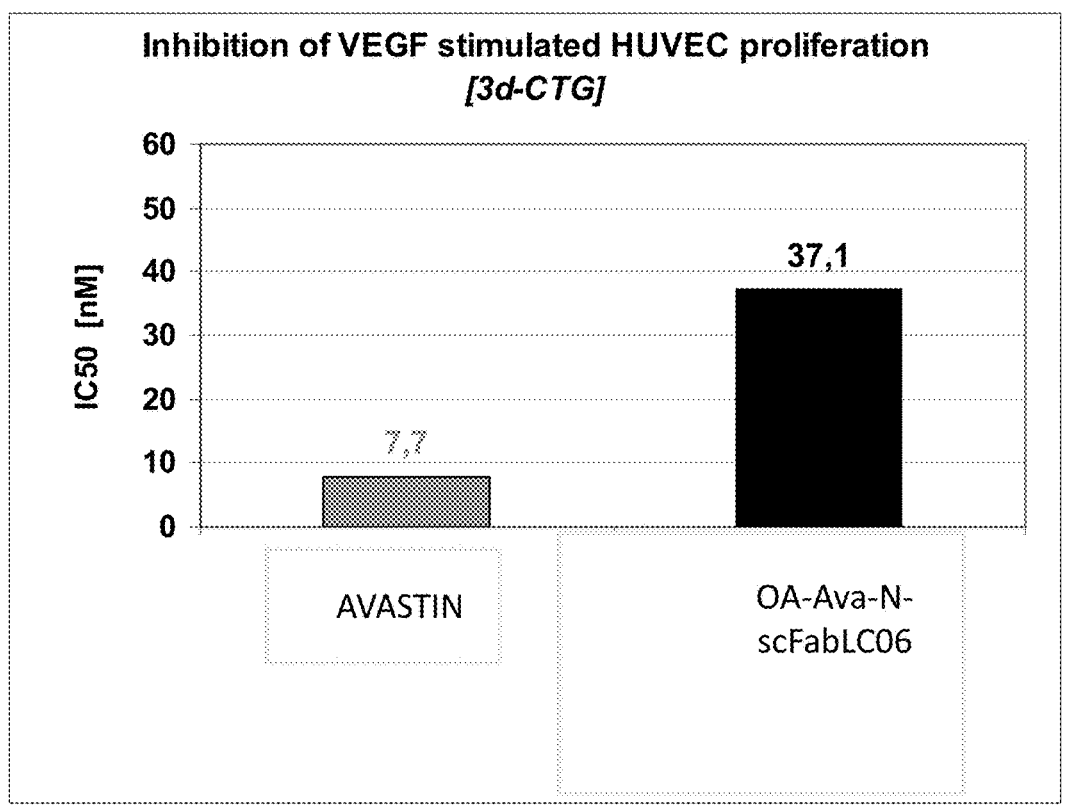
FIG. 5 Inhibition of the HUVEC proliferation by bispecific antibody according to the invention Ang2-VEGF OA-Ava-N-scFabLC06.

Inhibition of VEGF induced HUVEC proliferation by the bispecific <ANG2-VEGF> antibodies was measured according to the assay principle described above the Results are shown in FIG. 5.

Example 3b

ANG2-VEGF-Mab Tie2 Phoshorylation Inhibition

Inhibition of ANG2 induced Tie2 phosphorylation by the bispecific <ANG2-VEGF> antibodies was measured according to the assay principle. Described above the Results are shown in FIG. 6.

Example 4

Internalization/Downregulation of IGF-1R by Bispecific <EGFR-IGF1R> Antibodies

The human anti-IGF-1R antibody <IGF-1R> HUMAB Clone 18 (DSM ACC 2587) inhibits IGF-1R signaling and induces internalization and subsequent downregulation of IGF-1R. To evaluate the potential inhibitory activity of bispecific <EGFR-IGF1R> antibodies, the degree of downregulation of IGF-1R was analyzed.

In order to detect effects of the antibody of the invention on the amount of IGF-1 receptor (IGF-1R) in tumor cells, time-course experiments and subsequent ELISA analysis with IGF-1R and EGFR specific antibodies were performed.

Human H322M tumor cells (obtained from NCI) were cultivated in 96 well plates ($1\times10^4$ cells/well) over night at 37° C. and 5% $CO_2$ in RPMI medium supplemented with 10% fetal bovine serum, 2 mM L-glutamine and 1% Pen-Strep.

The medium was carefully removed and replaced by bispecific <EGFR-IGF1R> antibody solution diluted in RPMI medium in a total volume of 100 μl. Cells were incubated at 37° C. and 5% $CO_2$ for at least 3 but no more than 24 hours.

The medium was carefully removed by aspiration and cells were lysed with 120 μl/well of cold MES-lysis buffer (25 mM MES pH 6.5, 2% Triton X-100, 60 nM Octylglucoside, 150 mM NaCl, 10 mM $Na_3VO_4$, and Complete® protease inhibitor). Plates were stored at −20° C. until further analysis.

For IGF-1R Detection

A 1:200 dilution of antibody AK1a-Biotinylated (<IGF-1R> HUMAB Clone 1a (DSM ACC 2586) described in WO2004/087756, Roche, Germany) in PBS, 3% BSA and 0.2% Tween®20 at a final concentration of 2.4 μg/ml was added to each well of a streptavidin-coated MTP (Roche ID. No.: 11965891001). The streptavidin-MTP was agitated for 1 hour at RT and then washed three times with 200 μl per well of PBS containing 0.1% Tween®20.

After removal of the PBS/Tween®20 solution, 100 μl cell lysate was added to each well of the antibody coated streptavidin-MTP.

The MTPs were then incubated for another hour at RT with agitation and washed 3 times with PBS containing 0.1% Tween®20 subsequently.

IGF-1β rabbit antibody (200 μg/ml, Santa Cruz Biotechnology, Cat. No. sc-713) diluted 1:750 in PBS, 3% BSA and 0.2% Tween®20 was used to detect IGF-1R bound by the capture antibody AK1a. 100 μl was added per well and incubated for 1 hour at RT with constant agitation. The solution was removed subsequently and the wells were washed three times with 200 μl of PBS containing 0.1% Tween 20. The peroxidase labeled anti-rabbit IgG-HRP (Cell signaling Cat. No. 7074) was used as secondary detection antibody in a dilution of 1:4000 in PBS, 3% BSA and 0.2% Tween®20. 100 μl of it was added to each well and incubated for 1 hour at RT with agitation. The plate was then washed six times with PBS containing 0.1% Tween®20 solution. 100 μl per well of the peroxidase substrate 3,3'-5, 5'-Tetramethylbenzidin (Roche, BM-Blue ID-No.: 11484581) were added and incubated for 20 minutes at RT with agitation. The colourigenic reaction was stopped by adding 25 μl per well of 1M $H_2SO_4$ and incubating for another 5 minutes at RT. The absorbance was measured at 450 nm.

The bispecific <EGFR-IGF1R> antibody OA-GA201-scFab-Ak18_WT induces less downregulation than the human anti-IGF-1R antibody <IGF-1R> HUMAB Clone 18. Downregulation by OA-GA201-scFab-Ak18_WT was reduced by >50% compared to <IGF-1R> HUMAB Clone 18.

Example 5

Inhibition of EGFR—as Well as IGF-1R-Signaling Pathways by Bispecific <EGFR-IGF1R> Antibodies The human anti-IGF-1R antibody <IGF-1R> HUMAB Clone 18 (DSM ACC 2587) inhibits IGF-1R-signaling and the humanized rat anti-EGFR antibody ICR62 inhibits the signaling by EGFR. To evaluate the potential inhibitory activity of bispecific <EGFR-IGF1R> antibodies, the degree of inhibition of signaling towards both pathways was analyzed.

Human tumor cells (H322M, $3\times10^4$ cells/well) in RPMI medium supplemented with 10% fetal bovine serum, 2 mM L-glutamine and 1% PenStrep were seeded in 96-well microtiter plates and cultivated over night at 37° C. and 5% $CO_2$.

The medium was carefully removed and replaced by 100 μl serum-free DMEM medium (supplemented with 1 mg/ml RSA, 10 mM Hepes, 1% PenStrep) and incubated for at least 2.5 hours at 37° C. and 5% $CO_2$.

The medium was again carefully removed and replaced by a dilution of bispecific antibodies, and control antibodies (<IGF-1R> HUMAB Clone 18 and <EGFR>ICR62 final concentration 0.01 mg/ml) in serum-free DMEM medium at a total volume of 50 μl followed by an incubation for 30 min at 37° C. and 5% $CO_2$. Cells were stimulated by the addition of 50 μl IGF-1 (10 nM) or EGF (20 ng/ml) (diluted in serum-free DMEM medium) and incubated for 10 min at 37° C. and 5% $CO_2$.

The medium was carefully removed and cells were washed once with 100 μl/well of ice cold PBS. Cells were lysed by the addition of 100 μl/well BioRad Cell Lysis buffer (BioRad Cell Lysis Kit (BioRad Cat #171-304012) Plates were stored at −20° C. until further analysis.

Cell debris was removed by filtering cell lysates through MultiScreen HTS-filter plates by centrifugation at 500 g for 5 min. EGFR and IGF-1R phosphorylation in filtered cell lysates was analysed with a Luminex® system using the P-EGFR (Tyr) bead kit (Millipore Cat. #46-603) for the analysis of EGFR phosphorylation and the P-IGF-1R (Tyr1131) bead kit (BioRad Cat. #171V27343) for the analysis of IGF-1R phosphorylation. The Luminex® assays were performed as described in the BioPlex® Phosphoprotein Detection manual (BioRad Bulletin #2903) using Phosphoprotein Detection Reagent Kits (BioRad Cat. #171-304004).

The bispecific <EGFR-IGF1R> antibody OA-GA201-scFab-Ak18_WT effectively inhibits the phosphorylation of IGF-1R (IC50: 1 nM, maximal inhibition: >70%) and the phosphorylation of EGFR (IC50: 1 nM, maximal inhibition: >90%) on H322M tumor cells.

Example 6

Growth Inhibition of NCI-H322M Tumor Cells in 3D Culture by Bispecific <EGFR-IGF1R> Antibodies The human anti-IGF-1R antibody <IGF-1R> HUMAB Clone 18 (DSM ACC 2587) inhibits the growth of tumor cell lines that express IGF-1R (WO 2005/005635). In a similar manner, the humanized rat anti-EGFR antibody <EGFR>ICR62 has been shown to inhibit the growth of tumor cell lines that express EGFR (WO 2006/082515). To evaluate the potential inhibitory activity of bispecific <EGFR-IGF1R> antibodies in growth assays of tumor cell lines, the degree of inhibition in H322M cells which express EGFR as well as IGF-1R was analyzed.

H322M lung carcinoma cells (NCI) were cultured in RPMI 1640 medium (PAA, Pasching, Austria) supplemented with 10% FBS (PAA), 1 mM sodium pyruvate (Gibco, Darmstadt, Germany), non-essential amino acids (Gibco) and 2 mM L-glutamine (Sigma, Steinheim, Germany). 25000 cells/well were seeded in 96-well poly-HEMA (poly(2-hydroxyethylmethacrylate) (Polysciences, Warrington, Pa., USA)) coated plates containing the culture medium. Concomitantly, different concentrations of bispecific antibodies were added and incubated for 7 days. The CellTiterGlo® (Promega, Madison, Wis., USA) assay was used to detect cell viability by measuring the ATP-content of the cells according to the manufacturer's instructions.

Figure 8:
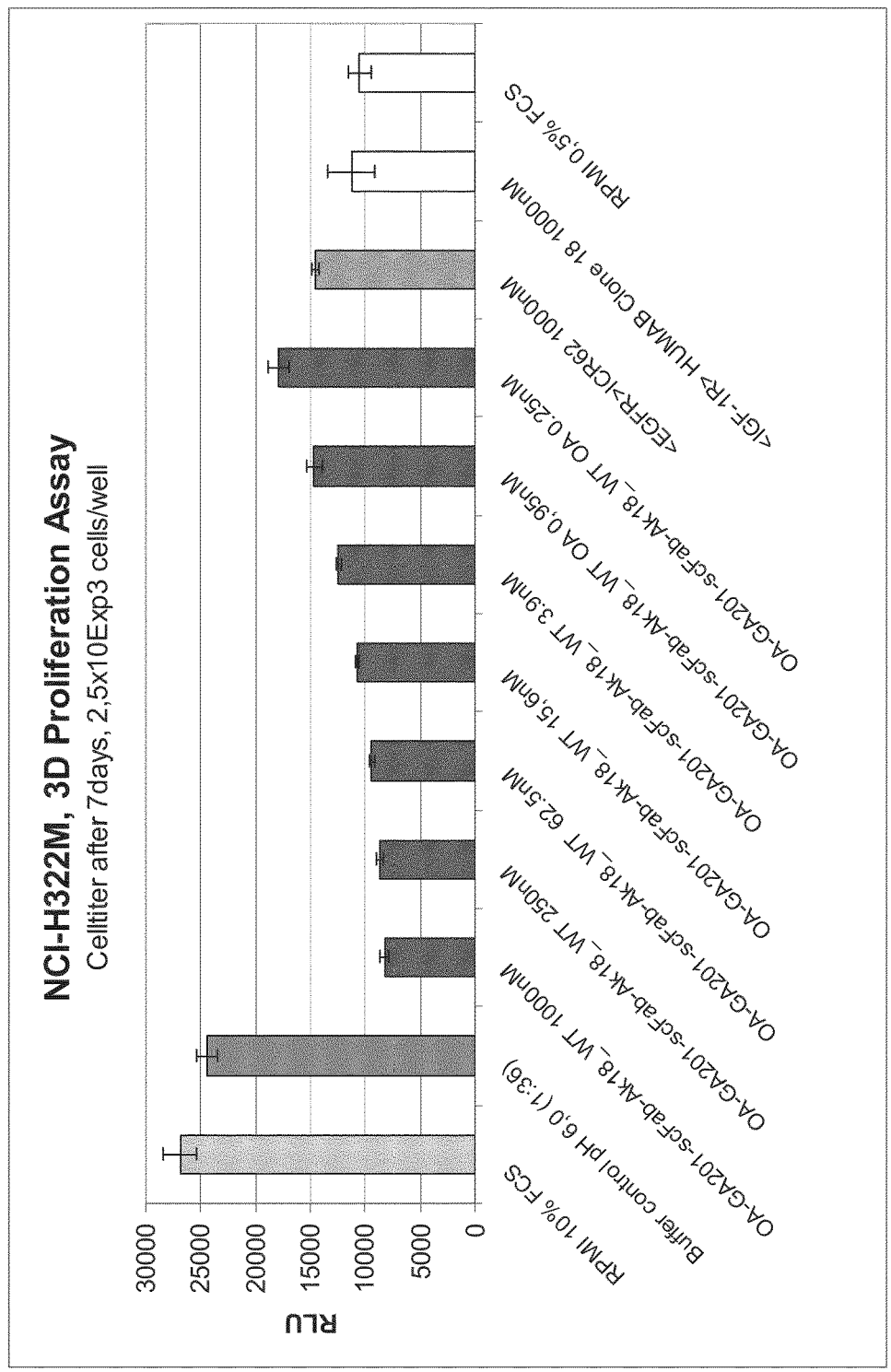
FIG. 8 Growth inhibition of H322M cancer cells by the bispecific (dose-dependently) compared to the parental monospecific antibodies <IGF-1R> HUMAB Clone 18 or <EGFR>ICR62.

Results were shown in FIG. 8. The bispecific <EGFR-IGF1R> antibody OA-GA201-scFab-Ak18_WT dose-dependently inhibits proliferation of H322M cells. At a dose of 1000 nM the bispecific <EGFR-IGF1R> antibody OA-GA201-scFab-Ak18_WT showed improved inhibition of proliferation when compared to the parental monospecific antibodies <IGF-1R> HUMAB Clone 18 or <EGFR>ICR62.

Example 7

In Vivo Efficacy of Bispecific <EGFR-IGF1R> Antibodies in a Subcutaneous Xenograft Model with EGFR and IGF-1R Expression The human anti-IGF-1R antibody <IGF-1R> HUMAB Clone 18 (DSM ACC 2587) inhibits the growth of tumor cell lines that express IGF-1R (WO 2005/005635). In a similar manner, the humanized rat anti-EGFR antibody <EGFR>ICR62 has been shown to inhibit the growth of tumor cell lines that express EGFR (WO 2006/082515). To evaluate the potential inhibitory activity of bispecific <EGFR-IGF1R> antibodies on in vivo tumor growth the subcutaneous xenograft model BxPC-3 that was characterized by the expression of EGFR as well as IGF-1R was used.

Cells of the human pancreatic carcinoma cell line BxPC-3 (obtained from ATCC) were cultured in RPMI 1640 medium (PAN™ Biotech GmbH), supplemented with 10% fetal bovine serum (Sera Plus; PAN™ Biotech GmbH) and 2 mM L-glutamine (PAN™ Biotech GmbH) at 37° C. in a water saturated atmosphere at 5% $CO_2$. At the day of inoculation, BxPC-3 tumor cells were harvested (1× trypsin-EDTA, Roche Diagnostics) from culture flasks and transferred into culture medium, centrifuged, washed once and re-suspended in PBS. For injection of cells, the final titer was adjusted to $1×10^8$ cells/ml. Subsequently 100 µl of this suspension (corresponding to $1×10^7$ cells) were injected subcutaneously into the right flank of female SCID beige mice. Treatment with vehicle, <EGFR-IGF1R> antibodies and control antibodies (<IGF-1R> HUMAB Clone 18 and <EGFR>ICR62) started after tumors were established and have reached an average size of 150-250 $mm^3$. Tumor volume was measured twice a week and animal weights were monitored in parallel. Single treatments and combination of the single antibodies were compared to the therapy with bispecific antibody.

Figure 10:
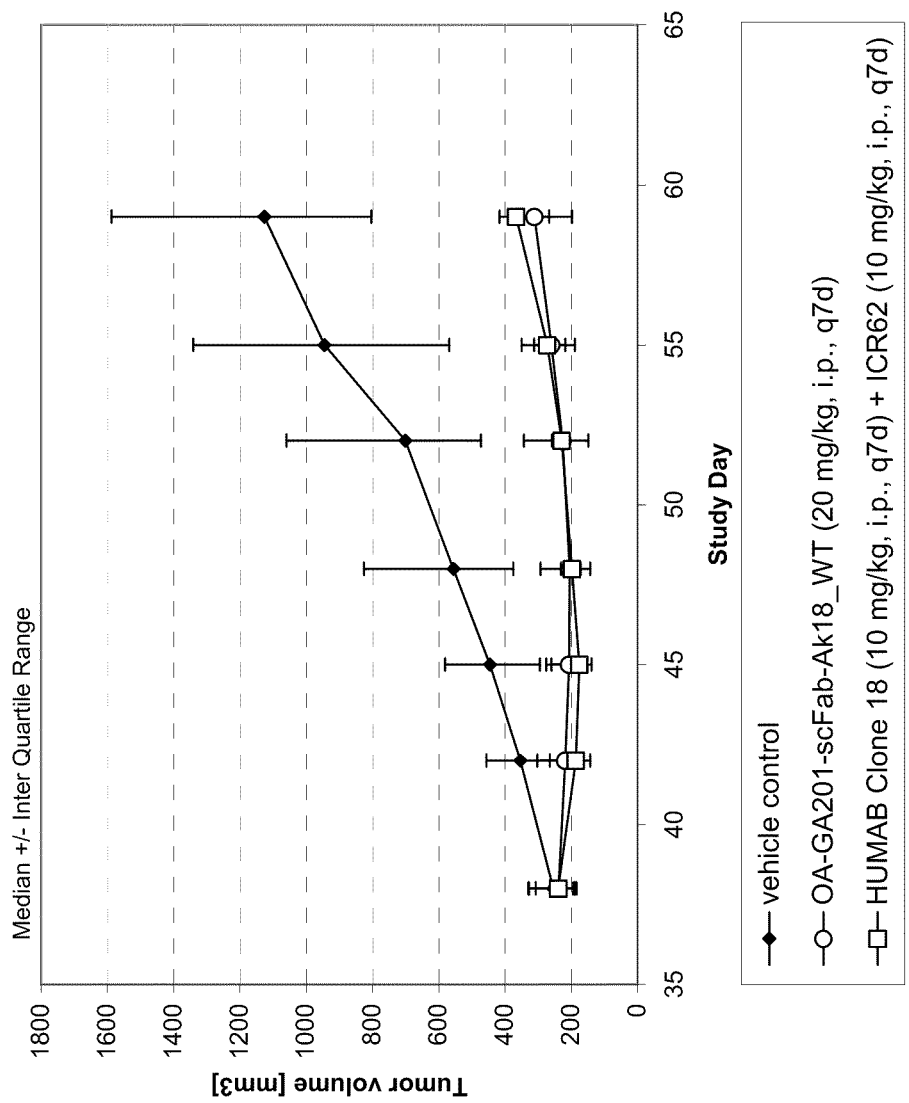
FIG. 10 Tumor growth inhibition in BxPC3 Xenograft model by OA-GA201-scFab-Ak18_WT compared to the combination of parental monospecific antibodies <IGF-1R> HUMAB Clone 18 and <EGFR>ICR62

The bispecific <EGFR-IGF1R> antibody OA-GA201-scFab-Ak18_WT (20 mg/kg; i.p., once weekly (q7d)) showed strong anti-tumor efficacy in the s.c. BxPC3 xenograft model see FIG. 10 and Table below) and inhibited tumor growth slightly better than the combination of monospecific antibodies <IGF-1R> HUMAB Clone 18 (10 mg/kg; i.p., once weekly (q7d)) and <EGFR>ICR62 (10 mg/kg; i.p., once weekly (q7d))

|  | TGI | TCR |
| --- | --- | --- |
| OA-GA201-scFab-Ak18_WT (20 mg/kg; i.p. q7d) | 93.5% | 0.26 |
| HUMAB Clone 18 (10 mg/kg; i.p. q7d) + ICR62 (10 mg/kg; i.p. q7d) | 91.5% | 0.27 |

Example 8

Preparation of the Glycoengineered Derivatives of Bispecific <EGFR-IGF1R> Antibodies Glycoengineered derivatives of bispecific <EGFR-IGF1R> antibodies were produced by co-transfecting HEK293-EBNA cells with the mammalian antibody heavy and light chain expression vectors using a calcium phosphate-transfection approach. Exponentially growing HEK293-EBNA cells were transfected by the calcium phosphate method. For the production of unmodified antibody, the cells were transfected only with antibody heavy and light chain expression vectors in a 1:1 ratio. For the production of the glycoengineered antibody, the cells are co-transfected with four plasmids, two for antibody expression, one for a fusion GnTIII polypeptide expression, and one for mannosidase II expression at a ratio of 4:4:1:1, respectively. Cells were grown as adherent monolayer cultures in T flasks using DMEM culture medium supplemented with 10% FCS, and were transfected when they were between 50 and 80% confluent. For the transfection of a T75 flask, 7.5 (to 8) million cells were seeded 24 hours before transfection in ca 14 ml DMEM culture medium supplemented with FCS (at 10% V/V final), (eventually 250 µg/ml neomycin,) and cells were placed at 37° C. in an incubator with a 5% CO2 atmosphere overnight. For each T75 flask to be transfected, a solution of DNA, CaCl2 and water was prepared by mixing 47 µg total plasmid vector DNA divided equally between the light and heavy chain expression vectors, 235 µl of a 1M CaCl2 solution, and adding water to a final volume of 469 µl. To this solution, 469 µl of a 50 mM HEPES, 280 mM NaCl, 1.5 mM Na2HPO4 solution at pH 7.05 were added, mixed immediately for 10 sec and left to stand at room temperature for 20 sec. The suspension was diluted with ca. 12 ml of DMEM supplemented with 2% FCS, and added to the T75 in place of the existing medium. The cells were incubated at 37° C., 5% CO2 for about 17 to 20 hours, then medium was replaced with ca. 12 ml DMEM, 10% FCS. The conditioned culture medium was harvested 5 to 7 days post-transfection centrifuged for 5 min at 210-300*g, sterile filtered through a 0.22 µm filter (or alternatively centrifuged for 5 min at 1200 rpm, followed by a second centrifugation for 10 min at 4000 rpm) and kept at 4° C.

The secreted antibodies were purified by Protein A affinity chromatography, and a final size exclusion chromatographic step on a Superdex 200 column (Amersham Pharmacia) exchanging the buffer to phosphate buffer saline and collecting the pure monomeric IgG1 antibodies. Antibody concentration is estimated using a spectrophotometer from the absorbance at 280 nm. The antibodies are formulated in a 25 mM potassium phosphate, 125 mM sodium chloride, 100 mM glycine solution of pH 6.7.

Glycoengineered variants of the bispecific antibodies were produced by co-transfection of the antibody expression vectors together with a GnT-III glycosyltransferase expression vector, or together with a GnT-III expression vector plus a Golgi mannosidase II expression vector. Glycoengineered antibodies were purified and formulated as described above for the non-glycoengineered antibodies. The oligosaccharides attached to the Fc region of the antibodies were analysed by MALDI/TOF-MS as described below to determine the amount of fucose.

| Purification Glycoengineered | Protein A | | SEC | |
|---|---|---|---|---|
| Construct | Yield | Monomer | Yield | Monomer |
| OA-GA201-scFab-Ak18_WT GE GE (4.2 L) | 87.3 mg | 92.0% (Analyt. SEC) | 65.1 mg | 100.0% (Analyt. SEC) |

Oligosaccharides are enzymatically released from the antibodies by PNGaseF digestion, with the antibodies being either immobilized on a PVDF membrane or in solution.

The resulting digest solution containing the released oligosaccharides is either prepared directly for MALDI/TOF-MS analysis or is further digested with EndoH glycosidase prior to sample preparation for MALDI/TOF-MS analysis. For all bispecific antibodies according to the invention, GE means glycoengineered.

Example 9

Binding to FcgRIIIa and ADCC-Competence of Bispecific <EGFR-IGF1R> Antibodies

The degree of ADCC mediation by a given antibody depends not only on the antigen that is bound, but is also dependent on affinities of constant regions to the FcgRIIIa, which is known as the Fc receptor that triggers the ADCC reaction. For the analysis of binding of the bispecific <EGFR-IGF1R> antibodies to the FcgRIIIa, a BIACORE technology is applied. By this technology, binding of bispecific <EGFR-IGF1R> antibodies to recombinantly produced FcgRIIIa domains is assessed.

All surface plasmon resonance measurements are performed on BIACORE™ 3000 instrument (GE Healthcare Biosciences AB, Sweden) at 25° C. The running and dilution buffer was PBS (1 mM KH2PO4, 10 mM Na2HPO4, 137 mM NaCl, 2.7 mM KCl), pH6.0, 0.005% (v/v) Tween®20. The soluble human FcgRIIIa was diluted in 10 mM sodium-acetate, pH 5.0 and immobilized on a CM5 biosensor chip using the standard amine coupling kit (GE Healthcare Biosciences AB, Sweden) to obtain FcgRIIIa surface densities of approximately 1000 RU. HBS-P (10 mM HEPES, pH 7.4, 150 mM NaCl, 0.005% Surfactant P20; GE Healthcare Biosciences AB, Sweden) is used as running buffer during immobilization. XGFR bispecific antibodies are diluted with PBS, 0.005% (v/v) Tween®20, pH6.0 to a concentration of 450 nM and injected over 3 minutes at a flow rate of 30 µl/minute. Then, the sensor chip is regenerated for 1 minute with PBS, pH8.0, 0.005% (v/v) Tween®20. Data analysis is performed with the BIAevaluation software (GE Healthcare Biosciences AB, Sweden).

To analyze to what degree the binding competency of bispecific <EGFR-IGF1R> antibodies to FcgRIIIa translates also into in-vitro ADCC activity towards tumor cells, ADCC competency is determined in cellular assays. For these assays, glycomodified derivatives bispecific <EGFR-IGF1R> antibodies are prepared (see above) and tested in a BIACORE™ ADCC-competence assay format and also an in-vitro ADCC assay as described below.

Human peripheral blood mononuclear cells (PBMC) are used as effector cells and were prepared using Histopaque®-1077 (Greiner Leucosep #227288) following essentially the manufacturer's instructions. In brief, venous blood is taken with heparinized syringes from healthy volunteers. The blood is diluted 1:0.75-1.3 with PBS (not containing Ca++ or Mg++) and layered on Histopaque-1077. The gradient was centrifuged at 800×g for 30 min at room temperature (RT) without breaks. The interphase containing the PBMC is collected and washed with PBS (50 ml per cells from two gradients) and harvested by centrifugation at 400×g for 10 minutes at RT. After resuspension of the pellet with PBS, the PBMC are counted and washed a second time by centrifugation at 400×g for 10 minutes at RT. The cells are then resuspended in the appropriate medium for the subsequent procedures.

The effector to target ratio used for the ADCC assays is 25:1 for PBMC. The effector cells are prepared in AIM-V medium at the appropriate concentration in order to add 50 µl per well of round bottom 96 well plates. Target cells were human EGFR/IGFR expressing cells (e.g., H322M, A549, or MCF-7) grown in DMEM containing 10% FCS.

Target cells are washed in PBS, counted and adjusted at 1×10E6 cells/ml. Cells are labeled with Calcein AM (10 µM) for 30 min at 37°/5% CO2. After labeling cells are washed twice in PBS and seeded at 5000 cells/well in 50 µl (AIM-V medium) in 96-well round bottom plates. Antibodies are diluted in AIM-V, added in 50 µl to the pre-plated target cells. Then the effector cells are added and the plate is incubated for 4 hours at 37° C. in a humidified atmosphere containing 5% CO2. After the incubation period plates are centrifuged at 200 g for 10 min and 80 µl supernatant is transferred to a black fluorescent plate/transparent bottom and fluorescence (Ex 485 nm/Em 535 nm) is measured with a Tecan Infinite® reader.

Following controls are included in the assay:

background: 50 µl supernatant-aliquot after labeling of cells+100 µl medium spontaneous lysis: 50 µl target cell suspension+100 µl medium maximum lysis: 50 µl target cell suspension+100 µl medium/1.5% Triton X-100 lysis control w/o antibody: 50 µl target cell suspension+50 µl medium+50 µl PBL's % antibody dependent cytotoxicity is calculated as follows:

% ADCC=x–spontaneous release/max. lysis–spontaneous lysis×100

Example 10

Analysis of Glycostructure of Bispecific <EGFR-IGF1R> Antibodies

For determination of the relative ratios of fucose- and non-fucose (a-fucose) containing oligosaccharide structures, released glycans of purified antibody material are analyzed by MALDI-Tof-mass spectrometry. For this, the antibody sample (about 50 µg) is incubated over night at 37° C. with 5 mU N-Glycosidase F (Prozyme# GKE-5010B) in 0.1M sodium phosphate buffer, pH 6.0, in order to release the oligosaccharide from the protein backbone. Subsequently, the glycan structures released are isolated and desalted using NuTip®-Carbon pipet tips (obtained from Glygen: NuTip®-10 µl, Cat.Nr#NT1CAR). As a first step, the NuTip®-Carbon pipet tips are prepared for binding of the oligosaccharides by washing them with 3 µL 1M NaOH followed by 20 µL pure water (e.g. HPLC-gradient grade from Baker, #4218), 3 µL 30% v/v acetic acid and again 20 µl pure water. For this, the respective solutions are loaded onto the top of the chromatography material in the NuTip®-Carbon pipet tip and pressed through it. Afterwards, the glycan structures corresponding to 10 µg antibody are bound to the material in the NuTip®-Carbon pipet tips by pulling up and down the N-Glycosidase F digest described above four to five times. The glycans bound to the material in the NuTip®-Carbon pipet tip are washed with 20 µL pure water in the way as described above and are eluted stepwise with 0.5 µL 10% and 2.0 µL 20% acetonitrile, respectively. For this step, the elution solutions are filled in a 0.5 mL reaction vails and are pulled up and down four to five times each. For the analysis by MALDI-Tof mass spectrometry, both eluates are combined. For this measurement, 0.4 µL of the combined eluates are mixed on the MALDI target with 1.6 µL SDHB matrix solution (2.5-Dihydroxybenzoic acid/2-Hydorxy-5-Methoxybenzoic acid [Bruker Daltonics #209813] dissolved in 20% ethanol/5 mM NaCl at 5 mg/ml) and analysed with a suitably tuned Bruker Ultraflex TOF/TOF instrument. Routinely, 50-300 shots are recorded and summed up to a single experiment. The spectra obtained are evaluated by the flex analysis software (Bruker Daltonics) and masses are determined for the each of the peaks detected. Subsequently, the peaks are assigned to fucose or a-fucose (non-fucose) containing glycol structures by comparing the masses calculated and the masses theoretically expected for the respective structures (e.g. complex, hybride and oligo- or high-mannose, respectively, with and without fucose).

For determination of the ratio of hybride structures, the antibody sample are digested with N-Glycosidase F and Endo-Glycosidase H concomitantly N-glycosidase F releases all N-linked glycan structures (complex, hybride and oligo- and high mannose structures) from the protein backbone and the Endo-Glycosidase H cleaves all the hybride type glycans additionally between the two GlcNAc-residue at the reducing end of the glycan. This digest is subsequently treated and analysed by MALDI-Tof mass spectrometry in the same way as described above for the N-Glycosidase F digested sample. By comparing the pattern from the N-Glycosidase F digest and the combined N-glycosidase F/Endo H digest, the degree of reduction of the signals of a specific glyco structure is used to estimate the relative content of hybride structures.

The relative amount of each glycostructure is calculated from the ratio of the peak height of an individual glycol structure and the sum of the peak heights of all glyco structures detected. The amount of fucose is the percentage of fucose-containing structures related to all glyco structures identified in the N-Glycosidase F treated sample (e.g. complex, hybride and oligo- and high-mannose structures, resp.). The amount of afucosylation is the percentage of fucose-lacking structures related to all glyco structures identified in the N-Glycosidase F treated sample (e.g. complex, hybride and oligo- and high-mannose structures, resp.).

The amount of fucose determined for OA-GA201-scFab-Ak18_WT was between 25% and 40%.

Example 11

Binding of Bispecific <EGFR-IGF1R> Antibodies to Cells with Different EGFR and IGF-1R Expression The human anti-IGF-1R antibody <IGF-1R> HUMAB Clone 18 (DSM ACC 2587) binds to cells expressing IGF-1R and the humanized rat anti-EGFR antibody ICR62 binds to cells that express EGFR on their surface. To evaluate the binding properties of bispecific <EGFR-IGF1R> antibodies compared to monospecific bivalent antibodies towards EGFR and IGF-1R, competitive binding assays were performed on cells with different IGF-1R/EGFR expression ratio.

Human tumor cells (e.g. A549, TC-71, MDA-MB-231, 2×105 cells/well) diluted in ice-cold buffer (PBS+2% FCS, Gibco) were added to a mixture of labeled monospecific antibodies (HUMAB Clone 18 or humanized rat anti-EGFR antibody ICR62) (final concentration of 1 µg/ml) and different concentrations of unlabeled <EGFR-IGF1R> antibodies or unlabeled monospecific antibodies or Fab fragments as controls (final titration range of 100 to 0.002 µg/ml) in a 96-well microtiter plate. The mixture was incubated on ice for 45 minutes. Cells were washed 2 times by addition of 150-200 µl buffer (PBS+2% FCS) and subsequent centrifugation (300 g; 5 min, 4° C.). The cells were then resuspended in 200 µl fixation buffer (1× CellFix, BD #340181) containing 6.25 µl/ml 7-AAD (BD #559925) and incubated for 10-20 min on ice to allow for fixation and penetration of 7-AAD in dead cells. Fluorescent signal of the samples was analysed by FACS and IC50 values were calculated.

The results of the competitive binding analysis versus <IGF-1R> HUMAB Clone 18 (IC50 values) are shown in Table X. On A549 tumor cells, expressing both IGF-1R and EGFR, binding of the bispecific <EGFR-IGF1R> antibody OA-GA201-scFab-Ak18_WT was superior to <IGF-1R> HUMAB Clone 18 (~3×) and superior to the <IGF-1R> HUMAB Clone 18 Fab fragment (~30×) likely due to the ability of the bispecific antibody to bind both IGF-1R and EGFR simultaneously (avidity effects). On TC-71 tumor cells, expressing IGF-1R but not EGFR binding of <EGFR-IGF1R> antibody OA-GA201-scFab-Ak18_WT was comparable to the IGF-1R> HUMAB Clone 18 Fab fragment. In this setting, were only IGF-1R but not EGFR is expressed OA-GA201-scFab-Ak18_WT can only bind to IGF-1R with one binding arm.

This capacity of bispecific <EGFR-IGF1R> antibodies to bind stronger to cells expressing IGF-1R and EGFR can be exploited to achieve superior targeting to tumor tissue and potentially resulting in favorable safety profiles and PK properties compared to monospecific IGF-1R and EGFR targeting antibodies.

| Cell line | Test compound (unlabeled) | Competing compound (labeled) | IC50 [nM] Exp. #1 | IC50 [nM] Exp. #2 |
|---|---|---|---|---|
| A549 | <IGF-1R> HUMAB Clone 18 | <IGF-1R> HUMAB Clone 18 | 1.6 | 1.5 |
| A549 | <IGF-1R> HUMAB Clone 18 Fab fragment | <IGF-1R> HUMAB Clone 18 | 21.1 | 19.3 |
| A549 | <EGFR-IGF1R> antibody OA-GA201-scFab-Ak18_WT | <IGF-1R> HUMAB Clone 18 | 0.6 | 0.6 |
| TC-71 | <IGF-1R> HUMAB Clone 18 | <IGF-1R> HUMAB Clone 18 | 1.4 | 1.5 |
| TC-71 | <IGF-1R> HUMAB Clone 18 Fab fragment | <IGF-1R> HUMAB Clone 18 | 24.6 | 26.2 |
| TC-71 | <EGFR-IGF1R> antibody OA-GA201-scFab-Ak18_WT | <IGF-1R> HUMAB Clone 18 | 24.3 | 24.9 |

We claim:

1. A bispecific, bivalent antibody comprising
a) a heavy chain and a light chain of a first full length antibody that specifically binds to a first antigen; and
b) a heavy chain and a light chain of a second full length antibody that specifically binds to a second antigen, wherein the N-terminus of the heavy chain of the second full length antibody is connected to the C-terminus of the light chain of the second full length antibody via a peptide linker, and
wherein the heavy chain and the light chain of the first full length antibody are not fused via a peptide linker.

2. The antibody according to claim 1, wherein the antibody comprises a first CH3 domain and a second CH3 domain that meet at an interface which comprises an alteration in the original interface between the antibody CH3 domains;
wherein
i) in the first CH3 domain an amino acid residue is replaced with an amino acid residue having a larger side chain volume, thereby generating a protuberance within the interface of the CH3 domain of the first heavy chain which is positionable in a cavity within the interface of the second CH3 domain
and wherein
ii) in the second CH3 domain an amino acid residue is replaced with an amino acid residue having a smaller side chain volume, thereby generating a cavity within the interface of the second CH3 domain within which the protuberance within the interface of the first CH3 domain is positionable.

3. The antibody according to claim 2, wherein
the amino acid residue having a larger side chain volume is selected from the group consisting of arginine (R), phenylalanine (F), tyrosine (Y), and tryptophan (W) and
the amino acid residue having a smaller side chain volume is selected from the group consisting of alanine (A), serine (S), threonine (T), and valine (V).

4. The antibody according to claim 2, wherein
both CH3 domains are further altered by the introduction of cysteine (C) as amino acid in the corresponding positions of each CH3 domain such that a disulfide bridge between both CH3 domains can be formed.

5. The antibody according to claim 1, wherein
the antibody heavy chain variable domain (VH) and the antibody light chain variable domain (VL) of the second full length antibody are disulfide stabilized by introduction of a disulfide bond between the following positions:
i) heavy chain variable domain position 44 to light chain variable domain position 1 00,
ii) heavy chain variable domain position 105 to light chain variable domain position 43, or
iii) heavy chain variable domain position 1 01 to light chain variable domain position 100.

6. The antibody according to claim 1, wherein the antibody comprises a constant region of IgG1.

7. The antibody according to claim 1, wherein
a) the heavy chain of the first full length antibody comprises the amino acid sequence of SEQ ID NO: 5 and the light chain of the first full length antibody comprises the amino acid sequence of SEQ ID NO: 6 and wherein the first antigen to which the first full length antibody specifically binds is EGFR, and
b) the peptide connected heavy and light chain of the second full length antibody comprises the amino acid sequence of SEQ ID NO: 8 and wherein the second antigen to which the second full length antibody specifically binds is IGF-1R.

8. The antibody according to claim 6, wherein the antibody is glycosylated with a sugar chain at Asn297 wherein the amount of fucose within the sugar chain is 65% or lower.

9. A pharmaceutical composition comprising an antibody according to claim 1.

10. A bispecific antibody that specifically binds to human IGF-1R and to human EGFR, wherein the antibody comprises a heavy chain and a light chain from a first antibody and a heavy chain and a light chain from a second antibody, wherein of
   a) the light chain of the first antibody which binds to IGF-1R comprises the amino acid sequence of SEQ ID NO: 1 and the heavy chain from the first antibody comprises the amino acid sequence of SEQ ID NO: 2, and the heavy and light chain from the second antibody which binds to EGFR comprise the amino acid sequence of SEQ ID NO: 3;
   b) the light chain of the first antibody which binds to EGFR comprises the amino acid sequence of SEQ ID NO: 1 and the heavy chain from the first antibody comprises the amino acid sequence of SEQ ID NO: 2, and the heavy and light chain from the second antibody which binds to IGF-1R comprise the amino acid sequence of SEQ ID NO: 4;
   c) the light chain of the first antibody which binds to EGFR comprises the amino acid sequence of SEQ ID NO: 5 and the heavy chain from the first antibody comprises the amino acid sequence of SEQ ID NO: 6, and the heavy and light chain from the second antibody which binds to IGF-1R comprise the amino acid sequence of SEQ ID NO: 7; or
   d) the light chain of the first antibody which binds to EGFR comprises the amino acid sequence of SEQ ID NO: 5 and the heavy chain from the first antibody comprises the amino acid sequence of SEQ ID NO: 6, and the heavy and light chain from the second antibody which binds IGF-1R comprise a peptide connected heavy and light chain comprising the amino acid sequence of SEQ ID NO: 8.

11. The antibody according to claim 10, wherein the antibody is glycosylated with a sugar chain at Asn297 wherein the amount of fucose within the sugar chain is 65% or lower.

* * * * *

SEQUENCE LISTING

```
<160> NUMBER OF SEQ ID NOS: 16

<210> SEQ ID NO 1
<211> LENGTH: 448
<212> TYPE: PRT
<213> ORGANISM: Artificial
<220> FEATURE:
<223> OTHER INFORMATION: <IGF-1R> heavy chain, OA-Ak18-scFab-GA201 (+WT)

<400> SEQUENCE: 1

Gln Val Glu Leu Val Glu Ser Gly Gly Gly Val Val Gln Pro Gly Arg
1               5                   10                  15

Ser Gln Arg Leu Ser Cys Ala Ala Ser Gly Phe Thr Phe Ser Ser Tyr
            20                  25                  30

Gly Met His Trp Val Arg Gln Ala Pro Gly Lys Gly Leu Glu Trp Val
        35                  40                  45

Ala Ile Ile Trp Phe Asp Gly Ser Ser Thr Tyr Tyr Ala Asp Ser Val
    50                  55                  60

Arg Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Phe Cys
                85                  90                  95

Ala Arg Glu Leu Gly Arg Arg Tyr Phe Asp Leu Trp Gly Arg Gly Thr
            100                 105                 110

Leu Val Ser Val Ser Ser Ala Ser Thr Lys Gly Pro Ser Val Phe Pro
        115                 120                 125

Leu Ala Pro Ser Ser Lys Ser Thr Ser Gly Gly Thr Ala Ala Leu Gly
    130                 135                 140

Cys Leu Val Lys Asp Tyr Phe Pro Glu Pro Val Thr Val Ser Trp Asn
145                 150                 155                 160

Ser Gly Ala Leu Thr Ser Gly Val His Thr Phe Pro Ala Val Leu Gln
                165                 170                 175

Ser Ser Gly Leu Tyr Ser Leu Ser Ser Val Val Thr Val Pro Ser Ser
            180                 185                 190

Ser Leu Gly Thr Gln Thr Tyr Ile Cys Asn Val Asn His Lys Pro Ser
        195                 200                 205

Asn Thr Lys Val Asp Lys Lys Val Glu Pro Lys Ser Cys Asp Lys Thr
    210                 215                 220
```

```
His Thr Cys Pro Pro Cys Pro Ala Pro Glu Leu Leu Gly Gly Pro Ser
225                 230                 235                 240

Val Phe Leu Phe Pro Pro Lys Pro Lys Asp Thr Leu Met Ile Ser Arg
                245                 250                 255

Thr Pro Glu Val Thr Cys Val Val Val Asp Val Ser His Glu Asp Pro
            260                 265                 270

Glu Val Lys Phe Asn Trp Tyr Val Asp Gly Val Glu Val His Asn Ala
        275                 280                 285

Lys Thr Lys Pro Arg Glu Glu Gln Tyr Asn Ser Thr Tyr Arg Val Val
    290                 295                 300

Ser Val Leu Thr Val Leu His Gln Asp Trp Leu Asn Gly Lys Glu Tyr
305                 310                 315                 320

Lys Cys Lys Val Ser Asn Lys Ala Leu Pro Ala Pro Ile Glu Lys Thr
                325                 330                 335

Ile Ser Lys Ala Lys Gly Gln Pro Arg Glu Pro Gln Val Cys Thr Leu
            340                 345                 350

Pro Pro Ser Arg Asp Glu Leu Thr Lys Asn Gln Val Ser Leu Ser Cys
        355                 360                 365

Ala Val Lys Gly Phe Tyr Pro Ser Asp Ile Ala Val Glu Trp Glu Ser
370                 375                 380

Asn Gly Gln Pro Glu Asn Asn Tyr Lys Thr Thr Pro Pro Val Leu Asp
385                 390                 395                 400

Ser Asp Gly Ser Phe Phe Leu Val Ser Lys Leu Thr Val Asp Lys Ser
                405                 410                 415

Arg Trp Gln Gln Gly Asn Val Phe Ser Cys Ser Val Met His Glu Ala
            420                 425                 430

Leu His Asn His Tyr Thr Gln Lys Ser Leu Ser Leu Ser Pro Gly Lys
        435                 440                 445

<210> SEQ ID NO 2
<211> LENGTH: 215
<212> TYPE: PRT
<213> ORGANISM: Artificial
<220> FEATURE:
<223> OTHER INFORMATION: <IGF-1R> light chain, OA-Ak18-scFab-GA201 (+WT)

<400> SEQUENCE: 2

Glu Ile Val Leu Thr Gln Ser Pro Ala Thr Leu Ser Leu Ser Pro Gly
1               5                   10                  15

Glu Arg Ala Thr Leu Ser Cys Arg Ala Ser Gln Ser Val Ser Ser Tyr
            20                  25                  30

Leu Ala Trp Tyr Gln Gln Lys Pro Gly Gln Ala Pro Arg Leu Leu Ile
        35                  40                  45

Tyr Asp Ala Ser Lys Arg Ala Thr Gly Ile Pro Ala Arg Phe Ser Gly
    50                  55                  60

Ser Gly Ser Gly Thr Asp Phe Thr Leu Thr Ile Ser Ser Leu Glu Pro
65                  70                  75                  80

Glu Asp Phe Ala Val Tyr Tyr Cys Gln Gln Arg Ser Lys Trp Pro Pro
                85                  90                  95

Trp Thr Phe Gly Gln Gly Thr Lys Val Glu Ser Lys Arg Thr Val Ala
            100                 105                 110

Ala Pro Ser Val Phe Ile Phe Pro Pro Ser Asp Glu Gln Leu Lys Ser
        115                 120                 125

Gly Thr Ala Ser Val Val Cys Leu Leu Asn Asn Phe Tyr Pro Arg Glu
    130                 135                 140
```

Ala Lys Val Gln Trp Lys Val Asp Asn Ala Leu Gln Ser Gly Asn Ser
145                 150                 155                 160

Gln Glu Ser Val Thr Glu Gln Asp Ser Lys Asp Ser Thr Tyr Ser Leu
            165                 170                 175

Ser Ser Thr Leu Thr Leu Ser Lys Ala Asp Tyr Glu Lys His Lys Val
            180                 185                 190

Tyr Ala Cys Glu Val Thr His Gln Gly Leu Ser Ser Pro Val Thr Lys
        195                 200                 205

Ser Phe Asn Arg Gly Glu Cys
    210                 215

<210> SEQ ID NO 3
<211> LENGTH: 695
<212> TYPE: PRT
<213> ORGANISM: Artificial
<220> FEATURE:
<223> OTHER INFORMATION: <EGFR> peptide connected heavy and light chain
      with disulfide stabilization VH 44 /VL100 ofOA-Ak18-scFab-GA201

<400> SEQUENCE: 3

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Gly Ile Asn Asn Tyr
            20                  25                  30

Leu Asn Trp Tyr Gln Gln Lys Pro Gly Lys Ala Pro Lys Arg Leu Ile
        35                  40                  45

Tyr Asn Thr Asn Asn Leu Gln Thr Gly Val Pro Ser Arg Phe Ser Gly
    50                  55                  60

Ser Gly Ser Gly Thr Glu Phe Thr Leu Thr Ile Ser Ser Leu Gln Pro
65                  70                  75                  80

Glu Asp Phe Ala Thr Tyr Tyr Cys Leu Gln His Asn Ser Phe Pro Thr
                85                  90                  95

Phe Gly Cys Gly Thr Lys Leu Glu Ile Lys Arg Thr Val Ala Ala Pro
            100                 105                 110

Ser Val Phe Ile Phe Pro Pro Ser Asp Glu Gln Leu Lys Ser Gly Thr
        115                 120                 125

Ala Ser Val Val Cys Leu Leu Asn Asn Phe Tyr Pro Arg Glu Ala Lys
    130                 135                 140

Val Gln Trp Lys Val Asp Asn Ala Leu Gln Ser Gly Asn Ser Gln Glu
145                 150                 155                 160

Ser Val Thr Glu Gln Asp Ser Lys Asp Ser Thr Tyr Ser Leu Ser Ser
            165                 170                 175

Thr Leu Thr Leu Ser Lys Ala Asp Tyr Glu Lys His Lys Val Tyr Ala
        180                 185                 190

Cys Glu Val Thr His Gln Gly Leu Ser Ser Pro Val Thr Lys Ser Phe
    195                 200                 205

Asn Arg Gly Glu Cys Gly Gly Gly Ser Gly Gly Gly Gly Ser Gly
    210                 215                 220

Gly Gly Gly Ser Gly Gly Gly Gly Ser Gly Gly Gly Gly Ser Gly Gly
225                 230                 235                 240

Gly Gly Ser Gly Gly Gln Val Gln Leu Val Gln Ser Gly Ala Glu Val
            245                 250                 255

Lys Lys Pro Gly Ser Ser Val Lys Val Ser Cys Lys Ala Ser Gly Phe
        260                 265                 270

Thr Phe Thr Asp Tyr Lys Ile His Trp Val Arg Gln Ala Pro Gly Gln
    275                 280                 285

-continued

Cys Leu Glu Trp Met Gly Tyr Phe Asn Pro Asn Ser Gly Tyr Ser Thr
290                 295                 300

Tyr Ala Gln Lys Phe Gln Gly Arg Val Thr Ile Thr Ala Asp Lys Ser
305                 310                 315                 320

Thr Ser Thr Ala Tyr Met Glu Leu Ser Ser Leu Arg Ser Glu Asp Thr
            325                 330                 335

Ala Val Tyr Tyr Cys Ala Arg Leu Ser Pro Gly Gly Tyr Tyr Val Met
        340                 345                 350

Asp Ala Trp Gly Gln Gly Thr Thr Val Thr Val Ser Ser Ala Ser Thr
    355                 360                 365

Lys Gly Pro Ser Val Phe Pro Leu Ala Pro Ser Ser Lys Ser Thr Ser
370                 375                 380

Gly Gly Thr Ala Ala Leu Gly Cys Leu Val Lys Asp Tyr Phe Pro Glu
385                 390                 395                 400

Pro Val Thr Val Ser Trp Asn Ser Gly Ala Leu Thr Ser Gly Val His
            405                 410                 415

Thr Phe Pro Ala Val Leu Gln Ser Ser Gly Leu Tyr Ser Leu Ser Ser
        420                 425                 430

Val Val Thr Val Pro Ser Ser Ser Leu Gly Thr Gln Thr Tyr Ile Cys
    435                 440                 445

Asn Val Asn His Lys Pro Ser Asn Thr Lys Val Asp Lys Lys Val Glu
450                 455                 460

Pro Lys Ser Cys Asp Lys Thr His Thr Cys Pro Pro Cys Pro Ala Pro
465                 470                 475                 480

Glu Leu Leu Gly Gly Pro Ser Val Phe Leu Phe Pro Pro Lys Pro Lys
            485                 490                 495

Asp Thr Leu Met Ile Ser Arg Thr Pro Glu Val Thr Cys Val Val Val
        500                 505                 510

Asp Val Ser His Glu Asp Pro Glu Val Lys Phe Asn Trp Tyr Val Asp
    515                 520                 525

Gly Val Glu Val His Asn Ala Lys Thr Lys Pro Arg Glu Glu Gln Tyr
530                 535                 540

Asn Ser Thr Tyr Arg Val Val Ser Val Leu Thr Val Leu His Gln Asp
545                 550                 555                 560

Trp Leu Asn Gly Lys Glu Tyr Lys Cys Lys Val Ser Asn Lys Ala Leu
            565                 570                 575

Pro Ala Pro Ile Glu Lys Thr Ile Ser Lys Ala Lys Gly Gln Pro Arg
        580                 585                 590

Glu Pro Gln Val Tyr Thr Leu Pro Pro Cys Arg Asp Glu Leu Thr Lys
    595                 600                 605

Asn Gln Val Ser Leu Trp Cys Leu Val Lys Gly Phe Tyr Pro Ser Asp
610                 615                 620

Ile Ala Val Glu Trp Glu Ser Asn Gly Gln Pro Glu Asn Asn Tyr Lys
625                 630                 635                 640

Thr Thr Pro Pro Val Leu Asp Ser Asp Gly Ser Phe Phe Leu Tyr Ser
            645                 650                 655

Lys Leu Thr Val Asp Lys Ser Arg Trp Gln Gln Gly Asn Val Phe Ser
        660                 665                 670

Cys Ser Val Met His Glu Ala Leu His Asn His Tyr Thr Gln Lys Ser
    675                 680                 685

Leu Ser Leu Ser Pro Gly Lys
690                 695

```
<210> SEQ ID NO 4
<211> LENGTH: 695
<212> TYPE: PRT
<213> ORGANISM: Artificial
<220> FEATURE:
<223> OTHER INFORMATION: <EGFR> peptide connected heavy and light chain
      of OA-Ak18-scFab-GA201_WT

<400> SEQUENCE: 4
```

| Asp | Ile | Gln | Met | Thr | Gln | Ser | Pro | Ser | Ser | Leu | Ser | Ala | Ser | Val | Gly |
|---|---|---|---|---|---|---|---|---|---|---|---|---|---|---|---|
| 1 | | | | 5 | | | | | 10 | | | | | 15 | |

| Asp | Arg | Val | Thr | Ile | Thr | Cys | Arg | Ala | Ser | Gln | Gly | Ile | Asn | Asn | Tyr |
|---|---|---|---|---|---|---|---|---|---|---|---|---|---|---|---|
| | | | 20 | | | | | 25 | | | | | 30 | | |

| Leu | Asn | Trp | Tyr | Gln | Gln | Lys | Pro | Gly | Lys | Ala | Pro | Lys | Arg | Leu | Ile |
| | | | 35 | | | | | 40 | | | | | 45 | | |

| Tyr | Asn | Thr | Asn | Asn | Leu | Gln | Thr | Gly | Val | Pro | Ser | Arg | Phe | Ser | Gly |
| | 50 | | | | | 55 | | | | | 60 | | | | |

| Ser | Gly | Ser | Gly | Thr | Glu | Phe | Thr | Leu | Thr | Ile | Ser | Ser | Leu | Gln | Pro |
| 65 | | | | | 70 | | | | | 75 | | | | | 80 |

| Glu | Asp | Phe | Ala | Thr | Tyr | Tyr | Cys | Leu | Gln | His | Asn | Ser | Phe | Pro | Thr |
| | | | | 85 | | | | | 90 | | | | | 95 | |

| Phe | Gly | Gln | Gly | Thr | Lys | Leu | Glu | Ile | Lys | Arg | Thr | Val | Ala | Ala | Pro |
| | | | 100 | | | | | 105 | | | | | 110 | | |

| Ser | Val | Phe | Ile | Phe | Pro | Pro | Ser | Asp | Glu | Gln | Leu | Lys | Ser | Gly | Thr |
| | | | 115 | | | | | 120 | | | | | 125 | | |

| Ala | Ser | Val | Val | Cys | Leu | Leu | Asn | Asn | Phe | Tyr | Pro | Arg | Glu | Ala | Lys |
| 130 | | | | | 135 | | | | | 140 | | | | | |

| Val | Gln | Trp | Lys | Val | Asp | Asn | Ala | Leu | Gln | Ser | Gly | Asn | Ser | Gln | Glu |
| 145 | | | | | 150 | | | | | 155 | | | | | 160 |

| Ser | Val | Thr | Glu | Gln | Asp | Ser | Lys | Asp | Ser | Thr | Tyr | Ser | Leu | Ser | Ser |
| | | | | 165 | | | | | 170 | | | | | 175 | |

| Thr | Leu | Thr | Leu | Ser | Lys | Ala | Asp | Tyr | Glu | Lys | His | Lys | Val | Tyr | Ala |
| | | | 180 | | | | | 185 | | | | | 190 | | |

| Cys | Glu | Val | Thr | His | Gln | Gly | Leu | Ser | Ser | Pro | Val | Thr | Lys | Ser | Phe |
| | | 195 | | | | | 200 | | | | | 205 | | | |

| Asn | Arg | Gly | Glu | Cys | Gly | Gly | Gly | Gly | Ser | Gly | Gly | Gly | Ser | Gly |
| 210 | | | | | 215 | | | | | 220 | | | | | |

| Gly | Gly | Gly | Ser | Gly | Gly | Gly | Ser | Gly | Gly | Gly | Ser | Gly | Gly |
| 225 | | | | | 230 | | | | | 235 | | | | | 240 |

| Gly | Gly | Ser | Gly | Gly | Gln | Val | Gln | Leu | Val | Gln | Ser | Gly | Ala | Glu | Val |
| | | | | 245 | | | | | 250 | | | | | 255 | |

| Lys | Lys | Pro | Gly | Ser | Ser | Val | Lys | Val | Ser | Cys | Lys | Ala | Ser | Gly | Phe |
| | | | 260 | | | | | 265 | | | | | 270 | | |

| Thr | Phe | Thr | Asp | Tyr | Lys | Ile | His | Trp | Val | Arg | Gln | Ala | Pro | Gly | Gln |
| | | 275 | | | | | 280 | | | | | 285 | | | |

| Gly | Leu | Glu | Trp | Met | Gly | Tyr | Phe | Asn | Pro | Asn | Ser | Gly | Tyr | Ser | Thr |
| | | 290 | | | | | 295 | | | | | 300 | | | |

| Tyr | Ala | Gln | Lys | Phe | Gln | Gly | Arg | Val | Thr | Ile | Thr | Ala | Asp | Lys | Ser |
| 305 | | | | | 310 | | | | | 315 | | | | | 320 |

| Thr | Ser | Thr | Ala | Tyr | Met | Glu | Leu | Ser | Ser | Leu | Arg | Ser | Glu | Asp | Thr |
| | | | | 325 | | | | | 330 | | | | | 335 | |

| Ala | Val | Tyr | Tyr | Cys | Ala | Arg | Leu | Ser | Pro | Gly | Gly | Tyr | Tyr | Val | Met |
| | | | 340 | | | | | 345 | | | | | 350 | | |

| Asp | Ala | Trp | Gly | Gln | Gly | Thr | Thr | Val | Thr | Val | Ser | Ser | Ala | Ser | Thr |
| | | | 355 | | | | | 360 | | | | | 365 | | |

```
Lys Gly Pro Ser Val Phe Pro Leu Ala Pro Ser Ser Lys Ser Thr Ser
    370                 375                 380

Gly Gly Thr Ala Ala Leu Gly Cys Leu Val Lys Asp Tyr Phe Pro Glu
385                 390                 395                 400

Pro Val Thr Val Ser Trp Asn Ser Gly Ala Leu Thr Ser Gly Val His
                405                 410                 415

Thr Phe Pro Ala Val Leu Gln Ser Ser Gly Leu Tyr Ser Leu Ser Ser
            420                 425                 430

Val Val Thr Val Pro Ser Ser Leu Gly Thr Gln Thr Tyr Ile Cys
        435                 440                 445

Asn Val Asn His Lys Pro Ser Asn Thr Lys Val Asp Lys Lys Val Glu
    450                 455                 460

Pro Lys Ser Cys Asp Lys Thr His Thr Cys Pro Pro Cys Pro Ala Pro
465                 470                 475                 480

Glu Leu Leu Gly Gly Pro Ser Val Phe Leu Phe Pro Pro Lys Pro Lys
                485                 490                 495

Asp Thr Leu Met Ile Ser Arg Thr Pro Glu Val Thr Cys Val Val Val
            500                 505                 510

Asp Val Ser His Glu Asp Pro Glu Val Lys Phe Asn Trp Tyr Val Asp
        515                 520                 525

Gly Val Glu Val His Asn Ala Lys Thr Lys Pro Arg Glu Glu Gln Tyr
    530                 535                 540

Asn Ser Thr Tyr Arg Val Val Ser Val Leu Thr Val Leu His Gln Asp
545                 550                 555                 560

Trp Leu Asn Gly Lys Glu Tyr Lys Cys Lys Val Ser Asn Lys Ala Leu
                565                 570                 575

Pro Ala Pro Ile Glu Lys Thr Ile Ser Lys Ala Lys Gly Gln Pro Arg
            580                 585                 590

Glu Pro Gln Val Tyr Thr Leu Pro Pro Cys Arg Asp Glu Leu Thr Lys
        595                 600                 605

Asn Gln Val Ser Leu Trp Cys Leu Val Lys Gly Phe Tyr Pro Ser Asp
    610                 615                 620

Ile Ala Val Glu Trp Glu Ser Asn Gly Gln Pro Glu Asn Asn Tyr Lys
625                 630                 635                 640

Thr Thr Pro Pro Val Leu Asp Ser Asp Gly Ser Phe Phe Leu Tyr Ser
                645                 650                 655

Lys Leu Thr Val Asp Lys Ser Arg Trp Gln Gln Gly Asn Val Phe Ser
            660                 665                 670

Cys Ser Val Met His Glu Ala Leu His Asn His Tyr Thr Gln Lys Ser
        675                 680                 685

Leu Ser Leu Ser Pro Gly Lys
    690                 695

<210> SEQ ID NO 5
<211> LENGTH: 450
<212> TYPE: PRT
<213> ORGANISM: Artificial
<220> FEATURE:
<223> OTHER INFORMATION: <EGFR> heavy chain, OA-GA201-scFab-Ak18 (+WT)

<400> SEQUENCE: 5

Gln Val Gln Leu Val Gln Ser Gly Ala Glu Val Lys Lys Pro Gly Ser
1               5                   10                  15

Ser Val Lys Val Ser Cys Lys Ala Ser Gly Phe Thr Phe Thr Asp Tyr
            20                  25                  30
```

-continued

```
Lys Ile His Trp Val Arg Gln Ala Pro Gly Gln Gly Leu Glu Trp Met
         35                  40                  45
Gly Tyr Phe Asn Pro Asn Ser Gly Tyr Ser Thr Tyr Ala Gln Lys Phe
 50                  55                  60
Gln Gly Arg Val Thr Ile Thr Ala Asp Lys Ser Thr Ser Thr Ala Tyr
 65                  70                  75                  80
Met Glu Leu Ser Ser Leu Arg Ser Glu Asp Thr Ala Val Tyr Tyr Cys
             85                  90                  95
Ala Arg Leu Ser Pro Gly Gly Tyr Tyr Val Met Asp Ala Trp Gly Gln
             100                 105                 110
Gly Thr Thr Val Thr Val Ser Ser Ala Ser Thr Lys Gly Pro Ser Val
             115                 120                 125
Phe Pro Leu Ala Pro Ser Ser Lys Ser Thr Ser Gly Gly Thr Ala Ala
 130                 135                 140
Leu Gly Cys Leu Val Lys Asp Tyr Phe Pro Glu Pro Val Thr Val Ser
145                 150                 155                 160
Trp Asn Ser Gly Ala Leu Thr Ser Gly Val His Thr Phe Pro Ala Val
                 165                 170                 175
Leu Gln Ser Ser Gly Leu Tyr Ser Leu Ser Ser Val Val Thr Val Pro
                 180                 185                 190
Ser Ser Leu Gly Thr Gln Thr Tyr Ile Cys Asn Val Asn His Lys
             195                 200                 205
Pro Ser Asn Thr Lys Val Asp Lys Lys Val Glu Pro Lys Ser Cys Asp
 210                 215                 220
Lys Thr His Thr Cys Pro Pro Cys Pro Ala Pro Glu Leu Leu Gly Gly
225                 230                 235                 240
Pro Ser Val Phe Leu Phe Pro Pro Lys Pro Lys Asp Thr Leu Met Ile
                 245                 250                 255
Ser Arg Thr Pro Glu Val Thr Cys Val Val Val Asp Val Ser His Glu
             260                 265                 270
Asp Pro Glu Val Lys Phe Asn Trp Tyr Val Asp Gly Val Glu Val His
             275                 280                 285
Asn Ala Lys Thr Lys Pro Arg Glu Glu Gln Tyr Asn Ser Thr Tyr Arg
 290                 295                 300
Val Val Ser Val Leu Thr Val Leu His Gln Asp Trp Leu Asn Gly Lys
305                 310                 315                 320
Glu Tyr Lys Cys Lys Val Ser Asn Lys Ala Leu Pro Ala Pro Ile Glu
                 325                 330                 335
Lys Thr Ile Ser Lys Ala Lys Gly Gln Pro Arg Glu Pro Gln Val Tyr
             340                 345                 350
Thr Leu Pro Pro Cys Arg Asp Glu Leu Thr Lys Asn Gln Val Ser Leu
             355                 360                 365
Trp Cys Leu Val Lys Gly Phe Tyr Pro Ser Asp Ile Ala Val Glu Trp
 370                 375                 380
Glu Ser Asn Gly Gln Pro Glu Asn Asn Tyr Lys Thr Thr Pro Pro Val
385                 390                 395                 400
Leu Asp Ser Asp Gly Ser Phe Phe Leu Tyr Ser Lys Leu Thr Val Asp
                 405                 410                 415
Lys Ser Arg Trp Gln Gln Gly Asn Val Phe Ser Cys Ser Val Met His
                 420                 425                 430
```

Glu Ala Leu His Asn His Tyr Thr Gln Lys Ser Leu Ser Leu Ser Pro
            435                 440                 445

Gly Lys
    450

<210> SEQ ID NO 6
<211> LENGTH: 213
<212> TYPE: PRT
<213> ORGANISM: Artificial
<220> FEATURE:
<223> OTHER INFORMATION: <EGFR> light chain, OA-GA201-scFab-Ak18 (+WT)

<400> SEQUENCE: 6

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Gly Ile Asn Asn Tyr
            20                  25                  30

Leu Asn Trp Tyr Gln Gln Lys Pro Gly Lys Ala Pro Lys Arg Leu Ile
        35                  40                  45

Tyr Asn Thr Asn Asn Leu Gln Thr Gly Val Pro Ser Arg Phe Ser Gly
    50                  55                  60

Ser Gly Ser Gly Thr Glu Phe Thr Leu Thr Ile Ser Ser Leu Gln Pro
65                  70                  75                  80

Glu Asp Phe Ala Thr Tyr Tyr Cys Leu Gln His Asn Ser Phe Pro Thr
                85                  90                  95

Phe Gly Gln Gly Thr Lys Leu Glu Ile Lys Arg Thr Val Ala Ala Pro
            100                 105                 110

Ser Val Phe Ile Phe Pro Pro Ser Asp Glu Gln Leu Lys Ser Gly Thr
        115                 120                 125

Ala Ser Val Val Cys Leu Leu Asn Asn Phe Tyr Pro Arg Glu Ala Lys
    130                 135                 140

Val Gln Trp Lys Val Asp Asn Ala Leu Gln Ser Gly Asn Ser Gln Glu
145                 150                 155                 160

Ser Val Thr Glu Gln Asp Ser Lys Asp Ser Thr Tyr Ser Leu Ser Ser
                165                 170                 175

Thr Leu Thr Leu Ser Lys Ala Asp Tyr Glu Lys His Lys Val Tyr Ala
            180                 185                 190

Cys Glu Val Thr His Gln Gly Leu Ser Ser Pro Val Thr Lys Ser Phe
        195                 200                 205

Asn Arg Gly Glu Cys
    210

<210> SEQ ID NO 7
<211> LENGTH: 695
<212> TYPE: PRT
<213> ORGANISM: Artificial
<220> FEATURE:
<223> OTHER INFORMATION: <IGF-1R> peptide connected heavy and light
      chain with disulfide stabilization VH 44 /VL100-
      OA-GA201-scFab-Ak18

<400> SEQUENCE: 7

Glu Ile Val Leu Thr Gln Ser Pro Ala Thr Leu Ser Leu Ser Pro Gly
1               5                   10                  15

Glu Arg Ala Thr Leu Ser Cys Arg Ala Ser Gln Ser Val Ser Ser Tyr
            20                  25                  30

Leu Ala Trp Tyr Gln Gln Lys Pro Gly Gln Ala Pro Arg Leu Leu Ile
        35                  40                  45

```
Tyr Asp Ala Ser Lys Arg Ala Thr Gly Ile Pro Ala Arg Phe Ser Gly
 50                  55                  60

Ser Gly Ser Gly Thr Asp Phe Thr Leu Thr Ile Ser Ser Leu Glu Pro
 65                  70                  75                  80

Glu Asp Phe Ala Val Tyr Tyr Cys Gln Gln Arg Ser Lys Trp Pro Pro
                 85                  90                  95

Trp Thr Phe Gly Cys Gly Thr Lys Val Glu Ser Lys Arg Thr Val Ala
                100                 105                 110

Ala Pro Ser Val Phe Ile Phe Pro Pro Ser Asp Glu Gln Leu Lys Ser
                115                 120                 125

Gly Thr Ala Ser Val Val Cys Leu Leu Asn Asn Phe Tyr Pro Arg Glu
130                 135                 140

Ala Lys Val Gln Trp Lys Val Asp Asn Ala Leu Gln Ser Gly Asn Ser
145                 150                 155                 160

Gln Glu Ser Val Thr Glu Gln Asp Ser Lys Asp Ser Thr Tyr Ser Leu
                165                 170                 175

Ser Ser Thr Leu Thr Leu Ser Lys Ala Asp Tyr Glu Lys His Lys Val
                180                 185                 190

Tyr Ala Cys Glu Val Thr His Gln Gly Leu Ser Ser Pro Val Thr Lys
                195                 200                 205

Ser Phe Asn Arg Gly Glu Cys Gly Gly Gly Gly Ser Gly Gly Gly Gly
                210                 215                 220

Ser Gly Gly Gly Gly Ser Gly Gly Gly Gly Ser Gly Gly Gly Gly Ser
225                 230                 235                 240

Gly Gly Gly Gly Ser Gly Gly Gln Val Glu Leu Val Glu Ser Gly Gly
                245                 250                 255

Gly Val Val Gln Pro Gly Arg Ser Gln Arg Leu Ser Cys Ala Ala Ser
                260                 265                 270

Gly Phe Thr Phe Ser Ser Tyr Gly Met His Trp Val Arg Gln Ala Pro
                275                 280                 285

Gly Lys Cys Leu Glu Trp Val Ala Ile Ile Trp Phe Asp Gly Ser Ser
                290                 295                 300

Thr Tyr Tyr Ala Asp Ser Val Arg Gly Arg Phe Thr Ile Ser Arg Asp
305                 310                 315                 320

Asn Ser Lys Asn Thr Leu Tyr Leu Gln Met Asn Ser Leu Arg Ala Glu
                325                 330                 335

Asp Thr Ala Val Tyr Phe Cys Ala Arg Glu Leu Gly Arg Arg Tyr Phe
                340                 345                 350

Asp Leu Trp Gly Arg Gly Thr Leu Val Ser Val Ser Ser Ala Ser Thr
                355                 360                 365

Lys Gly Pro Ser Val Phe Pro Leu Ala Pro Ser Ser Lys Ser Thr Ser
                370                 375                 380

Gly Gly Thr Ala Ala Leu Gly Cys Leu Val Lys Asp Tyr Phe Pro Glu
385                 390                 395                 400

Pro Val Thr Val Ser Trp Asn Ser Gly Ala Leu Thr Ser Gly Val His
                405                 410                 415

Thr Phe Pro Ala Val Leu Gln Ser Ser Gly Leu Tyr Ser Leu Ser Ser
                420                 425                 430

Val Val Thr Val Pro Ser Ser Ser Leu Gly Thr Gln Thr Tyr Ile Cys
                435                 440                 445

Asn Val Asn His Lys Pro Ser Asn Thr Lys Val Asp Lys Lys Val Glu
                450                 455                 460
```

-continued

```
Pro Lys Ser Cys Asp Lys Thr His Thr Cys Pro Cys Pro Ala Pro
465                 470                 475                 480

Glu Leu Leu Gly Gly Pro Ser Val Phe Leu Phe Pro Pro Lys Pro Lys
                485                 490                 495

Asp Thr Leu Met Ile Ser Arg Thr Pro Glu Val Thr Cys Val Val Val
            500                 505                 510

Asp Val Ser His Glu Asp Pro Glu Val Lys Phe Asn Trp Tyr Val Asp
        515                 520                 525

Gly Val Glu Val His Asn Ala Lys Thr Lys Pro Arg Glu Glu Gln Tyr
    530                 535                 540

Asn Ser Thr Tyr Arg Val Val Ser Val Leu Thr Val Leu His Gln Asp
545                 550                 555                 560

Trp Leu Asn Gly Lys Glu Tyr Lys Cys Lys Val Ser Asn Lys Ala Leu
                565                 570                 575

Pro Ala Pro Ile Glu Lys Thr Ile Ser Lys Ala Lys Gly Gln Pro Arg
            580                 585                 590

Glu Pro Gln Val Cys Thr Leu Pro Pro Ser Arg Asp Glu Leu Thr Lys
        595                 600                 605

Asn Gln Val Ser Leu Ser Cys Ala Val Lys Gly Phe Tyr Pro Ser Asp
    610                 615                 620

Ile Ala Val Glu Trp Glu Ser Asn Gly Gln Pro Glu Asn Asn Tyr Lys
625                 630                 635                 640

Thr Thr Pro Pro Val Leu Asp Ser Asp Gly Ser Phe Phe Leu Val Ser
                645                 650                 655

Lys Leu Thr Val Asp Lys Ser Arg Trp Gln Gln Gly Asn Val Phe Ser
            660                 665                 670

Cys Ser Val Met His Glu Ala Leu His Asn His Tyr Thr Gln Lys Ser
        675                 680                 685

Leu Ser Leu Ser Pro Gly Lys
    690                 695

<210> SEQ ID NO 8
<211> LENGTH: 695
<212> TYPE: PRT
<213> ORGANISM: Artificial
<220> FEATURE:
<223> OTHER INFORMATION: <IGF-1R> peptide connected heavy and light
      chain of OA-GA201-scFab-Ak18_WT

<400> SEQUENCE: 8

Glu Ile Val Leu Thr Gln Ser Pro Ala Thr Leu Ser Leu Ser Pro Gly
1               5                   10                  15

Glu Arg Ala Thr Leu Ser Cys Arg Ala Ser Gln Ser Val Ser Ser Tyr
            20                  25                  30

Leu Ala Trp Tyr Gln Gln Lys Pro Gly Gln Ala Pro Arg Leu Leu Ile
        35                  40                  45

Tyr Asp Ala Ser Lys Arg Ala Thr Gly Ile Pro Ala Arg Phe Ser Gly
    50                  55                  60

Ser Gly Ser Gly Thr Asp Phe Thr Leu Thr Ile Ser Ser Leu Glu Pro
65                  70                  75                  80

Glu Asp Phe Ala Val Tyr Tyr Cys Gln Gln Arg Ser Lys Trp Pro Pro
                85                  90                  95

Trp Thr Phe Gly Gln Gly Thr Lys Val Glu Ser Lys Arg Thr Val Ala
            100                 105                 110

Ala Pro Ser Val Phe Ile Phe Pro Pro Ser Asp Glu Gln Leu Lys Ser
        115                 120                 125
```

-continued

```
Gly Thr Ala Ser Val Val Cys Leu Leu Asn Asn Phe Tyr Pro Arg Glu
130                 135                 140

Ala Lys Val Gln Trp Lys Val Asp Asn Ala Leu Gln Ser Gly Asn Ser
145                 150                 155                 160

Gln Glu Ser Val Thr Glu Gln Asp Ser Lys Asp Ser Thr Tyr Ser Leu
                165                 170                 175

Ser Ser Thr Leu Thr Leu Ser Lys Ala Asp Tyr Glu Lys His Lys Val
            180                 185                 190

Tyr Ala Cys Glu Val Thr His Gln Gly Leu Ser Ser Pro Val Thr Lys
        195                 200                 205

Ser Phe Asn Arg Gly Glu Cys Gly Gly Gly Ser Gly Gly Gly Gly
210                 215                 220

Ser Gly Gly Gly Ser Gly Gly Gly Ser Gly Gly Gly Ser
225                 230                 235                 240

Gly Gly Gly Gly Ser Gly Gly Gln Val Glu Leu Val Glu Ser Gly Gly
                245                 250                 255

Gly Val Val Gln Pro Gly Arg Ser Gln Arg Leu Ser Cys Ala Ala Ser
            260                 265                 270

Gly Phe Thr Phe Ser Ser Tyr Gly Met His Trp Val Arg Gln Ala Pro
        275                 280                 285

Gly Lys Gly Leu Glu Trp Val Ala Ile Ile Trp Phe Asp Gly Ser Ser
290                 295                 300

Thr Tyr Tyr Ala Asp Ser Val Arg Gly Arg Phe Thr Ile Ser Arg Asp
305                 310                 315                 320

Asn Ser Lys Asn Thr Leu Tyr Leu Gln Met Asn Ser Leu Arg Ala Glu
                325                 330                 335

Asp Thr Ala Val Tyr Phe Cys Ala Arg Glu Leu Gly Arg Arg Tyr Phe
            340                 345                 350

Asp Leu Trp Gly Arg Gly Thr Leu Val Ser Val Ser Ser Ala Ser Thr
        355                 360                 365

Lys Gly Pro Ser Val Phe Pro Leu Ala Pro Ser Ser Lys Ser Thr Ser
370                 375                 380

Gly Gly Thr Ala Ala Leu Gly Cys Leu Val Lys Asp Tyr Phe Pro Glu
385                 390                 395                 400

Pro Val Thr Val Ser Trp Asn Ser Gly Ala Leu Thr Ser Gly Val His
                405                 410                 415

Thr Phe Pro Ala Val Leu Gln Ser Ser Gly Leu Tyr Ser Leu Ser Ser
            420                 425                 430

Val Val Thr Val Pro Ser Ser Ser Leu Gly Thr Gln Thr Tyr Ile Cys
        435                 440                 445

Asn Val Asn His Lys Pro Ser Asn Thr Lys Val Asp Lys Lys Val Glu
450                 455                 460

Pro Lys Ser Cys Asp Lys Thr His Thr Cys Pro Pro Cys Pro Ala Pro
465                 470                 475                 480

Glu Leu Leu Gly Gly Pro Ser Val Phe Leu Phe Pro Pro Lys Pro Lys
                485                 490                 495

Asp Thr Leu Met Ile Ser Arg Thr Pro Glu Val Thr Cys Val Val Val
            500                 505                 510

Asp Val Ser His Glu Asp Pro Glu Val Lys Phe Asn Trp Tyr Val Asp
        515                 520                 525

Gly Val Glu Val His Asn Ala Lys Thr Lys Pro Arg Glu Glu Gln Tyr
530                 535                 540
```

```
Asn Ser Thr Tyr Arg Val Val Ser Val Leu Thr Val Leu His Gln Asp
545                 550                 555                 560

Trp Leu Asn Gly Lys Glu Tyr Lys Cys Lys Val Ser Asn Lys Ala Leu
                565                 570                 575

Pro Ala Pro Ile Glu Lys Thr Ile Ser Lys Ala Lys Gly Gln Pro Arg
            580                 585                 590

Glu Pro Gln Val Cys Thr Leu Pro Pro Ser Arg Asp Glu Leu Thr Lys
        595                 600                 605

Asn Gln Val Ser Leu Ser Cys Ala Val Lys Gly Phe Tyr Pro Ser Asp
    610                 615                 620

Ile Ala Val Glu Trp Glu Ser Asn Gly Gln Pro Glu Asn Asn Tyr Lys
625                 630                 635                 640

Thr Thr Pro Pro Val Leu Asp Ser Asp Gly Ser Phe Phe Leu Val Ser
                645                 650                 655

Lys Leu Thr Val Asp Lys Ser Arg Trp Gln Gln Gly Asn Val Phe Ser
            660                 665                 670

Cys Ser Val Met His Glu Ala Leu His Asn His Tyr Thr Gln Lys Ser
        675                 680                 685

Leu Ser Leu Ser Pro Gly Lys
    690                 695

<210> SEQ ID NO 9
<211> LENGTH: 453
<212> TYPE: PRT
<213> ORGANISM: Artificial
<220> FEATURE:
<223> OTHER INFORMATION: <VEGF> heavy chain, Ang2-VEGF
      OA-Ava-N-scFabLC06 (+SS)

<400> SEQUENCE: 9

Glu Val Gln Leu Val Glu Ser Gly Gly Gly Leu Val Gln Pro Gly Gly
1               5                   10                  15

Ser Leu Arg Leu Ser Cys Ala Ala Ser Gly Tyr Thr Phe Thr Asn Tyr
            20                  25                  30

Gly Met Asn Trp Val Arg Gln Ala Pro Gly Lys Gly Leu Glu Trp Val
        35                  40                  45

Gly Trp Ile Asn Thr Tyr Thr Gly Glu Pro Thr Tyr Ala Ala Asp Phe
    50                  55                  60

Lys Arg Arg Phe Thr Phe Ser Leu Asp Thr Ser Lys Ser Thr Ala Tyr
65                  70                  75                  80

Leu Gln Met Asn Ser Leu Arg Ala Glu Asp Thr Ala Val Tyr Tyr Cys
            85                  90                  95

Ala Lys Tyr Pro His Tyr Tyr Gly Ser Ser His Trp Tyr Phe Asp Val
        100                 105                 110

Trp Gly Gln Gly Thr Leu Val Thr Val Ser Ser Ala Ser Thr Lys Gly
    115                 120                 125

Pro Ser Val Phe Pro Leu Ala Pro Ser Ser Lys Ser Thr Ser Gly Gly
130                 135                 140

Thr Ala Ala Leu Gly Cys Leu Val Lys Asp Tyr Phe Pro Glu Pro Val
145                 150                 155                 160

Thr Val Ser Trp Asn Ser Gly Ala Leu Thr Ser Gly Val His Thr Phe
            165                 170                 175

Pro Ala Val Leu Gln Ser Ser Gly Leu Tyr Ser Leu Ser Ser Val Val
        180                 185                 190

Thr Val Pro Ser Ser Ser Leu Gly Thr Gln Thr Tyr Ile Cys Asn Val
    195                 200                 205
```

```
Asn His Lys Pro Ser Asn Thr Lys Val Asp Lys Lys Val Glu Pro Lys
    210                 215                 220

Ser Cys Asp Lys Thr His Thr Cys Pro Pro Cys Pro Ala Pro Glu Leu
225                 230                 235                 240

Leu Gly Gly Pro Ser Val Phe Leu Phe Pro Pro Lys Pro Lys Asp Thr
                245                 250                 255

Leu Met Ile Ser Arg Thr Pro Glu Val Thr Cys Val Val Val Asp Val
                260                 265                 270

Ser His Glu Asp Pro Glu Val Lys Phe Asn Trp Tyr Val Asp Gly Val
            275                 280                 285

Glu Val His Asn Ala Lys Thr Lys Pro Arg Glu Glu Gln Tyr Asn Ser
        290                 295                 300

Thr Tyr Arg Val Val Ser Val Leu Thr Val Leu His Gln Asp Trp Leu
305                 310                 315                 320

Asn Gly Lys Glu Tyr Lys Cys Lys Val Ser Asn Lys Ala Leu Pro Ala
                325                 330                 335

Pro Ile Glu Lys Thr Ile Ser Lys Ala Lys Gly Gln Pro Arg Glu Pro
                340                 345                 350

Gln Val Cys Thr Leu Pro Pro Ser Arg Asp Glu Leu Thr Lys Asn Gln
            355                 360                 365

Val Ser Leu Ser Cys Ala Val Lys Gly Phe Tyr Pro Ser Asp Ile Ala
370                 375                 380

Val Glu Trp Glu Ser Asn Gly Gln Pro Glu Asn Asn Tyr Lys Thr Thr
385                 390                 395                 400

Pro Pro Val Leu Asp Ser Asp Gly Ser Phe Phe Leu Val Ser Lys Leu
                405                 410                 415

Thr Val Asp Lys Ser Arg Trp Gln Gln Gly Asn Val Phe Ser Cys Ser
                420                 425                 430

Val Met His Glu Ala Leu His Asn His Tyr Thr Gln Lys Ser Leu Ser
            435                 440                 445

Leu Ser Pro Gly Lys
    450

<210> SEQ ID NO 10
<211> LENGTH: 214
<212> TYPE: PRT
<213> ORGANISM: Artificial
<220> FEATURE:
<223> OTHER INFORMATION: <VEGF> light chain, Ang2-VEGF
      OA-Ava-N-scFabLC06 (+SS)

<400> SEQUENCE: 10

Asp Ile Gln Met Thr Gln Ser Pro Ser Ser Leu Ser Ala Ser Val Gly
1               5                   10                  15

Asp Arg Val Thr Ile Thr Cys Ser Ala Ser Gln Asp Ile Ser Asn Tyr
            20                  25                  30

Leu Asn Trp Tyr Gln Gln Lys Pro Gly Lys Ala Pro Lys Val Leu Ile
        35                  40                  45

Tyr Phe Thr Ser Ser Leu His Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Tyr Ser Thr Val Pro Trp
                85                  90                  95

Thr Phe Gly Gln Gly Thr Lys Val Glu Ile Lys Arg Thr Val Ala Ala
            100                 105                 110
```

```
Pro Ser Val Phe Ile Phe Pro Pro Ser Asp Glu Gln Leu Lys Ser Gly
            115                 120                 125

Thr Ala Ser Val Val Cys Leu Leu Asn Asn Phe Tyr Pro Arg Glu Ala
    130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys
    210

<210> SEQ ID NO 11
<211> LENGTH: 706
<212> TYPE: PRT
<213> ORGANISM: Artificial
<220> FEATURE:
<223> OTHER INFORMATION: <ANG-2> peptide connected heavy and light chain
      with disulfide stabilization VH 44 /VL100 of Ang2-VEGF
      OA-Ava-N-scFabLC06SS

<400> SEQUENCE: 11

Gln Pro Gly Leu Thr Gln Pro Pro Ser Val Ser Val Ala Pro Gly Gln
1               5                   10                  15

Thr Ala Arg Ile Thr Cys Gly Gly Asn Asn Ile Gly Ser Lys Ser Val
            20                  25                  30

His Trp Tyr Gln Gln Lys Pro Gly Gln Ala Pro Val Leu Val Val Tyr
        35                  40                  45

Asp Asp Ser Asp Arg Pro Ser Gly Ile Pro Glu Arg Phe Ser Gly Ser
    50                  55                  60

Asn Ser Gly Asn Thr Ala Thr Leu Thr Ile Ser Arg Val Glu Ala Gly
65                  70                  75                  80

Asp Glu Ala Asp Tyr Tyr Cys Gln Val Trp Asp Ser Ser Ser Asp His
                85                  90                  95

Tyr Val Phe Gly Cys Gly Thr Lys Val Thr Val Leu Arg Thr Val Ala
            100                 105                 110

Ala Pro Ser Val Phe Ile Phe Pro Pro Ser Asp Glu Gln Leu Lys Ser
        115                 120                 125

Gly Thr Ala Ser Val Val Cys Leu Leu Asn Asn Phe Tyr Pro Arg Glu
    130                 135                 140

Ala Lys Val Gln Trp Lys Val Asp Asn Ala Leu Gln Ser Gly Asn Ser
145                 150                 155                 160

Gln Glu Ser Val Thr Glu Gln Asp Ser Lys Asp Ser Thr Tyr Ser Leu
                165                 170                 175

Ser Ser Thr Leu Thr Leu Ser Lys Ala Asp Tyr Glu Lys His Lys Val
            180                 185                 190

Tyr Ala Cys Glu Val Thr His Gln Gly Leu Ser Ser Pro Val Thr Lys
        195                 200                 205

Ser Phe Asn Arg Gly Glu Cys Gly Gly Gly Gly Ser Gly Gly Gly Gly
    210                 215                 220

Ser Gly Gly Gly Gly Ser Gly Gly Gly Gly Ser Gly Gly Gly Gly Ser
225                 230                 235                 240
```

-continued

```
Gly Gly Gly Gly Ser Gly Gln Val Gln Leu Val Glu Ser Gly Ala
            245                 250                 255
Glu Val Lys Lys Pro Gly Ala Ser Val Lys Val Ser Cys Lys Ala Ser
        260                 265                 270
Gly Tyr Thr Phe Thr Gly Tyr Tyr Met His Trp Val Arg Gln Ala Pro
        275                 280                 285
Gly Gln Cys Leu Glu Trp Met Gly Trp Ile Asn Pro Asn Ser Gly Gly
        290                 295                 300
Thr Asn Tyr Ala Gln Lys Phe Gln Gly Arg Val Thr Met Thr Arg Asp
305                 310                 315                 320
Thr Ser Ile Ser Thr Ala Tyr Met Glu Leu Ser Arg Leu Arg Ser Asp
                325                 330                 335
Asp Thr Ala Val Tyr Tyr Cys Ala Arg Ser Pro Asn Pro Tyr Tyr Tyr
                340                 345                 350
Asp Ser Ser Gly Tyr Tyr Pro Gly Ala Phe Asp Ile Trp Gly Gln
            355                 360                 365
Gly Thr Met Val Thr Val Ser Ser Ala Ser Thr Lys Gly Pro Ser Val
    370                 375                 380
Phe Pro Leu Ala Pro Ser Ser Lys Ser Thr Ser Gly Gly Thr Ala Ala
385                 390                 395                 400
Leu Gly Cys Leu Val Lys Asp Tyr Phe Pro Glu Pro Val Thr Val Ser
                405                 410                 415
Trp Asn Ser Gly Ala Leu Thr Ser Gly Val His Thr Phe Pro Ala Val
                420                 425                 430
Leu Gln Ser Ser Gly Leu Tyr Ser Leu Ser Ser Val Val Thr Val Pro
            435                 440                 445
Ser Ser Ser Leu Gly Thr Gln Thr Tyr Ile Cys Asn Val Asn His Lys
    450                 455                 460
Pro Ser Asn Thr Lys Val Asp Lys Val Glu Pro Lys Ser Cys Asp
465                 470                 475                 480
Lys Thr His Thr Cys Pro Pro Cys Pro Ala Pro Glu Leu Leu Gly Gly
                485                 490                 495
Pro Ser Val Phe Leu Phe Pro Pro Lys Pro Lys Asp Thr Leu Met Ile
            500                 505                 510
Ser Arg Thr Pro Glu Val Thr Cys Val Val Val Asp Val Ser His Glu
    515                 520                 525
Asp Pro Glu Val Lys Phe Asn Trp Tyr Val Asp Gly Val Glu Val His
            530                 535                 540
Asn Ala Lys Thr Lys Pro Arg Glu Glu Gln Tyr Asn Ser Thr Tyr Arg
545                 550                 555                 560
Val Val Ser Val Leu Thr Val Leu His Gln Asp Trp Leu Asn Gly Lys
                565                 570                 575
Glu Tyr Lys Cys Lys Val Ser Asn Lys Ala Leu Pro Ala Pro Ile Glu
                580                 585                 590
Lys Thr Ile Ser Lys Ala Lys Gly Gln Pro Arg Glu Pro Gln Val Tyr
            595                 600                 605
Thr Leu Pro Pro Cys Arg Asp Glu Leu Thr Lys Asn Gln Val Ser Leu
    610                 615                 620
Trp Cys Leu Val Lys Gly Phe Tyr Pro Ser Asp Ile Ala Val Glu Trp
625                 630                 635                 640
Glu Ser Asn Gly Gln Pro Glu Asn Asn Tyr Lys Thr Thr Pro Pro Val
                645                 650                 655
```

-continued

```
Leu Asp Ser Asp Gly Ser Phe Phe Leu Tyr Ser Lys Leu Thr Val Asp
            660                 665                 670

Lys Ser Arg Trp Gln Gln Gly Asn Val Phe Ser Cys Ser Val Met His
        675                 680                 685

Glu Ala Leu His Asn His Tyr Thr Gln Lys Ser Leu Ser Leu Ser Pro
    690                 695                 700

Gly Lys
705

<210> SEQ ID NO 12
<211> LENGTH: 706
<212> TYPE: PRT
<213> ORGANISM: Artificial
<220> FEATURE:
<223> OTHER INFORMATION: <ANG-2> peptide connected heavy and light chain
      of Ang2-VEGF OA-Ava-N-scFabLC06

<400> SEQUENCE: 12

Gln Pro Gly Leu Thr Gln Pro Pro Ser Val Ser Val Ala Pro Gly Gln
1               5                   10                  15

Thr Ala Arg Ile Thr Cys Gly Gly Asn Asn Ile Gly Ser Lys Ser Val
            20                  25                  30

His Trp Tyr Gln Gln Lys Pro Gly Gln Ala Pro Val Leu Val Val Tyr
        35                  40                  45

Asp Asp Ser Asp Arg Pro Ser Gly Ile Pro Glu Arg Phe Ser Gly Ser
    50                  55                  60

Asn Ser Gly Asn Thr Ala Thr Leu Thr Ile Ser Arg Val Glu Ala Gly
65                  70                  75                  80

Asp Glu Ala Asp Tyr Tyr Cys Gln Val Trp Asp Ser Ser Ser Asp His
                85                  90                  95

Tyr Val Phe Gly Thr Gly Thr Lys Val Thr Val Leu Arg Thr Val Ala
            100                 105                 110

Ala Pro Ser Val Phe Ile Phe Pro Pro Ser Asp Glu Gln Leu Lys Ser
        115                 120                 125

Gly Thr Ala Ser Val Val Cys Leu Leu Asn Asn Phe Tyr Pro Arg Glu
    130                 135                 140

Ala Lys Val Gln Trp Lys Val Asp Asn Ala Leu Gln Ser Gly Asn Ser
145                 150                 155                 160

Gln Glu Ser Val Thr Glu Gln Asp Ser Lys Asp Ser Thr Tyr Ser Leu
                165                 170                 175

Ser Ser Thr Leu Thr Leu Ser Lys Ala Asp Tyr Glu Lys His Lys Val
            180                 185                 190

Tyr Ala Cys Glu Val Thr His Gln Gly Leu Ser Ser Pro Val Thr Lys
        195                 200                 205

Ser Phe Asn Arg Gly Glu Cys Gly Gly Gly Gly Ser Gly Gly Gly Gly
    210                 215                 220

Ser Gly Gly Gly Gly Ser Gly Gly Gly Gly Ser Gly Gly Gly Gly Ser
225                 230                 235                 240

Gly Gly Gly Gly Ser Gly Gly Gln Val Gln Leu Val Glu Ser Gly Ala
                245                 250                 255

Glu Val Lys Lys Pro Gly Ala Ser Val Lys Val Ser Cys Lys Ala Ser
            260                 265                 270

Gly Tyr Thr Phe Thr Gly Tyr Tyr Met His Trp Val Arg Gln Ala Pro
        275                 280                 285

Gly Gln Gly Leu Glu Trp Met Gly Trp Ile Asn Pro Asn Ser Gly Gly
    290                 295                 300
```

-continued

```
Thr Asn Tyr Ala Gln Lys Phe Gln Gly Arg Val Thr Met Thr Arg Asp
305                 310                 315                 320
Thr Ser Ile Ser Thr Ala Tyr Met Glu Leu Ser Arg Leu Arg Ser Asp
            325                 330                 335
Asp Thr Ala Val Tyr Tyr Cys Ala Arg Ser Pro Asn Pro Tyr Tyr Tyr
                340                 345                 350
Asp Ser Ser Gly Tyr Tyr Pro Gly Ala Phe Asp Ile Trp Gly Gln Gly
            355                 360                 365
Gly Thr Met Val Thr Val Ser Ser Ala Ser Thr Lys Gly Pro Ser Val
    370                 375                 380
Phe Pro Leu Ala Pro Ser Ser Lys Ser Thr Ser Gly Gly Thr Ala Ala
385                 390                 395                 400
Leu Gly Cys Leu Val Lys Asp Tyr Phe Pro Glu Pro Val Thr Val Ser
                405                 410                 415
Trp Asn Ser Gly Ala Leu Thr Ser Gly Val His Thr Phe Pro Ala Val
            420                 425                 430
Leu Gln Ser Ser Gly Leu Tyr Ser Leu Ser Ser Val Val Thr Val Pro
        435                 440                 445
Ser Ser Ser Leu Gly Thr Gln Thr Tyr Ile Cys Asn Val Asn His Lys
450                 455                 460
Pro Ser Asn Thr Lys Val Asp Lys Lys Val Glu Pro Lys Ser Cys Asp
465                 470                 475                 480
Lys Thr His Thr Cys Pro Pro Cys Pro Ala Pro Glu Leu Leu Gly Gly
                485                 490                 495
Pro Ser Val Phe Leu Phe Pro Pro Lys Pro Lys Asp Thr Leu Met Ile
            500                 505                 510
Ser Arg Thr Pro Glu Val Thr Cys Val Val Val Asp Val Ser His Glu
        515                 520                 525
Asp Pro Glu Val Lys Phe Asn Trp Tyr Val Asp Gly Val Glu Val His
530                 535                 540
Asn Ala Lys Thr Lys Pro Arg Glu Glu Gln Tyr Asn Ser Thr Tyr Arg
545                 550                 555                 560
Val Val Ser Val Leu Thr Val Leu His Gln Asp Trp Leu Asn Gly Lys
                565                 570                 575
Glu Tyr Lys Cys Lys Val Ser Asn Lys Ala Leu Pro Ala Pro Ile Glu
            580                 585                 590
Lys Thr Ile Ser Lys Ala Lys Gly Gln Pro Arg Glu Pro Gln Val Tyr
        595                 600                 605
Thr Leu Pro Pro Cys Arg Asp Glu Leu Thr Lys Asn Gln Val Ser Leu
610                 615                 620
Trp Cys Leu Val Lys Gly Phe Tyr Pro Ser Asp Ile Ala Val Glu Trp
625                 630                 635                 640
Glu Ser Asn Gly Gln Pro Glu Asn Asn Tyr Lys Thr Thr Pro Pro Val
                645                 650                 655
Leu Asp Ser Asp Gly Ser Phe Phe Leu Tyr Ser Lys Leu Thr Val Asp
            660                 665                 670
Lys Ser Arg Trp Gln Gln Gly Asn Val Phe Ser Cys Ser Val Met His
        675                 680                 685
Glu Ala Leu His Asn His Tyr Thr Gln Lys Ser Leu Ser Leu Ser Pro
690                 695                 700
Gly Lys
705
```

<210> SEQ ID NO 13
<211> LENGTH: 1210
<212> TYPE: PRT
<213> ORGANISM: Homo sapiens

<400> SEQUENCE: 13

```
Met Arg Pro Ser Gly Thr Ala Gly Ala Ala Leu Leu Ala Leu Leu Ala
1               5                   10                  15

Ala Leu Cys Pro Ala Ser Arg Ala Leu Glu Glu Lys Lys Val Cys Gln
            20                  25                  30

Gly Thr Ser Asn Lys Leu Thr Gln Leu Gly Thr Phe Glu Asp His Phe
        35                  40                  45

Leu Ser Leu Gln Arg Met Phe Asn Asn Cys Glu Val Val Leu Gly Asn
    50                  55                  60

Leu Glu Ile Thr Tyr Val Gln Arg Asn Tyr Asp Leu Ser Phe Leu Lys
65                  70                  75                  80

Thr Ile Gln Glu Val Ala Gly Tyr Val Leu Ile Ala Leu Asn Thr Val
                85                  90                  95

Glu Arg Ile Pro Leu Glu Asn Leu Gln Ile Ile Arg Gly Asn Met Tyr
            100                 105                 110

Tyr Glu Asn Ser Tyr Ala Leu Ala Val Leu Ser Asn Tyr Asp Ala Asn
        115                 120                 125

Lys Thr Gly Leu Lys Glu Leu Pro Met Arg Asn Leu Gln Glu Ile Leu
    130                 135                 140

His Gly Ala Val Arg Phe Ser Asn Asn Pro Ala Leu Cys Asn Val Glu
145                 150                 155                 160

Ser Ile Gln Trp Arg Asp Ile Val Ser Ser Asp Phe Leu Ser Asn Met
                165                 170                 175

Ser Met Asp Phe Gln Asn His Leu Gly Ser Cys Gln Lys Cys Asp Pro
            180                 185                 190

Ser Cys Pro Asn Gly Ser Cys Trp Gly Ala Gly Glu Glu Asn Cys Gln
        195                 200                 205

Lys Leu Thr Lys Ile Ile Cys Ala Gln Gln Cys Ser Gly Arg Cys Arg
    210                 215                 220

Gly Lys Ser Pro Ser Asp Cys Cys His Asn Gln Cys Ala Ala Gly Cys
225                 230                 235                 240

Thr Gly Pro Arg Glu Ser Asp Cys Leu Val Cys Arg Lys Phe Arg Asp
                245                 250                 255

Glu Ala Thr Cys Lys Asp Thr Cys Pro Pro Leu Met Leu Tyr Asn Pro
            260                 265                 270

Thr Thr Tyr Gln Met Asp Val Asn Pro Glu Gly Lys Tyr Ser Phe Gly
        275                 280                 285

Ala Thr Cys Val Lys Lys Cys Pro Arg Asn Tyr Val Val Thr Asp His
    290                 295                 300

Gly Ser Cys Val Arg Ala Cys Gly Ala Asp Ser Tyr Glu Met Glu Glu
305                 310                 315                 320

Asp Gly Val Arg Lys Cys Lys Lys Cys Glu Gly Pro Cys Arg Lys Val
                325                 330                 335

Cys Asn Gly Ile Gly Ile Gly Glu Phe Lys Asp Ser Leu Ser Ile Asn
            340                 345                 350

Ala Thr Asn Ile Lys His Phe Lys Asn Cys Thr Ser Ile Ser Gly Asp
        355                 360                 365

Leu His Ile Leu Pro Val Ala Phe Arg Gly Asp Ser Phe Thr His Thr
    370                 375                 380
```

```
Pro Pro Leu Asp Pro Gln Glu Leu Asp Ile Leu Lys Thr Val Lys Glu
385                 390                 395                 400

Ile Thr Gly Phe Leu Leu Ile Gln Ala Trp Pro Glu Asn Arg Thr Asp
            405                 410                 415

Leu His Ala Phe Glu Asn Leu Glu Ile Ile Arg Gly Arg Thr Lys Gln
            420                 425                 430

His Gly Gln Phe Ser Leu Ala Val Val Ser Leu Asn Ile Thr Ser Leu
            435                 440                 445

Gly Leu Arg Ser Leu Lys Glu Ile Ser Asp Gly Asp Val Ile Ile Ser
        450                 455                 460

Gly Asn Lys Asn Leu Cys Tyr Ala Asn Thr Ile Asn Trp Lys Lys Leu
465                 470                 475                 480

Phe Gly Thr Ser Gly Gln Lys Thr Lys Ile Ile Ser Asn Arg Gly Glu
            485                 490                 495

Asn Ser Cys Lys Ala Thr Gly Gln Val Cys His Ala Leu Cys Ser Pro
            500                 505                 510

Glu Gly Cys Trp Gly Pro Glu Pro Arg Asp Cys Val Ser Cys Arg Asn
            515                 520                 525

Val Ser Arg Gly Arg Glu Cys Val Asp Lys Cys Asn Leu Leu Glu Gly
        530                 535                 540

Glu Pro Arg Glu Phe Val Glu Asn Ser Glu Cys Ile Gln Cys His Pro
545                 550                 555                 560

Glu Cys Leu Pro Gln Ala Met Asn Ile Thr Cys Thr Gly Arg Gly Pro
            565                 570                 575

Asp Asn Cys Ile Gln Cys Ala His Tyr Ile Asp Gly Pro His Cys Val
            580                 585                 590

Lys Thr Cys Pro Ala Gly Val Met Gly Glu Asn Asn Thr Leu Val Trp
            595                 600                 605

Lys Tyr Ala Asp Ala Gly His Val Cys His Leu Cys His Pro Asn Cys
            610                 615                 620

Thr Tyr Gly Cys Thr Gly Pro Gly Leu Glu Gly Cys Pro Thr Asn Gly
625                 630                 635                 640

Pro Lys Ile Pro Ser Ile Ala Thr Gly Met Val Gly Ala Leu Leu Leu
            645                 650                 655

Leu Leu Val Val Ala Leu Gly Ile Gly Leu Phe Met Arg Arg Arg His
            660                 665                 670

Ile Val Arg Lys Arg Thr Leu Arg Arg Leu Leu Gln Glu Arg Glu Leu
            675                 680                 685

Val Glu Pro Leu Thr Pro Ser Gly Glu Ala Pro Asn Gln Ala Leu Leu
        690                 695                 700

Arg Ile Leu Lys Glu Thr Glu Phe Lys Lys Ile Lys Val Leu Gly Ser
705                 710                 715                 720

Gly Ala Phe Gly Thr Val Tyr Lys Gly Leu Trp Ile Pro Glu Gly Glu
            725                 730                 735

Lys Val Lys Ile Pro Val Ala Ile Lys Glu Leu Arg Glu Ala Thr Ser
            740                 745                 750

Pro Lys Ala Asn Lys Glu Ile Leu Asp Glu Ala Tyr Val Met Ala Ser
            755                 760                 765

Val Asp Asn Pro His Val Cys Arg Leu Leu Gly Ile Cys Leu Thr Ser
        770                 775                 780

Thr Val Gln Leu Ile Thr Gln Leu Met Pro Phe Gly Cys Leu Leu Asp
785                 790                 795                 800
```

```
Tyr Val Arg Glu His Lys Asp Asn Ile Gly Ser Gln Tyr Leu Leu Asn
            805                 810                 815

Trp Cys Val Gln Ile Ala Lys Gly Met Asn Tyr Leu Glu Asp Arg Arg
            820                 825                 830

Leu Val His Arg Asp Leu Ala Ala Arg Asn Val Leu Val Lys Thr Pro
            835                 840                 845

Gln His Val Lys Ile Thr Asp Phe Gly Leu Ala Lys Leu Leu Gly Ala
            850                 855                 860

Glu Glu Lys Glu Tyr His Ala Glu Gly Gly Lys Val Pro Ile Lys Trp
865                 870                 875                 880

Met Ala Leu Glu Ser Ile Leu His Arg Ile Tyr Thr His Gln Ser Asp
            885                 890                 895

Val Trp Ser Tyr Gly Val Thr Val Trp Glu Leu Met Thr Phe Gly Ser
            900                 905                 910

Lys Pro Tyr Asp Gly Ile Pro Ala Ser Glu Ile Ser Ser Ile Leu Glu
            915                 920                 925

Lys Gly Glu Arg Leu Pro Gln Pro Pro Ile Cys Thr Ile Asp Val Tyr
            930                 935                 940

Met Ile Met Val Lys Cys Trp Met Ile Asp Ala Asp Ser Arg Pro Lys
945                 950                 955                 960

Phe Arg Glu Leu Ile Ile Glu Phe Ser Lys Met Ala Arg Asp Pro Gln
            965                 970                 975

Arg Tyr Leu Val Ile Gln Gly Asp Glu Arg Met His Leu Pro Ser Pro
            980                 985                 990

Thr Asp Ser Asn Phe Tyr Arg Ala Leu Met Asp Glu Glu Asp Met Asp
            995                 1000                1005

Asp Val Val Asp Ala Asp Glu Tyr Leu Ile Pro Gln Gln Gly Phe
            1010                1015                1020

Phe Ser Ser Pro Ser Thr Ser Arg Thr Pro Leu Leu Ser Ser Leu
            1025                1030                1035

Ser Ala Thr Ser Asn Asn Ser Thr Val Ala Cys Ile Asp Arg Asn
            1040                1045                1050

Gly Leu Gln Ser Cys Pro Ile Lys Glu Asp Ser Phe Leu Gln Arg
            1055                1060                1065

Tyr Ser Ser Asp Pro Thr Gly Ala Leu Thr Glu Asp Ser Ile Asp
            1070                1075                1080

Asp Thr Phe Leu Pro Val Pro Glu Tyr Ile Asn Gln Ser Val Pro
            1085                1090                1095

Lys Arg Pro Ala Gly Ser Val Gln Asn Pro Val Tyr His Asn Gln
            1100                1105                1110

Pro Leu Asn Pro Ala Pro Ser Arg Asp Pro His Tyr Gln Asp Pro
            1115                1120                1125

His Ser Thr Ala Val Gly Asn Pro Glu Tyr Leu Asn Thr Val Gln
            1130                1135                1140

Pro Thr Cys Val Asn Ser Thr Phe Asp Ser Pro Ala His Trp Ala
            1145                1150                1155

Gln Lys Gly Ser His Gln Ile Ser Leu Asp Asn Pro Asp Tyr Gln
            1160                1165                1170

Gln Asp Phe Phe Pro Lys Glu Ala Lys Pro Asn Gly Ile Phe Lys
            1175                1180                1185
```

-continued

Gly Ser Thr Ala Glu Asn Ala Glu Tyr Leu Arg Val Ala Pro Gln
    1190                1195                    1200

Ser Ser Glu Phe Ile Gly Ala
    1205            1210

<210> SEQ ID NO 14
<211> LENGTH: 1367
<212> TYPE: PRT
<213> ORGANISM: Homo sapiens

<400> SEQUENCE: 14

Met Lys Ser Gly Ser Gly Gly Ser Pro Thr Ser Leu Trp Gly Leu
1               5                   10                  15

Leu Phe Leu Ser Ala Ala Leu Ser Leu Trp Pro Thr Ser Gly Glu Ile
                20                  25                  30

Cys Gly Pro Gly Ile Asp Ile Arg Asn Asp Tyr Gln Gln Leu Lys Arg
            35                  40                  45

Leu Glu Asn Cys Thr Val Ile Glu Gly Tyr Leu His Ile Leu Leu Ile
    50                  55                  60

Ser Lys Ala Glu Asp Tyr Arg Ser Tyr Arg Phe Pro Lys Leu Thr Val
65                  70                  75                  80

Ile Thr Glu Tyr Leu Leu Leu Phe Arg Val Ala Gly Leu Glu Ser Leu
                85                  90                  95

Gly Asp Leu Phe Pro Asn Leu Thr Val Ile Arg Gly Trp Lys Leu Phe
            100                 105                 110

Tyr Asn Tyr Ala Leu Val Ile Phe Glu Met Thr Asn Leu Lys Asp Ile
        115                 120                 125

Gly Leu Tyr Asn Leu Arg Asn Ile Thr Arg Gly Ala Ile Arg Ile Glu
    130                 135                 140

Lys Asn Ala Asp Leu Cys Tyr Leu Ser Thr Val Asp Trp Ser Leu Ile
145                 150                 155                 160

Leu Asp Ala Val Ser Asn Asn Tyr Ile Val Gly Asn Lys Pro Pro Lys
                165                 170                 175

Glu Cys Gly Asp Leu Cys Pro Gly Thr Met Glu Glu Lys Pro Met Cys
            180                 185                 190

Glu Lys Thr Thr Ile Asn Asn Glu Tyr Asn Tyr Arg Cys Trp Thr Thr
        195                 200                 205

Asn Arg Cys Gln Lys Met Cys Pro Ser Thr Cys Gly Lys Arg Ala Cys
    210                 215                 220

Thr Glu Asn Asn Glu Cys Cys His Pro Glu Cys Leu Gly Ser Cys Ser
225                 230                 235                 240

Ala Pro Asp Asn Asp Thr Ala Cys Val Ala Cys Arg His Tyr Tyr Tyr
                245                 250                 255

Ala Gly Val Cys Val Pro Ala Cys Pro Pro Asn Thr Tyr Arg Phe Glu
            260                 265                 270

Gly Trp Arg Cys Val Asp Arg Asp Phe Cys Ala Asn Ile Leu Ser Ala
        275                 280                 285

Glu Ser Ser Asp Ser Glu Gly Phe Val Ile His Asp Gly Glu Cys Met
    290                 295                 300

Gln Glu Cys Pro Ser Gly Phe Ile Arg Asn Gly Ser Gln Ser Met Tyr
305                 310                 315                 320

Cys Ile Pro Cys Glu Gly Pro Cys Pro Lys Val Cys Glu Glu Glu Lys
                325                 330                 335

Lys Thr Lys Thr Ile Asp Ser Val Thr Ser Ala Gln Met Leu Gln Gly
            340                 345                 350

```
Cys Thr Ile Phe Lys Gly Asn Leu Ile Asn Ile Arg Gly Asn
            355                 360                 365
Asn Ile Ala Ser Glu Leu Glu Asn Phe Met Gly Leu Ile Glu Val Val
370                 375                 380
Thr Gly Tyr Val Lys Ile Arg His Ser His Ala Leu Val Ser Leu Ser
385                 390                 395                 400
Phe Leu Lys Asn Leu Arg Leu Ile Leu Gly Glu Gln Leu Glu Gly
                405                 410                 415
Asn Tyr Ser Phe Tyr Val Leu Asp Gln Asn Leu Gln Gln Leu Trp
                420                 425                 430
Asp Trp Asp His Arg Asn Leu Thr Ile Lys Ala Gly Lys Met Tyr Phe
            435                 440                 445
Ala Phe Asn Pro Lys Leu Cys Val Ser Glu Ile Tyr Arg Met Glu Glu
            450                 455                 460
Val Thr Gly Thr Lys Gly Arg Gln Ser Lys Gly Asp Ile Asn Thr Arg
465                 470                 475                 480
Asn Asn Gly Glu Arg Ala Ser Cys Glu Ser Asp Val Leu His Phe Thr
                485                 490                 495
Ser Thr Thr Thr Ser Lys Asn Arg Ile Ile Thr Trp His Arg Tyr
                500                 505                 510
Arg Pro Pro Asp Tyr Arg Asp Leu Ile Ser Phe Thr Val Tyr Tyr Lys
            515                 520                 525
Glu Ala Pro Phe Lys Asn Val Thr Glu Tyr Asp Gly Gln Asp Ala Cys
            530                 535                 540
Gly Ser Asn Ser Trp Asn Met Val Asp Val Asp Leu Pro Pro Asn Lys
545                 550                 555                 560
Asp Val Glu Pro Gly Ile Leu Leu His Gly Leu Lys Pro Trp Thr Gln
                565                 570                 575
Tyr Ala Val Tyr Val Lys Ala Val Thr Leu Thr Met Val Glu Asn Asp
                580                 585                 590
His Ile Arg Gly Ala Lys Ser Glu Ile Leu Tyr Ile Arg Thr Asn Ala
            595                 600                 605
Ser Val Pro Ser Ile Pro Leu Asp Val Leu Ser Ala Ser Asn Ser Ser
            610                 615                 620
Ser Gln Leu Ile Val Lys Trp Asn Pro Pro Ser Leu Pro Asn Gly Asn
625                 630                 635                 640
Leu Ser Tyr Tyr Ile Val Arg Trp Gln Arg Gln Pro Gln Asp Gly Tyr
                645                 650                 655
Leu Tyr Arg His Asn Tyr Cys Ser Lys Asp Lys Ile Pro Ile Arg Lys
                660                 665                 670
Tyr Ala Asp Gly Thr Ile Asp Ile Glu Glu Val Thr Glu Asn Pro Lys
            675                 680                 685
Thr Glu Val Cys Gly Gly Glu Lys Gly Pro Cys Cys Ala Cys Pro Lys
            690                 695                 700
Thr Glu Ala Glu Lys Gln Ala Glu Lys Glu Glu Ala Glu Tyr Arg Lys
705                 710                 715                 720
Val Phe Glu Asn Phe Leu His Asn Ser Ile Phe Val Pro Arg Pro Glu
                725                 730                 735
Arg Lys Arg Arg Asp Val Met Gln Val Ala Asn Thr Thr Met Ser Ser
            740                 745                 750
Arg Ser Arg Asn Thr Thr Ala Ala Asp Thr Tyr Asn Ile Thr Asp Pro
            755                 760                 765
```

-continued

Glu Glu Leu Glu Thr Glu Tyr Pro Phe Phe Glu Ser Arg Val Asp Asn
770                 775                 780

Lys Glu Arg Thr Val Ile Ser Asn Leu Arg Pro Phe Thr Leu Tyr Arg
785                 790                 795                 800

Ile Asp Ile His Ser Cys Asn His Glu Ala Glu Lys Leu Gly Cys Ser
                805                 810                 815

Ala Ser Asn Phe Val Phe Ala Arg Thr Met Pro Ala Glu Gly Ala Asp
                820                 825                 830

Asp Ile Pro Gly Pro Val Thr Trp Glu Pro Arg Pro Glu Asn Ser Ile
                835                 840                 845

Phe Leu Lys Trp Pro Glu Pro Glu Asn Pro Asn Gly Leu Ile Leu Met
850                 855                 860

Tyr Glu Ile Lys Tyr Gly Ser Gln Val Glu Asp Gln Arg Glu Cys Val
865                 870                 875                 880

Ser Arg Gln Glu Tyr Arg Lys Tyr Gly Gly Ala Lys Leu Asn Arg Leu
                885                 890                 895

Asn Pro Gly Asn Tyr Thr Ala Arg Ile Gln Ala Thr Ser Leu Ser Gly
                900                 905                 910

Asn Gly Ser Trp Thr Asp Pro Val Phe Phe Tyr Val Gln Ala Lys Thr
                915                 920                 925

Gly Tyr Glu Asn Phe Ile His Leu Ile Ile Ala Leu Pro Val Ala Val
                930                 935                 940

Leu Leu Ile Val Gly Gly Leu Val Ile Met Leu Tyr Val Phe His Arg
945                 950                 955                 960

Lys Arg Asn Asn Ser Arg Leu Gly Asn Gly Val Leu Tyr Ala Ser Val
                965                 970                 975

Asn Pro Glu Tyr Phe Ser Ala Ala Asp Val Tyr Val Pro Asp Glu Trp
                980                 985                 990

Glu Val Ala Arg Glu Lys Ile Thr Met Ser Arg Glu Leu Gly Gln Gly
                995                 1000                1005

Ser Phe Gly Met Val Tyr Glu Gly Val Ala Lys Gly Val Val Lys
1010                1015                1020

Asp Glu Pro Glu Thr Arg Val Ala Ile Lys Thr Val Asn Glu Ala
1025                1030                1035

Ala Ser Met Arg Glu Arg Ile Glu Phe Leu Asn Glu Ala Ser Val
1040                1045                1050

Met Lys Glu Phe Asn Cys His His Val Val Arg Leu Leu Gly Val
1055                1060                1065

Val Ser Gln Gly Gln Pro Thr Leu Val Ile Met Glu Leu Met Thr
1070                1075                1080

Arg Gly Asp Leu Lys Ser Tyr Leu Arg Ser Leu Arg Pro Glu Met
1085                1090                1095

Glu Asn Asn Pro Val Leu Ala Pro Pro Ser Leu Ser Lys Met Ile
1100                1105                1110

Gln Met Ala Gly Glu Ile Ala Asp Gly Met Ala Tyr Leu Asn Ala
1115                1120                1125

Asn Lys Phe Val His Arg Asp Leu Ala Ala Arg Asn Cys Met Val
1130                1135                1140

Ala Glu Asp Phe Thr Val Lys Ile Gly Asp Phe Gly Met Thr Arg
1145                1150                1155

Asp Ile Tyr Glu Thr Asp Tyr Tyr Arg Lys Gly Gly Lys Gly Leu
1160                1165                1170

```
Leu Pro Val Arg Trp Met Ser Pro Glu Ser Leu Lys Asp Gly Val
1175                1180                1185

Phe Thr Thr Tyr Ser Asp Val Trp Ser Phe Gly Val Val Leu Trp
1190                1195                1200

Glu Ile Ala Thr Leu Ala Glu Gln Pro Tyr Gln Gly Leu Ser Asn
1205                1210                1215

Glu Gln Val Leu Arg Phe Val Met Glu Gly Gly Leu Leu Asp Lys
1220                1225                1230

Pro Asp Asn Cys Pro Asp Met Leu Phe Glu Leu Met Arg Met Cys
1235                1240                1245

Trp Gln Tyr Asn Pro Lys Met Arg Pro Ser Phe Leu Glu Ile Ile
1250                1255                1260

Ser Ser Ile Lys Glu Glu Met Glu Pro Gly Phe Arg Glu Val Ser
1265                1270                1275

Phe Tyr Tyr Ser Glu Glu Asn Lys Leu Pro Glu Pro Glu Glu Leu
1280                1285                1290

Asp Leu Glu Pro Glu Asn Met Glu Ser Val Pro Leu Asp Pro Ser
1295                1300                1305

Ala Ser Ser Ser Ser Leu Pro Leu Pro Asp Arg His Ser Gly His
1310                1315                1320

Lys Ala Glu Asn Gly Pro Gly Pro Gly Val Leu Val Leu Arg Ala
1325                1330                1335

Ser Phe Asp Glu Arg Gln Pro Tyr Ala His Met Asn Gly Gly Arg
1340                1345                1350

Lys Asn Glu Arg Ala Leu Pro Leu Pro Gln Ser Ser Thr Cys
1355                1360                1365

<210> SEQ ID NO 15
<211> LENGTH: 191
<212> TYPE: PRT
<213> ORGANISM: Homo sapiens

<400> SEQUENCE: 15

Met Asn Phe Leu Leu Ser Trp Val His Trp Ser Leu Ala Leu Leu
1               5                   10                  15

Tyr Leu His His Ala Lys Trp Ser Gln Ala Ala Pro Met Ala Glu Gly
                20                  25                  30

Gly Gly Gln Asn His His Glu Val Val Lys Phe Met Asp Val Tyr Gln
                35                  40                  45

Arg Ser Tyr Cys His Pro Ile Glu Thr Leu Val Asp Ile Phe Gln Glu
50                  55                  60

Tyr Pro Asp Glu Ile Glu Tyr Ile Phe Lys Pro Ser Cys Val Pro Leu
65                  70                  75                  80

Met Arg Cys Gly Gly Cys Cys Asn Asp Glu Gly Leu Glu Cys Val Pro
                85                  90                  95

Thr Glu Glu Ser Asn Ile Thr Met Gln Ile Met Arg Ile Lys Pro His
                100                 105                 110

Gln Gly Gln His Ile Gly Glu Met Ser Phe Leu Gln His Asn Lys Cys
                115                 120                 125

Glu Cys Arg Pro Lys Lys Asp Arg Ala Arg Gln Glu Asn Pro Cys Gly
                130                 135                 140

Pro Cys Ser Glu Arg Arg Lys His Leu Phe Val Gln Asp Pro Gln Thr
145                 150                 155                 160
```

-continued

```
Cys Lys Cys Ser Cys Lys Asn Thr Asp Ser Arg Cys Lys Ala Arg Gln
                165                 170                 175

Leu Glu Leu Asn Glu Arg Thr Cys Arg Cys Asp Lys Pro Arg Arg
            180                 185                 190

<210> SEQ ID NO 16
<211> LENGTH: 504
<212> TYPE: PRT
<213> ORGANISM: Artificial
<220> FEATURE:
<223> OTHER INFORMATION: Human angiopoietin-2 (ANG-2) with leader and
      His-tag

<400> SEQUENCE: 16

Met Trp Gln Ile Val Phe Phe Thr Leu Ser Cys Asp Leu Val Leu Ala
1               5                   10                  15

Ala Ala Tyr Asn Asn Phe Arg Lys Ser Met Asp Ser Ile Gly Lys Lys
            20                  25                  30

Gln Tyr Gln Val Gln His Gly Ser Cys Ser Tyr Thr Phe Leu Leu Pro
        35                  40                  45

Glu Met Asp Asn Cys Arg Ser Ser Ser Pro Tyr Val Ser Asn Ala
    50                  55                  60

Val Gln Arg Asp Ala Pro Leu Glu Tyr Asp Asp Ser Val Gln Arg Leu
65                  70                  75                  80

Gln Val Leu Glu Asn Ile Met Glu Asn Asn Thr Gln Trp Leu Met Lys
                85                  90                  95

Leu Glu Asn Tyr Ile Gln Asp Asn Met Lys Lys Glu Met Val Glu Ile
            100                 105                 110

Gln Gln Asn Ala Val Gln Asn Gln Thr Ala Val Met Ile Glu Ile Gly
        115                 120                 125

Thr Asn Leu Leu Asn Gln Thr Ala Glu Gln Thr Arg Lys Leu Thr Asp
    130                 135                 140

Val Glu Ala Gln Val Leu Asn Gln Thr Thr Arg Leu Glu Leu Gln Leu
145                 150                 155                 160

Leu Glu His Ser Leu Ser Thr Asn Lys Leu Glu Lys Gln Ile Leu Asp
                165                 170                 175

Gln Thr Ser Glu Ile Asn Lys Leu Gln Asp Lys Asn Ser Phe Leu Glu
            180                 185                 190

Lys Lys Val Leu Ala Met Glu Asp Lys His Ile Ile Gln Leu Gln Ser
        195                 200                 205

Ile Lys Glu Glu Lys Asp Gln Leu Gln Val Leu Val Ser Lys Gln Asn
210                 215                 220

Ser Ile Ile Glu Glu Leu Glu Lys Lys Ile Val Thr Ala Thr Val Asn
225                 230                 235                 240

Asn Ser Val Leu Gln Lys Gln Gln His Asp Leu Met Glu Thr Val Asn
                245                 250                 255

Asn Leu Leu Thr Met Met Ser Thr Ser Asn Ser Ala Lys Asp Pro Thr
            260                 265                 270

Val Ala Lys Glu Glu Gln Ile Ser Phe Arg Asp Cys Ala Glu Val Phe
        275                 280                 285

Lys Ser Gly His Thr Thr Asn Gly Ile Tyr Thr Leu Thr Phe Pro Asn
    290                 295                 300

Ser Thr Glu Glu Ile Lys Ala Tyr Cys Asp Met Glu Ala Gly Gly Gly
305                 310                 315                 320

Gly Trp Thr Ile Ile Gln Arg Arg Glu Asp Gly Ser Val Asp Phe Gln
                325                 330                 335
```

```
                                  -continued

Arg Thr Trp Lys Glu Tyr Lys Val Gly Phe Gly Asn Pro Ser Gly Glu
            340                 345                 350

Tyr Trp Leu Gly Asn Glu Phe Val Ser Gln Leu Thr Asn Gln Gln Arg
        355                 360                 365

Tyr Val Leu Lys Ile His Leu Lys Asp Trp Glu Gly Asn Glu Ala Tyr
    370                 375                 380

Ser Leu Tyr Glu His Phe Tyr Leu Ser Ser Glu Glu Leu Asn Tyr Arg
385                 390                 395                 400

Ile His Leu Lys Gly Leu Thr Gly Thr Ala Gly Lys Ile Ser Ser Ile
                405                 410                 415

Ser Gln Pro Gly Asn Asp Phe Ser Thr Lys Asp Gly Asp Asn Asp Lys
            420                 425                 430

Cys Ile Cys Lys Cys Ser Gln Met Leu Thr Gly Gly Trp Trp Phe Asp
            435                 440                 445

Ala Cys Gly Pro Ser Asn Leu Asn Gly Met Tyr Tyr Pro Gln Arg Gln
    450                 455                 460

Asn Thr Asn Lys Phe Asn Gly Ile Lys Trp Tyr Tyr Trp Lys Gly Ser
465                 470                 475                 480

Gly Tyr Ser Leu Lys Ala Thr Thr Met Met Ile Arg Pro Ala Asp Phe
                485                 490                 495

Ser Gly His His His His His His
            500
```